US008962566B2

(12) United States Patent
Kozlowski et al.

(10) Patent No.: US 8,962,566 B2
(45) Date of Patent: *Feb. 24, 2015

(54) MULTI-ARM POLYMERIC ALKANOATE CONJUGATES

(71) Applicant: Nektar Therapeutics, San Francisco, CA (US)

(72) Inventors: Antoni Kozlowski, Huntsville, AL (US); Samuel P. McManus, Guntersville, AL (US); Jennifer Riggs-Sauthier, San Francisco, CA (US); Xiaoming Shen, Millbrae, CA (US); Wen Zhang, San Ramon, CA (US)

(73) Assignee: Nektar Therapeutics, San Francisco, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/137,090

(22) Filed: Dec. 20, 2013

(65) Prior Publication Data
US 2014/0113961 A1 Apr. 24, 2014

(51) Int. Cl.
*A61K 47/48* (2006.01)

(52) U.S. Cl.
CPC ............................. *A61K 47/48215* (2013.01)
USPC ........ 514/19.3; 525/419; 424/78.08; 514/779

(58) Field of Classification Search
CPC .................................................. A61K 8/2123
USPC .......................................................... 424/85.6
See application file for complete search history.

(56) References Cited

U.S. PATENT DOCUMENTS

| | | | |
|---|---|---|---|
| 5,321,095 A | 6/1994 | Greenwald | |
| 5,614,549 A | 3/1997 | Greenwald et al. | |
| 5,629,384 A | 5/1997 | Veronese et al. | |
| 5,648,506 A | 7/1997 | Desai et al. | |
| 5,681,567 A | 10/1997 | Martinez et al. | |
| 5,840,900 A | 11/1998 | Greenwald et al. | |
| 5,859,022 A | 1/1999 | Hausheer et al. | |
| 5,880,131 A | 3/1999 | Greenwald et al. | |
| 5,965,566 A | 10/1999 | Greenwald et al. | |
| 6,011,042 A | 1/2000 | Greenwald et al. | |
| 6,121,451 A | 9/2000 | Henegar et al. | |
| 6,127,355 A | 10/2000 | Greenwald et al. | |
| 6,153,655 A | 11/2000 | Martinez et al. | |
| 6,194,580 B1 | 2/2001 | Greenwald et al. | |
| 6,362,254 B2 | 3/2002 | Harris et al. | |
| 6,395,266 B1 | 5/2002 | Martinez et al. | |
| 6,403,569 B1 | 6/2002 | Achterrath | |
| 6,461,603 B2 | 10/2002 | Bentley et al. | |
| 6,495,659 B2 | 12/2002 | Bentley et al. | |
| 6,608,076 B1 | 8/2003 | Greenwald et al. | |
| 7,744,861 B2 | 6/2010 | Zhao et al. | |
| 8,637,466 B2 * | 1/2014 | Kozlowski et al. | 514/19.3 |
| 2001/0041172 A1 | 11/2001 | Bentley et al. | |
| 2002/0182172 A1 | 12/2002 | Bentley et al. | |
| 2003/0105275 A1 | 6/2003 | Bentley et al. | |
| 2004/0037802 A1 | 2/2004 | Zhao et al. | |
| 2004/0058981 A1 | 3/2004 | Lai et al. | |
| 2004/0077595 A1 | 4/2004 | Cheng et al. | |
| 2005/0036978 A1 | 2/2005 | Kozlowski | |
| 2005/0112088 A1 | 5/2005 | Zhao et al. | |
| 2006/0105046 A1 | 5/2006 | Bentley et al. | |
| 2006/0182716 A1 * | 8/2006 | Hong et al. | 424/85.6 |
| 2006/0204473 A1 * | 9/2006 | Blatt et al. | 424/85.5 |
| 2007/0025956 A1 | 2/2007 | Burton et al. | |
| 2007/0197575 A1 | 8/2007 | Zhao et al. | |
| 2011/0200550 A1 | 8/2011 | Kozlowksi et al. | |

FOREIGN PATENT DOCUMENTS

| | | |
|---|---|---|
| EP | 0 757 049 | 3/1999 |
| EP | 0 923 566 | 10/2003 |
| WO | WO 97/33552 | 9/1997 |
| WO | WO 98/41562 | 9/1998 |
| WO | WO 99/53951 | 10/1999 |
| WO | WO 00/64486 | 11/2000 |
| WO | WO 01/46291 | 6/2001 |
| WO | WO 01/62299 | 8/2001 |
| WO | WO 01/74402 | 10/2001 |
| WO | WO 02/08789 | 1/2002 |
| WO | WO 02/43772 | 6/2002 |
| WO | WO 03/031467 | 4/2003 |
| WO | WO 03/037384 | 5/2003 |
| WO | WO 03/037385 | 5/2003 |
| WO | WO 2004/012773 | 2/2004 |
| WO | WO 2004/060967 | 7/2004 |
| WO | WO 2005/028539 | 3/2005 |
| WO | WO 2007/098466 | 8/2007 |
| WO | WO 2008/066902 | 6/2008 |

OTHER PUBLICATIONS

Astruc, et al., "Dendritic Catalysts and Dendrimers in Catalysis," Chem. Rev., vol. 101, pp. 2991-3023, (2001).

Bacchi, et al., "Novel Synthetic Polyamines are Effective in the Treatment of Experimental Microsporidiosis, an Opportunistic AIDS-Associated Infection," Antimicrob. Agents and Chemotherp., vol. 46, No. 1, pp. 55-61, (Jan. 2002).

Benoiton, et al., "2-Alkoxy-5(4H)-oxazolones from N-alkoxycarbonylamino acids and their implications in carbodiimide-mediated reactions in peptide synthesis," Can. J. Chem., vol. 59, pp. 384-389, (1981).

(Continued)

*Primary Examiner* — Walter Webb
(74) *Attorney, Agent, or Firm* — Mark A. Wilson

(57) ABSTRACT

Among other aspects, provided herein are multi-armed polymer conjugates comprising an alkanoate-linker, compositions comprising such conjugates, and related methods of making and administering the same. Methods of treatment employing such conjugates and related uses are also provided. The conjugates are prepared with high drug loading efficiencies.

2 Claims, 7 Drawing Sheets

(56) References Cited

OTHER PUBLICATIONS

Conover, et al., "Camptothecin delivery systems: enhanced efficacy and tumor accumulation of camptothecin following its conjugation to polyethylene glycol via a glycine linker," Can. Chemother. Pharmacol., vol. 42, pp. 407-414, (1998).

Conover, et al., "Camptothecin delivery systems: the utility of amino acid spacers for the conjugation of camptothecin with polyethylene glycol to create prodrugs," Anti-Cancer Drug Des., vol. 14, pp. 499-506, (1999).

Cook, et al., "Species Dependent Esterase Activities for Hydrolysis of an Anti-HIV Prodrug Glycovir and Bioavailability of Active SC-48334," Pharmaceut. Res., vol. 12, No. 8, pp. 1158-1164, (1995).

De Jesus, et al., "Polyester Dendritic Systems for Drug Delivery Applications: In Vitro and In Vivo Evaluation," Bioconj. Chem., vol. 13, pp. 453-461, (2002).

Dubois, "Recent progress in the development of docetaxel and paclitaxel analogues", Expert Opin. Ther. Patents, vol. 16, No. 11, pp. 1481-1496, (2006).

Ericsson, et al., "In vitro hydrolysis rate and protein binding of clevidipine, a new ultrashort-acting calcium antagonist metabolised by esterases, in different animal species and man," Euro. J. of Pharmaceut. Sci., vol. 8, pp. 29-37, (1999).

Greenwald, et al., "Poly(ethylene glycol) Conjugated Drugs and Prodrugs: A Comprehensive Review," Crit. Rev. in Therp. Drug Carr. Sys., vol. 17, No. 2, pp. 101-161, (2000).

Kaliste-Korhonen, et al., "Interspecies differences in enzymes reacting with organophosphates and their inhibition by paraoxon in vitro," Hum. & Exp. Toxicol., vol. 15, pp. 972-978, (1996).

Li, et al., "Butyrylcholinesterase, paraoxonase, and albumin esterase, but not carboxylesterase, are present in human plasma," Biochem. Pharmacol., vol. 70, pp. 1673-1684, (2005).

Minagawa, et al., "Species Differences in Hydrolysis of Isocarbacyclin Methyl Ester (TEI-9090) by Blood Esterases," Biochem. Pharmacol., vol. 49, No. 10, pp. 1361-1365, (1995).

Quon, et al., "Species Differences in the Stereoselective Hydrolysis of Esmolol by Blood Esterases," Drug Metabol. and Disposition, vol. 16, No. 3, pp. 425-428, (1988).

Warnecke, et al., "Maleimide-oligo(ethylene glycol) Derivatives of Camptothecin as Albumin-Binding Prodrugs: Synthesis and Antitumor Efficacy," Bioconj. Chem., vol. 14, pp. 377-387, (2003).

Williams, "Clinical Significance of Esterases in Man," Clin. Pharmacokin., vol. 10, pp. 392-403, (1985).

Zalipsky, et al., "Attachment of Drugs to Polyethylene Glycols," Eur. Polym. J., vol. 19, No. 12, pp. 1177-1183, (1983).

PCT International Search Report corresponding to PCT Application No. PCT/US2009/004618 date of mailing Dec. 29, 2009.

PCT International Preliminary Report on Patentability corresponding to PCT Application No. PCT/US2009/004618 date of mailing Feb. 24, 2011.

Enzon Pharmaceuticals, Macromolecular Engineering Technologies, 16 pages, (2004).

NEKTAR™—Transforming Therapeutics, Nektar Molecule Engineering: Polyethylene Glycol and Derivatives for Advanced PEGylation, 24 pages, Catalog—2003, (Jul. 2003).

NEKTAR™—Transforming Therapeutics, Nektar Advanced PEGylation: Polyethylene Glycol and Derivatives for Advanced PEGylation, 27 pages, Catalog—2004, (Jul. 2004).

NEKTAR™—Transforming Therapeutics, Nektar Advanced PEGylation: Polyethylene Glycol and Derivatives for Advanced PEGylation, 33 pages, (Catalog 2005—2006).

NOF Corporation, PEG Derivatives, Phospholipid and Drug Delivery Materials for Pharmaceuticals, 46 pages, Catalogue 2003-$1^{st}$, (Jan. 2003).

NOF Corporation, PEG Derivatives, Phospholipid and Drug Delivery Materials for Pharmaceuticals, 27 pages, Catalogue 2003-$2^{nd}$, (Mar. 2004).

NOF Corporation, PEG Derivatives, Phospholipids and Drug Delivery Materials for Pharmaceutical Products and Formulations, 60 pages, Catalogue Ver. 8, (Apr. 2006).

Polypure Products, PEG amines; PEG acids and amino acids; PEG thiols and disulfides; Biotins, 5 pages, (Apr. 2004).

Polypure Products, PEG amines; PEG acids and amino acids; PEG thiols and disulfides; Biotins, 5 pages, (Apr. 2005).

Quanta Biodesign, Labeling, Derivatization and Crosslinking Reagents for Biological and Related Materials with dPEG™, 38 pages, (Mar. 12, 2004).

Quanta Biodesign, Labeling, Modification and Crosslinking Reagents incorporating our unique monodispersed dPEG™ Technology, 31 pages, (Nov. 5, 2004).

Quanta Biodesign, Ltd., Leading innovator, producer and provider of monodisperse discrete PEG™ (dPEG™) derivatives, (Product Catalog), 26 pages, (Updated: Jul. 18, 2005).

Quanta Biodesign, Ltd., Leading innovator, producer and provider of monodisperse discrete PEG™ (dPEG™) derivatives, (Product Catalog), 26 pages, (Updated: Nov. 17, 2005).

Shearwater Polymers, Inc., Polyethylene Glycol Derivatives, 50 pages, Catalog—(Mar. 1995).

Shearwater Polymers, Inc., Polyethylene Glycol Derivatives, 55 pages, Catalog 1997-1998, (Jul. 1997).

Shearwater Polymers, Inc., Polyethylene Glycol and Derivatives: Functionalized Biocompatible Polymers for Research and Pharmaceuticals, 50 pages, Catalog—(Jan. 2000).

Shearwater Corporation, Polyethylene Glycol and Derivatives for Biomedical Applications, 20 pages, Catalog—(Jul. 2001).

Australian Patent Examination Report No. 1 corresponding to Australian Patent Application No. 2009282413 dated Jun. 14, 2013.

Notification of the First Office Action corresponding to Chinese Patent Application No. 200980136289.7 dated Mar. 26, 2012.

Chinese Notification of the Second Office Action corresponding to Chinese Patent Application No. 200980136289.7 date of notification Feb. 1, 2013.

Communication corresponding to European Patent Application No. 09 789 119.6-1216 dated Nov. 4, 2011.

Chinese Notification of the Third Office Action corresponding to Chinese Patent Application No. 200980136289.7 date of notification Nov. 1, 2013.

Israel First Substantive Examination Report corresponding to Israel Patent Application No. 211180 dated Feb. 3, 2014.

Japanese Notice of Reasons for Rejection corresponding to Japanese Patent Application No. 2011-522993 mailing date Oct. 18, 2013.

Japanese Notice of Reasons for Rejection corresponding to Japanese Patent Application No. 2011-522993 mailing date Feb. 4, 2014.

Mexican Communication of the Substantive Examination Report corresponding to Mexican Patent Application No. MX/a/2011/001583 dated Mar. 5, 2014.

* cited by examiner

MULTI-ARM POLYMERIC ALKANOATE CONJUGATES

CROSS REFERENCE TO RELATED APPLICATIONS

This application is a continuation of U.S. patent application Ser. No. 13/058,320, filed May 6, 2011, now U.S. Pat. No. 8,637,466, which is a 35 U.S.C. §371 application of International Application No. PCT/US2009/004618, filed Aug. 11, 2009, designating the United States, which claims the benefit of priority to: Provisional Patent Application No. 61/087,826, filed Aug. 11, 2008; Provisional Patent Application No. 61/106,928, filed Oct. 20, 2008; and Provisional Application No. 61/113,328, filed 11 Nov. 2008; the contents of which are each hereby expressly incorporated herein by reference in their entireties.

FIELD

This disclosure relates generally to multi-arm, water-soluble polymers and their corresponding drug conjugates. In particular, the disclosure is directed to, among other features, multi-armed polymer conjugates having drug covalently attached to the multi-arm polymer via an alkanoate-linkage. Also disclosed are pharmaceutical compositions comprising such conjugates, and methods for preparing, formulating, administering, and using such conjugates and related compositions.

BACKGROUND

Over the years, numerous methods have been proposed for improving the delivery of biologically active agents, particularly small molecule drugs. Challenges associated with the formulation and delivery of pharmaceutical agents can include poor aqueous solubility of the pharmaceutical agent, toxicity, low bioavailability, instability, and rapid in-vivo degradation, to name just a few. Although many approaches have been devised for improving the delivery of pharmaceutical agents, no single approach is without its drawbacks. For instance, commonly employed drug delivery approaches aimed at solving or at least ameliorating one or more of these challenges include drug encapsulation (such as in a liposome, polymer matrix, or unimolecular micelle), covalent attachment to a water-soluble polymer (i.e., conjugation) such as polyethylene glycol (i.e., PEG or PEGylation), use of gene targeting agents, and the like.

PEGylation has been employed to a limited degree to improve the bioavailability and ease of formulation of small molecule therapeutics having poor aqueous solubilities. For instance, water-soluble polymers such as PEG have been covalently attached to artilinic acid to improve its aqueous solubility. See U.S. Pat. No. 6,461,603. Similarly, PEG has been covalently attached to triazine-based compounds such as trimelamol to improve their solubility in water and enhance their chemical stability. See International Patent Application Publication No. WO 02/043772. Covalent attachment of PEG to bisindolyl maleimides has been employed to improve poor bioavailability of such compounds due to low aqueous solubility. See International Patent Application Publication No. WO 03/037384). Polymer conjugates of non-steroidal anti-inflammatory drugs (NSAIDs) and of opioid antagonists have also been prepared. See U.S. Patent Application Publication Nos. 2007/0025956 and 2006/0105046, respectively. Prodrugs of camptothecin having one or two molecules of camptothecin covalently attached to a linear polyethylene glycol have also been prepared. See U.S. Pat. No. 5,880,131.

Certain drugs, such as the alkaloids, are notoriously difficult to solubilize (i.e., formulate). Such alkaloids include the taxanes, such as docetaxel, and the camptothecins, such as irinotecan. Camptothecin (often abbreviated as "CPT") is a phytotoxic alkaloid first isolated from the wood and bark of *Camptotheca acuminata* (Nyssaceae), and has been shown to exhibit antitumor activity. The compound has a pentacyclic ring system with an asymmetric center in lactone ring E with a 20 S configuration. The pentacyclic ring system includes a pyrrolo[3,4-b]quinoline (rings A, B and C), a conjugated pyridone (ring D), and a six-membered lactone (ring E) with a 20-hydroxyl group. Due to its insolubility in water, camptothecin was initially evaluated clinically in the form of a water-soluble carboxylate salt having the lactone ring open to form the sodium salt. The sodium salt, although exhibiting much improved water solubility in comparison to camptothecin itself, produced severe toxicity and demonstrated very little in vivo anticancer activity, thus demonstrating the undesirability of this approach. A Phase I clinical trial for a linear PEG-paclitaxel compound for treatment of patients with advanced solid tumors and lymphomas in 2001; the trial has since been terminated.

In an effort to address the poor aqueous solubility associated with camptothecin and many of its derivatives, a number of synthetic efforts have been directed to derivatizing the A-ring and/or B-ring or esterifying the 20-hydroxyl to improve water-solubility while maintaining cytotoxic activity. For example, topotecan (9-dimethylaminomethyl-10-hydroxy CPT) and irinotecan (7-ethyl-10[4-(1-piperidino)-1-piperidino]carbonyloxy CPT), otherwise known as CPT-11, are two water-soluble CPT derivatives that have shown clinically useful activity. Conjugation of certain camptothecin derivatives, such as 10-hydroxycamptothecin and 11-hydroxycamptothecin, to a linear poly(ethylene glycol) molecule via an ester linkage has been described as a means to form water soluble prodrugs. See U.S. Pat. No. 6,011,042. The approach used relies on reaction of an aromatic, hydroxyl-containing compound with an activated polymer.

The clinical effectiveness of many small molecule therapeutics such as the foregoing, and oncolytics in particular, is limited by several factors such as dose-related toxicity. For instance, irinotecan and other camptothecin derivatives undergo an undesirable hydrolysis of the E-ring lactone under alkaline conditions. Additionally, administration of irinotecan causes a number of troubling side effects, including leukopenia, neutropenia, and diarrhea. Due to its severe diarrheal side-effect, the dose of irinotecan that can be administered in its conventional, unmodified form is extremely limited, thus hampering the efficacy of this drug and others of this type.

These associated side effects, when severe, can be sufficient to arrest further use as well as development of such drugs as promising therapeutics. Additional challenges facing small molecules include high clearance rates, and, with respect to anticancer agents, minimal tumor permeation and residence time. Approaches involving the use of polymer attachment must balance the size of the polymer against the molecular weight of the active agent in order to allow therapeutically effective doses to be delivered, and at a clinically useful rate. Finally, the synthesis of a modified or drug delivery-enhanced active agent must result in reasonable yields, and in a reproducibly prepared product, to make any such approach economically attractive. Thus, there exists a need for new methods for effectively delivering drugs, and in particular small molecule drugs, and even more particularly oncolytics, which can reduce their adverse and often toxic side-effects, whilst simultaneously improving their preparation, efficacy and ease of formulation. Even more importantly, there exists a need to provide oncolytic products that are effective against drug resistant tumors. Specifically, there is a need for improved methods for delivering drugs such as the foregoing that possess an optimal balance of bioavailability due to reduced clearance times, bioactivity, and efficacy, coupled with reduced side-effects.

SUMMARY

In a first aspect, the present disclosure provides a multi-arm polymer conjugate having the following structure, Compound I

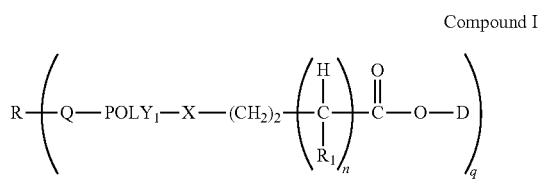

where: R is an organic core radical comprising from about 3 to about 150 carbon atoms; Q is a linker; $POLY_1$ is a water-soluble and non-peptidic polymer segment; X is a spacer that is optionally present; $R_1$, in each occurrence, is independently selected from the group consisting of H, lower alkyl, and an electron withdrawing group; n is an integer in the range from 1 to 7 (e.g., is selected from 1, 2, 3, 4, 5, 6, and 7); D is a residue of a small molecule having a molecular weight of less than about 800 daltons; and q is 3 or greater.

Each of the following embodiments described herein may be considered singly, or taken in combination with any one or more additional embodiments, so long as the particular combination is not mutually inconsistent with the particular embodiments included in such combination.

In particular embodiments in reference to Compound I, D is an anticancer agent.

In yet other embodiments, the variable "R" is an organic core radical possessing from about 3 to about 25 carbon atoms. In yet further embodiments, R can be linear or cyclic. In additional embodiments, R is a saturated, aliphatic core. Exemplary multi-armed polymer conjugates include those where R, when taken together with Q over each of "q" arms, is a residue of a polyol, a polythiol, or a polyamine. In one or more particular embodiments, R, when taken together with Q over each of "q" arms, is a residue of glycerol, trimethylolpropane, pentaerythritol, sorbitol, or an oligomer of glycerol.

In yet other embodiments, linker, "Q," is hydrolytically stable. Particular embodiments related to Q include the following: in one or more embodiments, Q contains from about 1 to about 10 atoms; in other embodiments, Q is selected from the group consisting of —O—, —S—, —NH—, —C(O)—NH—, and —NH—C(O)—.

In yet other embodiments, $POLY_1$ is a polymer selected from the group consisting of poly(alkylene glycol), poly(olefinic alcohol), poly(vinylpyrrolidone), poly(hydroxyalkylmethacrylamide), poly(hydroxyalkylmethacrylate), poly(saccharide), poly(α-hydroxy acid), poly(acrylic acid), polyvinyl alcohol), polyphosphazene, polyoxazoline, poly(N-acryloylmorpholine), or copolymers or terpolymers thereof.

In preferred embodiments, $POLY_1$ is a polyethylene glycol.

Additional embodiments directed to $POLY_1$ include the following: in one or more embodiments, $POLY_1$ is linear; in yet other embodiments, the weight average molecular weight of $POLY_1$ ranges from about 200 to about 30,000 daltons.

In further embodiments, the weight average molecular weight of the conjugate is about 20,000 daltons or greater, e.g., in a molecular weight range of about 20,000 to about 80,000 daltons.

Particular embodiments directed to variable "X" (which is optionally present) include the following. In one or more embodiments, X has an atom length of from about 1 atom to about 50 atoms. In yet other embodiments, X has an atom length of from about 1 atom to about 25 atoms (e.g., is selected from 1, 2, 3, 4, 5, 6, 7, 8, 9, 10, 11, 12, 13, 14, 15, 16, 17, 18, 19, 20, 21, 22, 23, 24, 25, or a range therein). In further embodiments, X is oxygen ("—O—"). In a particular embodiment when $POLY_1$ is a linear polyethylene glycol corresponding to the structure, —$(CH_2CH_2O)_nCH_2CH_2$—, X is oxygen ("—O—").

Additional embodiments related to the variable "$R_1$" include the following. In one or more embodiments, $R_1$ is H. In yet other embodiments, $R_1$ is H for all "n" occurrences. In yet other embodiments, each $R_1$ in each occurrence [i.e., for each of "n" of (~C(H)$R_1$~)] is independently selected from methyl, ethyl, propyl, n-butyl, isopropyl and isobutyl. In yet other embodiments, each $R_1$ is independently selected from a halide (e.g., fluoride, chloride, bromide, and iodide), a nitrile, —$NO_2$, and —$CF_3$. In preferred embodiments, $R_1$ is hydrogen. In yet other embodiments, $R_1$ is other than hydrogen only when positioned on the alpha carbon adjacent to the carbonyl. In further embodiments, $R_1$ is methyl when positioned on the alpha carbon.

Turning now to the variable "q," particular embodiments directed to "q" include the following. In one or more embodiments, the value of q is selected from the group consisting of 3, 4, 5, 6, 7, 8, 9, and 10. In yet other embodiments, q is 3 or 4. In yet other embodiments, each of "q" polymer arms [-Q-$POLY_1$-X—$(CH_2)_2$—$(CHR_1)_n$C(O)OD] is the same.

Embodiments directed to the small molecule portion of the conjugate include the following. In one or more embodiments, the small molecule possesses a molecular weight ranging from about 250-700 daltons. In yet other embodiments, D is a residue of a taxane or a camptothecin. In yet further embodiments, D is a residue of paclitaxel or docetaxel. In one or more embodiments, D possesses the structure:

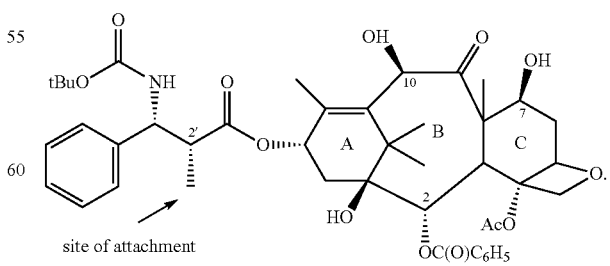

In yet a further embodiment, the multi-armed polymer conjugate possesses the structure:

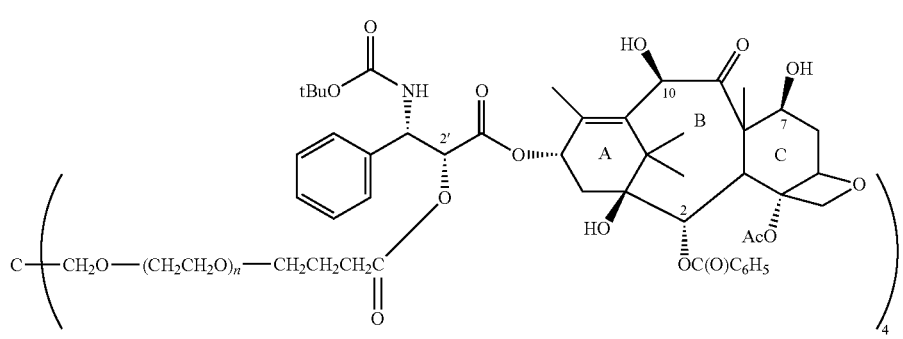

Compound Ia where n ranges from about 40 to about 500. In an embodiment related to the foregoing structure, the overall weight average molecular weight of the conjugate ranges from about 10,000 to about 80,000.

In a second aspect, provided is a pharmaceutical composition comprising a multi-armed polymer conjugate as described herein combined with a pharmaceutically acceptable carrier.

In a related embodiment in which the multi-armed polymer conjugate corresponds to Compound Ia shown above, the composition, when evaluated in a single dose study in rats, exhibits a 2-fold or greater reduction of toxicity when compared to docetaxel. In yet other embodiments, the conjugate is characterized by a drug loading of greater than or equal to 92%. In yet other embodiments, the multi-armed polymer conjugate, which corresponds to Compound Ia shown above, is further characterized by a percentage tumor growth delay (TGD) when measured at maximum tolerated dose (MTD) in any one of a H460, LoVo, or LS174T mouse xenograft model, that is 1.5-fold or more greater than that observed for docetaxel.

In a third aspect, provided herein is a method of delivering a multi-armed polymer conjugate to a mammalian subject in need thereof. The method comprises administering to the mammalian subject a therapeutically effective amount of a multi-armed polymer conjugate as provided herein.

In a fourth aspect, provided herein is a method of treating cancer in a mammalian subject. The method comprises administering a therapeutically effective amount of a conjugate as provided herein (where D is an anticancer agent) to a subject diagnosed as having one or more cancerous solid tumors over a duration of time effective to produce an inhibition of growth of said solid tumor(s) in said subject.

In an embodiment directed to the foregoing fourth aspect, the cancerous solid tumor type is selected from the group consisting of colorectal, breast, prostate, and non-small cell lung.

In a fifth aspect, provided herein is a method of treating a mammalian subject for a condition responsive to treatment with docetaxel, where the method comprises administering to the subject a therapeutically effective amount of a multi-armed polymer conjugate as provided herein.

Also provided herein are uses related to the foregoing methods.

In a sixth aspect, in a multi-armed polymer conjugate having the structure, $R(-Q-POLY_1-Y-D)_q$, where R is an organic core radical possessing from about 3 to about 150 carbon atoms, Q is a linker, $POLY_1$ is a water-soluble and non-peptidic polymer, Y is a spacer comprising a hydrolyzable linkage, such that upon hydrolysis of said hydrolyzable linkage, D is released, D is a small molecule, and q is greater than or equal to 3, provided is an improvement comprising Y having the structure,

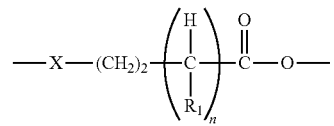

where: X is a spacer as described in further detail herein; $R_1$ is selected from the group consisting of H, lower alkyl, and an electron withdrawing group, and n is an integer from 1 to 5.

In a seventh aspect, provided is a multi-arm polymer structure having the following structure,

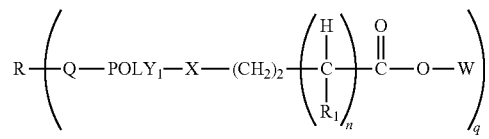

where: R is an organic core radical comprising from about 3 to about 150 carbon atoms; Q is a linker; $POLY_1$ is a water-soluble and non-peptidic polymer segment; X is a spacer; each $R_1$ is independently selected from the group consisting of H, lower alkyl, and an electron withdrawing group; n is an integer from 1 to 7; q is 3 or greater; W is selected from the group consisting of D, H, and an activated ester, where D is a residue of a small molecule having a molecular weight of less than about 800 daltons. With respect to compositions comprising this multi-arm polymer structure, on average and taking into account all species within the composition, W is preferably equal to D at a value of 0.92(q) or greater.

In an eighth aspect, provided is a method of preparing a multi-arm polymer drug conjugate. The method comprises reacting within the limits of the described chemical processes a multi-arm water-soluble polymer structure having "q" polymer arms, each having a reactive carboxylic acid group or activated ester equivalent at its terminus, with "q" equivalents or greater of a sterically hindered secondary or tertiary alcohol of a small molecule drug under conditions effective to result in conjugation of the small molecule drug to the multi-arm water soluble polymer structure via an ester linkage to form a multi-arm water soluble polymer drug conjugate wherein 92% or greater of said polymer arms have small molecule drug covalently attached thereto. The conjugate possesses a linker adjacent to the ester linkage in each of the polymer arms, where the linker is preferably absent a functional group capable of a neighboring group interaction with the ester carbonyl to form a five- or six-membered cyclic product capable of displacing the small molecule drug.

In a particular embodiment related to the eighth aspect, the linker is an alkanoate linker having the structure —$(CH_2)_2$ $(CR_1H)_nC(O)$—O—, where $R_1$ in each occurrence is independently selected from H, lower alkyl, and an electron withdrawing group, and n is an integer from 1 to 7. In yet another embodiment, prior to the reacting step, the linker is covalently attached to the drug or to each of the polymer arms.

In yet a ninth aspect, provided herein is a multi-arm polymer conjugate or reagent having the following structure:

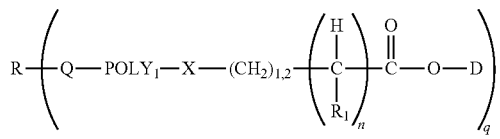

where each of the variables shown are as described above. In one particular embodiment of the foregoing, the structure possesses one methylene group adjacent to X rather than two, n is equal to one, and $R_1$ is either lower alkyl or an electron withdrawing group. 4-arm-PEG-methylpropionic acid is an exemplary structure that is useful in providing such multi-arm polymer conjugates or reagents.

Additional embodiments of the present method, compositions, and the like will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

These and other objects and features of the invention will become more fully apparent when read in conjunction with the following detailed description.

BRIEF DESCRIPTION OF THE DRAWINGS

FIG. 2A provides dose response curves for mice administered different dosages of either docetaxel or 4-ARM-$PEG_{20K}$-BA-DOC; FIG. 2B is a graphical representation of LS174T median tumor volume over time for mice administered the maximum tolerated dose (MTD) of either docetaxel or 4-ARM-$PEG_{20K}$-BA-DOC.

FIG. 3A provides dose response curves for mice administered different dosages of either docetaxel or 4-ARM-$PEG_{20K}$-BA-DOC; FIG. 3B provides a maximum tolerated dose (MTD) versus control comparison.

FIG. 4A provides dose response curves for mice administered different dosages of either docetaxel or 4-ARM-$PEG_{20K}$-BA-DOC; FIG. 4B provides a MTD comparison for mice administered the maximum tolerated dose (MTD) of either docetaxel or 4-ARM-$PEG_{20K}$-BA-DOC versus control.

DETAILED DESCRIPTION

Figure 1A:
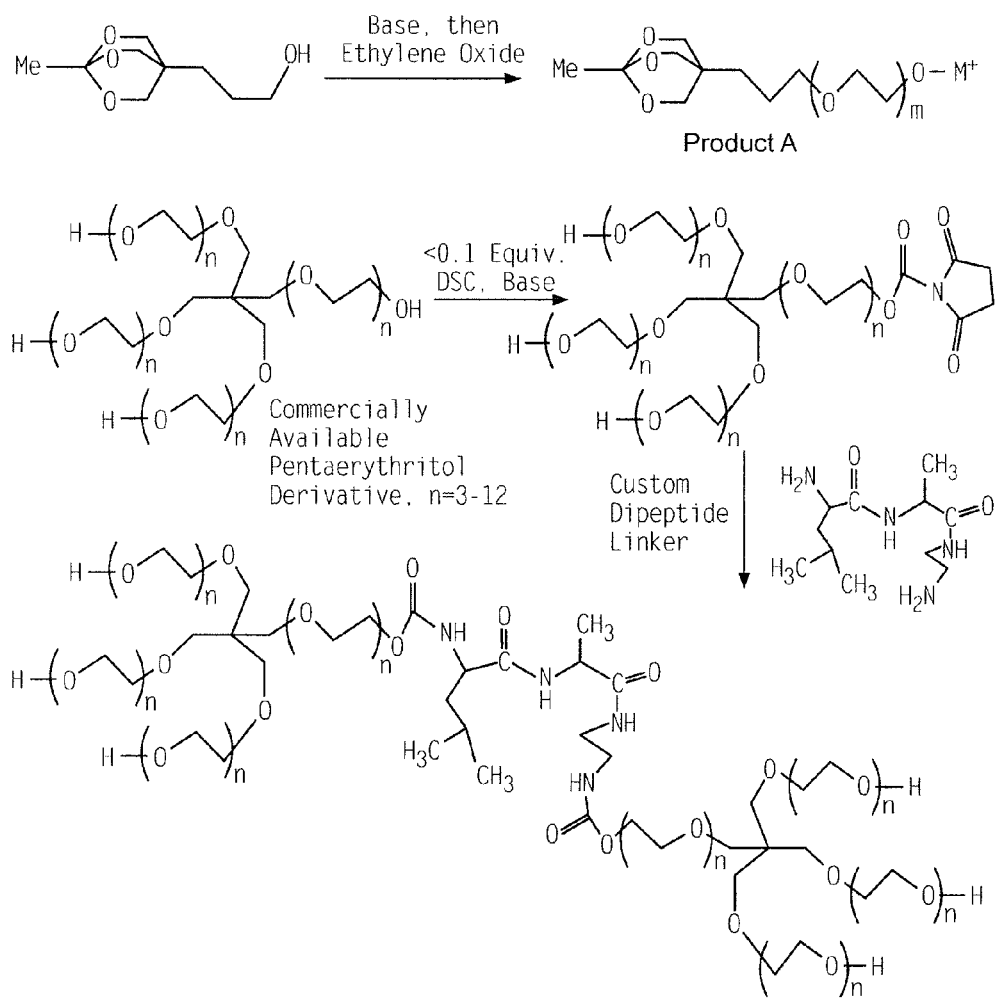
FIGS. 1A-1C demonstrate an illustrative synthesis of a dipeptide-linked pentaerythritolyl core-containing multi-armed polymer.

Various aspects of the invention now will be described more fully hereinafter. Such aspects may, however, be embodied in many different forms and should not be construed as limited to the embodiments set forth herein; rather, these embodiments are provided so that this disclosure will be thorough and complete, and will fully convey the scope of the invention to those skilled in the art.

All publications, patents and patent applications cited herein, whether supra or infra, are hereby incorporated by reference in their entirety.

Definitions

It must be noted that, as used in this specification, the singular forms "a," "an," and "the" include plural referents unless the context clearly dictates otherwise. Thus, for example, reference to a "polymer" includes a single polymer as well as two or more of the same or different polymers, reference to a "conjugate" refers to a single conjugate as well as two or more of the same or different conjugates, reference to an "excipient" includes a single excipient as well as two or more of the same or different excipients, and the like.

In describing and claiming the present invention, the following terminology will be used in accordance with the definitions described below.

A "functional group" is a group that may be used, under normal conditions of organic synthesis, to form a covalent linkage between the entity to which it is attached and another entity, which typically bears a further functional group. The functional group generally includes multiple bond(s) and/or heteroatom(s). Preferred functional groups for use in the polymers of the invention are described below.

The term "reactive" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

"Not readily reactive", with reference to a functional group present on a molecule in a reaction mixture, indicates that the group remains largely intact under conditions effective to produce a desired reaction in the reaction mixture.

An "activated derivative" of a carboxylic acid refers to a carboxylic acid derivative which reacts readily with nucleophiles, generally much more readily than the underivatized carboxylic acid. Activated carboxylic acids include, for example, acid halides (such as acid chlorides), anhydrides, carbonates, and esters. Such esters include, for example, imidazolyl esters, and benzotriazole esters, and imide esters, such as N-hydroxysuccinimidyl (NHS) esters. An activated derivative may be formed in situ by reaction of a carboxylic acid with one of various reagents, e.g. benzotriazol-1-yloxy tripyrrolidinophosphonium hexafluorophosphate (PyBOP), preferably used in combination with 1-hydroxy benzotriazole (HOBT) or 1-hydroxy-7-azabenzotriazole (HOAT); O-(7-azabenzotriazol-1-yl)-N,N,N',N'-tetramethyluronium hexafluorophosphate (HATU); or bis(2-oxo-3-oxazolidinyl) phosphinic chloride (BOP-Cl).

A "chemical equivalent" of a functional group is one that possesses essentially the same type of reactivity as the functional group. For instance, one functional group that undergoes an SN2 reaction is considered to be a functional equivalent of another such functional group.

A "protecting group" is a moiety that prevents or blocks reaction of a particular chemically reactive functional group in a molecule under certain reaction conditions. The protecting group will vary depending upon the type of chemically reactive group being protected as well as the reaction conditions to be employed and the presence of additional reactive or protecting groups in the molecule. Functional groups that may be protected include, by way of example, carboxylic acid groups, amino groups, hydroxyl groups, thiol groups, carbonyl groups and the like. Representative protecting groups for carboxylic acids include esters (such as a p-methoxybenzyl ester), amides and hydrazides; for amino groups, carbamates (such as tert-butoxycarbonyl) and amides; for hydroxyl groups, ethers and esters; for thiol groups, thioethers and thioesters; for carbonyl groups, acetals and ketals; and the like. Such protecting groups are well-known to those skilled in the art and are described, for example, in T. W. Greene and G. M. Wuts, *Protecting Groups in Organic Synthesis*, Third Edition, Wiley, New York, 1999, and in P. J. Kocienski, *Protecting Groups*, Third Ed., Thieme Chemistry, 2003, and references cited therein.

A functional group in "protected form" refers to a functional group bearing a protecting group. As used herein, the term "functional group" or any synonym thereof is meant to encompass protected forms thereof.

"PEG" or "poly(ethylene glycol)" as used herein, is meant to encompass any water-soluble poly(ethylene oxide). Typically, PEGs for use in the present invention will comprise one of the two following structures: "—$(CH_2CH_2O)_n$—" or "—$(CH_2CH_2O)_{n-1}CH_2CH_2$—," depending upon whether or not the terminal oxygen(s) has been displaced, e.g., during a synthetic transformation, or, e.g., the identity of adjacent functional groups. The variable (n) typically ranges from 3 to about 3000, and the terminal groups and architecture of the overall PEG may vary. When PEG or a conjugate comprising a PEG segment further comprises a spacer or a linker as in Compound I above (to be described in greater detail below), the atoms comprising the spacer (X) or linker (O), when covalently attached to a PEG segment, do not result in formation of (i) an oxygen-oxygen bond (—O—O—, a peroxide linkage), or (ii) a nitrogen-oxygen bond (N—O, O—N). PEGs for use in the invention include PEGs having a variety of molecular weights, structures or geometries to be described in greater detail below.

"Water-soluble," in the context of a polymer of the invention or a "water-soluble polymer segment" is any segment or polymer that is soluble in water at room temperature. Typically, a water-soluble polymer or segment will transmit at least about 75%, more preferably at least about 95% of light, transmitted by the same solution after filtering. On a weight basis, a water-soluble polymer or segment thereof will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer or segment is about 95% (by weight) soluble in water or completely soluble in water.

An "end-capping" or "end-capped" group is an inert group present on a terminus of a polymer such as PEG. An end-capping group is one that does not readily undergo chemical transformation under typical synthetic reaction conditions. An end capping group is generally an alkoxy group, —OR, where R is an organic radical comprised of 1-20 carbons and is preferably lower alkyl (e.g., methyl, ethyl) or benzyl. For instance, an end capped PEG will typically comprise the structure "RO—$(CH_2CH_2O)_n$—", where R is as defined above. Alternatively, the end-capping group can also advantageously comprise a detectable label. When the polymer has an end-capping group comprising a detectable label, the amount or location of the polymer and/or the moiety (e.g., active agent) to which the polymer is coupled, can be determined by using a suitable detector. Such labels include, without limitation, fluorescers, chemiluminescers, moieties used in enzyme labeling, colorimetric (e.g., dyes), metal ions, radioactive moieties, and the like.

"Non-naturally occurring" with respect to a polymer means a polymer that in its entirety is not found in nature. A non-naturally occurring polymer may however contain one or more subunits or segments of subunits that are naturally occurring, so long as the overall polymer structure is not found in nature.

"Molecular mass" in the context of a water-soluble polymer such as PEG, refers to the nominal average molecular mass of a polymer, typically determined by size exclusion chromatography, light scattering techniques, or intrinsic viscosity determination in water or organic solvents. Molecular weight in the context of a water-soluble polymer, such as PEG, can be expressed as either a number-average molecular weight or a weight-average molecular weight. Unless otherwise indicated, all references to molecular weight herein refer to the number-average molecular weight. Both molecular weight determinations, number-average and weight-average, can be measured using gel permeation chromatographic techniques. Other methods for measuring molecular weight values can also be used, such as the use of end-group analysis or the measurement of colligative properties (e.g., freezing-point depression, boiling-point elevation, or osmotic pressure) to determine number-average molecular weight or the use of light scattering techniques, ultracentrifugation or viscometry to determine weight-average molecular weight. The polymers of the invention are typically polydisperse (i.e., number-average molecular weight and weight-average molecular weight of the polymers are not equal), possessing low polydispersity values such as less than about 1.2, less than about 1.15, less than about 1.10, less than about 1.05, and less than about 1.03. As used herein, references will at times be made to a single water-soluble polymer having either a weight-average molecular weight or number-average molecular weight; such references will be understood to mean that the single-water soluble polymer was obtained from a composition of water-soluble polymers having the stated molecular weight.

The term "linker" is used herein to refer to an atom or a collection of atoms used to link interconnecting moieties, such as an organic radical core and a polymer segment, $POLY_1$. A linker moiety may be hydrolytically stable or may include a physiologically hydrolyzable or enzymatically degradable linkage.

The term "spacer" is used herein to refer to an atom or a collection of atoms used to link interconnecting moieties, such as $POLY_1$ and a dimethylene group forming part of an alkanoate linkage to small molecule drug, D. A spacer moiety may be hydrolytically stable or may include a physiologically hydrolyzable or enzymatically degradable linkage.

A "hydrolysable" bond is a relatively weak bond that reacts with water (i.e., is hydrolyzed) under physiological conditions. The tendency of a bond to hydrolyze in water will depend not only on the general type of linkage connecting two central atoms but also on the substituents attached to these central atoms. Illustrative hydrolytically unstable linkages include carboxylate ester, phosphate ester, anhydrides, acetals, ketals, acyloxyalkyl ether, imines, orthoesters, peptides and oligonucleotides.

An "enzymatically degradable linkage" means a linkage that is subject to degradation by one or more enzymes. Such a linkage requires the action of one or more enzymes to effect degradation.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include but are not limited to the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Multi-armed" in reference to the geometry or overall structure of a polymer refers to polymer having 3 or more polymer-containing "arms" connected to a "core" molecule or structure. Thus, a multi-armed polymer may possess 3 polymer arms, 4 polymer arms, 5 polymer arms, 6 polymer arms, 7 polymer arms, 8 polymer arms or more, depending upon its configuration and core structure. One particular type of highly branched polymer is a dendritic polymer or dendrimer, that, for the purposes of the invention, is considered to possess a structure distinct from that of a multi-armed polymer. That is to say, a multi-armed polymer as referred to herein explicitly excludes dendrimers. Additionally, a multi-armed polymer as provided herein possesses a non-crosslinked core.

A "dendrimer" is a globular, size monodisperse polymer in which all bonds emerge radially from a central focal point or core with a regular branching pattern and with repeat units that each contribute a branch point. Dendrimers are typically formed using a nano-scale, multistep fabrication process. Each step results in a new "generation" that has two or more times the complexity of the previous generation. Dendrimers exhibit certain dendritic state properties such as core encapsulation, making them unique from other types of polymers.

"Branch point" refers to a bifurcation point comprising one or more atoms at which a polymer splits or branches from a linear structure into one or more additional polymer arms. A multi-arm polymer may have one branch point or multiple branch points, so long as the branches are not regular repeats resulting in a dendrimer.

"Substantially" or "essentially" means nearly totally or completely, for instance, 95% or greater of some given quantity.

"Alkyl" refers to a hydrocarbon chain, typically ranging from about 1 to 20 atoms in length. Such hydrocarbon chains are preferably but not necessarily saturated and may be branched or straight chain, although typically straight chain is preferred. Exemplary alkyl groups include methyl, ethyl, isopropyl, n-butyl, n-pentyl, 2-methyl-1-butyl, 3-pentyl, 3-methyl-3-pentyl, and the like. As used herein, "alkyl" includes cycloalkyl when three or more carbon atoms are referenced.

"Lower alkyl" refers to an alkyl group containing from 1 to 6 carbon atoms, and may be straight chain or branched, as exemplified by methyl, ethyl, n-butyl, i-butyl, t-butyl.

"Cycloalkyl" refers to a saturated or unsaturated cyclic hydrocarbon chain, including bridged, fused, or Spiro cyclic compounds, preferably made up of 3 to about 12 carbon atoms, more preferably 3 to about 8.

"Non-interfering substituents" are those groups that, when present in a molecule, are typically non-reactive with other functional groups contained within the molecule.

The term "substituted" as in, for example, "substituted alkyl," refers to a moiety (e.g., an alkyl group) substituted with one or more non-interfering substituents, such as, but not limited to: $C_3$-$C_8$ cycloalkyl, e.g., cyclopropyl, cyclobutyl, and the like; halo, e.g., fluoro, chloro, bromo, and iodo; cyano; alkoxy, lower phenyl; substituted phenyl; and the like. For substitutions on a phenyl ring, the substituents may be in any orientation (i.e., ortho, meta, or para).

"Alkoxy" refers to an —O—R group, wherein R is alkyl or substituted alkyl, preferably $C_1$-$C_{20}$ alkyl (e.g., methoxy, ethoxy, propyloxy, etc.), preferably $C_1$-$C_7$.

As used herein, "alkenyl" refers to a branched or unbranched hydrocarbon group of 1 to 15 atoms in length, containing at least one double bond, such as ethenyl(vinyl), 2-propen-1-yl(allyl), isopropenyl, 3-buten-1-yl, and the like.

The term "alkynyl" as used herein refers to a branched or unbranched hydrocarbon group of 2 to 15 atoms in length, containing at least one triple bond, ethynyl, 1-propynyl, 3-butyn-1-yl, 1-octyn-1-yl, and so forth.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably N, O, or S, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom which is not a carbon. Preferred heteroatoms include sulfur, oxygen, and nitrogen.

"Substituted heteroaryl" is heteroaryl having one or more non-interfering groups as substituents.

"Substituted heterocycle" is a heterocycle having one or more side chains formed from non-interfering substituents.

"Electrophile" refers to an ion, atom, or collection of atoms that may be ionic, having an electrophilic center, i.e., a center that is electron seeking, capable of reacting with a nucleophile.

"Nucleophile" refers to an ion or atom or collection of atoms that may be ionic, having a nucleophilic center, i.e., a center that is seeking an electrophilic center, and capable of reacting with an electrophile.

"Active agent" as used herein includes any agent, drug, compound, and the like which provides some pharmacologic, often beneficial, effect that can be demonstrated in vivo or in vitro. As used herein, these terms further include any physiologically or pharmacologically active substance that produces a localized or systemic effect in a patient.

"Pharmaceutically acceptable excipient" or "pharmaceutically acceptable carrier" refers to an excipient that can be included in the compositions of the invention and that causes no significant adverse toxicological effects to the patient.

"Pharmacologically effective amount," "physiologically effective amount," and "therapeutically effective amount" are used interchangeably herein to mean the amount of an active agent present in a pharmaceutical preparation that is needed to provide a desired level of active agent and/or conjugate in the bloodstream or in a target tissue or site in the body. The precise amount will depend upon numerous factors, e.g., the particular active agent, the components and physical characteristics of pharmaceutical preparation, intended patient population, patient considerations, and the like, and can readily be determined by one skilled in the art, based upon the information provided herein and available in the relevant literature.

"Multi-functional" in the context of a polymer of the invention means a polymer having 3 or more functional groups, where the functional groups may be the same or different, and are typically present on the polymer termini. Multi-functional polymers of the invention will typically contain from about 3-100 functional groups, or from 3-50 functional groups, or from 3-25 functional groups, or from 3-15 functional groups, or from 3 to 10 functional groups, i.e., contains 3, 4, 5, 6, 7, 8, 9 or 10 functional groups. Typically, in reference to a polymer precursor used to prepare a polymer conjugate of the invention, the polymer possesses 3 or more polymer arms having at the terminus of each arm a functional group suitable for coupling to an active agent moiety via a hydrolyzable ester linkage. Typically, such functional groups are the same.

"Difunctional" or "bifunctional" as used interchangeable herein means an entity such as a polymer having two functional groups contained therein, typically at the polymer termini. When the functional groups are the same, the entity is said to be homodifunctional or homobifunctional. When the functional groups are different, the polymer is said to be heterodifunctional or heterobifunctional.

A basic or acidic reactant described herein includes neutral, charged, and any corresponding salt forms thereof.

"Polyolefinic alcohol" refers to a polymer comprising an olefin polymer backbone, such as polyethylene, having multiple pendant hydroxyl groups attached to the polymer backbone. An exemplary polyolefinic alcohol is polyvinyl alcohol.

As used herein, "non-peptidic" refers to a polymer backbone substantially free of peptide linkages. However, the polymer may include a minor number of peptide linkages spaced along the repeat monomer subunits, such as, for example, no more than about 1 peptide linkage per about 50 monomer units.

The terms "subject," "individual" or "patient" are used interchangeably herein and refer to a vertebrate, preferably a mammal. Mammals include, but are not limited to, murines, rodents, simians, humans, farm animals, sport animals and pets. Such subjects are typically suffering from or prone to a condition that can be prevented or treated by administration of a polymer of the invention, typically but not necessarily in the form of a polymer-active agent conjugate as described herein.

The term "about," particularly in reference to a given quantity, is meant to encompass deviations of plus or minus five percent.

"Treatment" or "treating" of a particular condition includes: (1) preventing such a condition, i.e. causing the condition not to develop, or to occur with less intensity or to a lesser degree in a subject that may be exposed to or predisposed to the condition but does not yet experience or display the condition, (2) inhibiting the condition, i.e., arresting the development or reversing the condition.

"Optional" or "optionally" means that the subsequently described circumstance may or may not occur, so that the description includes instances where the circumstance occurs and instances where it does not.

A "small molecule" may be defined broadly as an organic, inorganic, or organometallic compound typically having a molecular weight of less than about 1000, preferably less than about 800 daltons. Small molecules of the invention encompass oligopeptides and other biomolecules having a molecular weight of less than about 1000.

A "residue," for example, of a small molecule (in reference to a conjugate as provided herein, refers to the portion or residue of the umodified small molecule up to the covalent linkage resulting from covalent attachment of the small molecule (or an activated or chemically modified form thereof) to a multi-armed polymer as provided herein. For example, upon hydrolysis of the hydrolyzable ester linkage between the small molecule moiety and the multi-armed polymer, the small molecule per se is released. For example, for a small molecule drug comprising a hydroxyl group and represented by the informal formula, D-OH, in reference to Compound I, the residue of the small molecule will correspond to "D," which is the portion of the small molecule remaining upon removal or replacement of the hydroxyl group, —OH. In reference to the organic core molecule, "R," the following example is provided. In the instance in which R is a residue of a molecule possessing three hydroxyls (a triol), represented as R—(OH)$_3$, when considered in reference to Compound I, then R—(O~) for each polymer arm, q, is considered as the residue of the polyol, where R is considered in combination with linker, Q, to be a residue of a triol. In the preceding example, oxygen (O) corresponds to linker, Q.

A "polyol" is an alcohol containing more than two hydroxyl groups, where the prefix "poly" in this instance refers to a plurality of a certain feature rather than to a polymeric structure. Similarly, a polythiol is a thiol containing more than two thiol (—SH) groups, and a polyamine is an amine containing more than two amino groups.

Multi-arm Polymer Conjugates—Neighboring Group Interactions and their Avoidance

The multi-armed polymer conjugates provided herein are also referred to as "prodrugs." The term "prodrug" refers, in the instant application, to a modified form of a drug, where such modification typically includes a covalent link between the drug and a chemical moiety (e.g., a polymer). A prodrug is converted in vivo to its active drug form, either enzymatically or nonenzymatically.

Multi-armed polymer conjugates of small molecules have been previously described. See, e.g., U.S. Patent Application Publication Nos. 2005/0112088 and 2007/0197575. Certain exemplified embodiments of the multi-armed polymer conjugates described therein contain an amino acid linker such as glycine connecting the active agent, e.g., a camptothecin molecule, to the multi-armed polymer scaffold. An amino acid linkage such as glycine is attractive due to its bifunctional nature and facile hydrolysis in vitro and in vivo. The ester linkage resulting from the amino acid linker is rapidly hydrolyzed due to the activation of the electron withdrawing nature of the functional group adjacent to the glycine moiety. However, although such a linker can provide advantageous hydrolysis rates, the inventors have discovered that a neighboring functional group interaction may cause problems under certain circumstances which may make such linkers sub-optimal in the final multi-arm polymer conjugates.

As a result of understanding how neighboring group processes occur (see, e.g., Capon and McManus, *Neighboring Group Participation*, Plenum Press, New York, 1975) and recognizing their potential occurrence, the inventors have fashioned (among other things) new conjugates, reagents, and synthetic schemes with this understanding in mind. Among other things, the present multi-armed polymer conjugates circumvent and/or reduce a neighboring group interaction that can result in azlactone formation—leading to less than optimal drug loading in the final multi-arm polymer drug conjugate. An azlactone is a compound that is an anhydride of an α-acylamino acid; the basic ring structure is the 5-oxazolone type, e.g.,

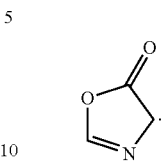

An azlactone can form, for example, in the presence of a condensing agent, when attempting to form an active ester of a carboxylic acid.

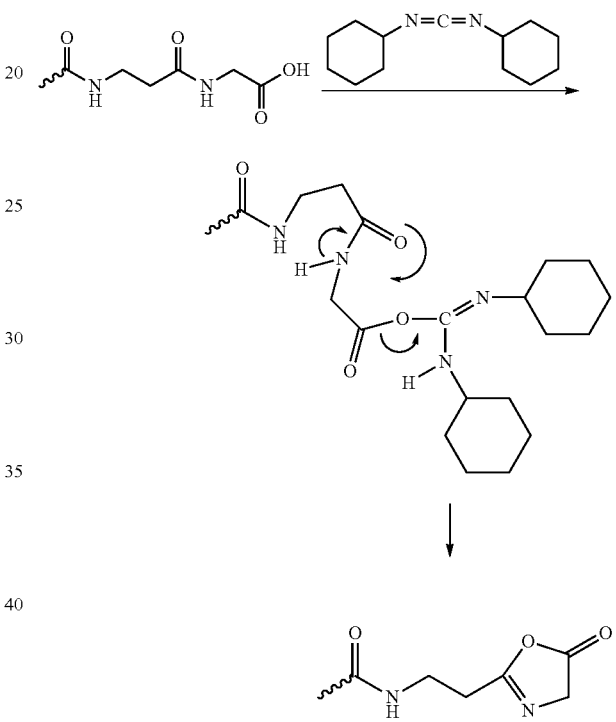

Azlactones can form in many similar processes. See, e.g., Benoiton et al. (1981) "*Oxazolones from 2-alkoxycarbonyl amino acids and their implication in carbodiimide-mediated reactions in peptide synthesis*" Can. J. Chem., 59:384. In considering the reaction above for forming an activated ester of a carboxylic acid, e.g., an N-hydroxysuccinimide ester, for example, if less than a stoichiometric amount of N-hydroxysuccinimide is used in the activation process, one would expect the dehydrating action of the carbodiimide to cause formation of the azlactone by the mechanism above. Additionally, since an N-hydroxysuccinimide ester is an activated form of the corresponding carboxylic acid, the azlactone can also form from the active ester via a mechanism similar to that for formation of the azlactone from the acid. Avoidance of azlactone formation, then, in forming desired products in good yields, and corresponding compositions substantially absent impurities such as substantially absent azlactone-containing impurities, is one nonlimiting aim of the conjugates, compositions and methods provided herein.

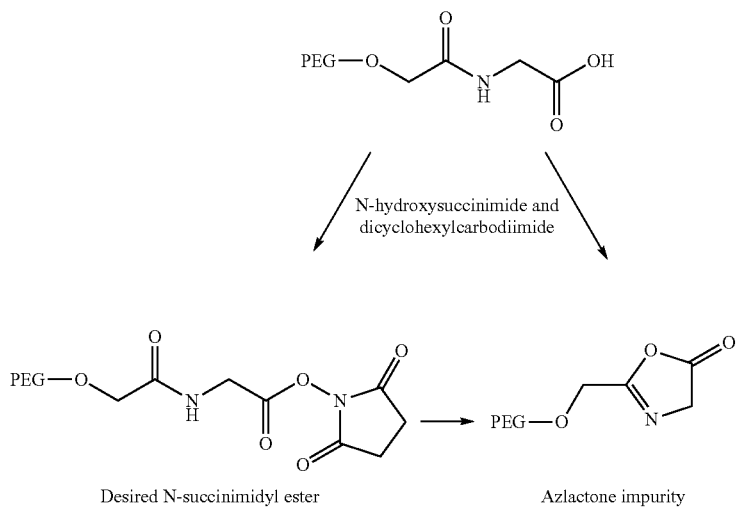

According to one or more embodiments of a multi-armed polymer prodrug in which drug is covalently attached to a multi-arm polymer via a glycine linker, as described in U.S. Patent Application Publication No. 2005/0112088, glycine is first conjugated to a drug containing a hydroxy group. Then, the glycine-derivatized drug is conjugated to an active (e.g., NHS) ester of carboxymethyl PEG (PEG CM), as illustrated in the scheme below.

Based upon the foregoing discussion, it can be seen that azlactone formation can occur during the step where a t-BOC-protected glycine is reacted with the drug alcohol. This is illustrated in the scheme below. Azlactone formation, even if formed in relatively minor amounts, can adversely impact the efficiency of that process and, at the same time produce a reactive impurity.

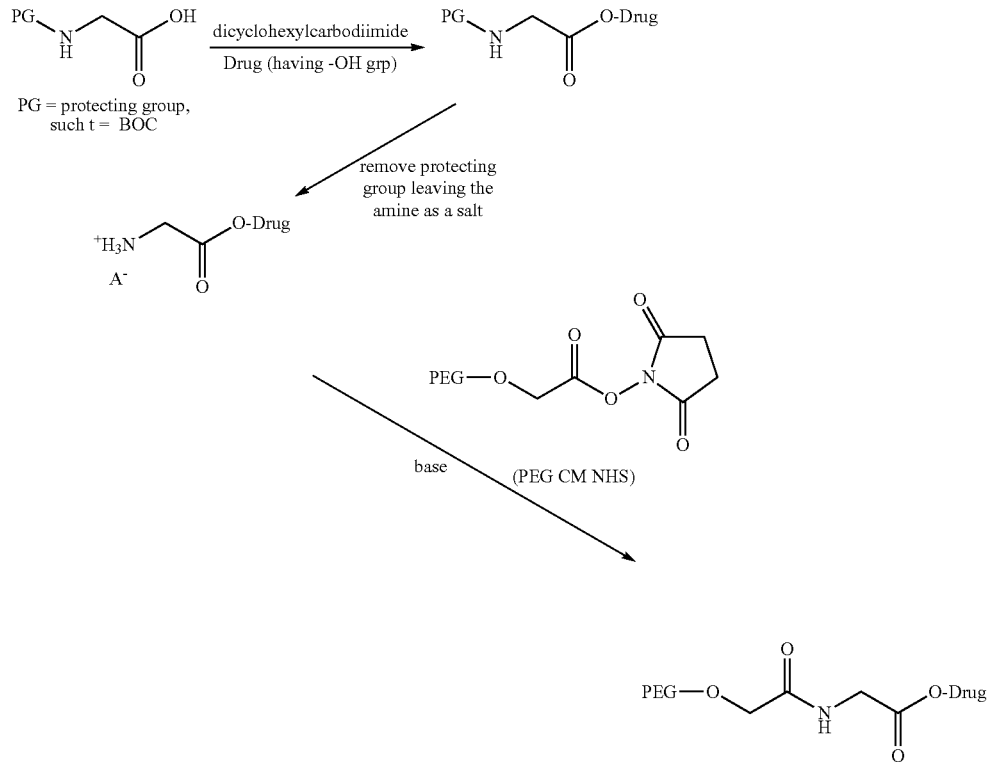

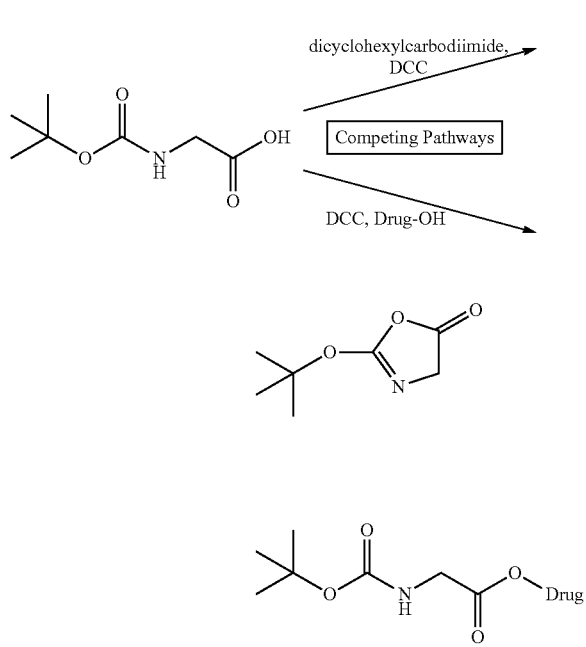

The foregoing discussion is relevant to the instant disclosure. During conjugation of various glycine-conjugated drug alcohol molecules, e.g., a camptothecin with a 4-arm-PEG-CM active ester, it was recognized that substitution of the end groups of the four-armed PEG polymer was suboptimal. Such substitution values (and less than optimal drug loading) although reproducible, resulted in a product which, on average, possessed fewer than all four polymer arms having drug conjugated thereto (i.e., a lower than ideal degree of substitution of drug upon the four-arm polymer). Ideally, a multi-arm polymer such as described herein will, on average, possess drug substituted on each of the polymer arms, so that the multi-arm polymer scaffold is "fully loaded"—to thereby take full advantage of the multi-arm feature of the polymer. See, e.g., Examples 3-5 in comparison to Examples 2, 6, 7, 8, 9, 10, and 12.

Substitution of a given polymer arm of a multi-arm polymer may result from a drug moiety never having become covalently attached to the polymer arm. In addition, substitution of a given polymer arm of a multi-arm polymer may result from loss of the drug moiety following ester formation. In this regard, a drug moiety, e.g. a camptothecin alcohol, acts as a leaving group and, in a way similar to the reaction shown with N-hydroxysuccinimide ester, is removed. An azlactone is likely to be an intermediate owing to the likely participation of the neighboring urethane group as illustrated below.

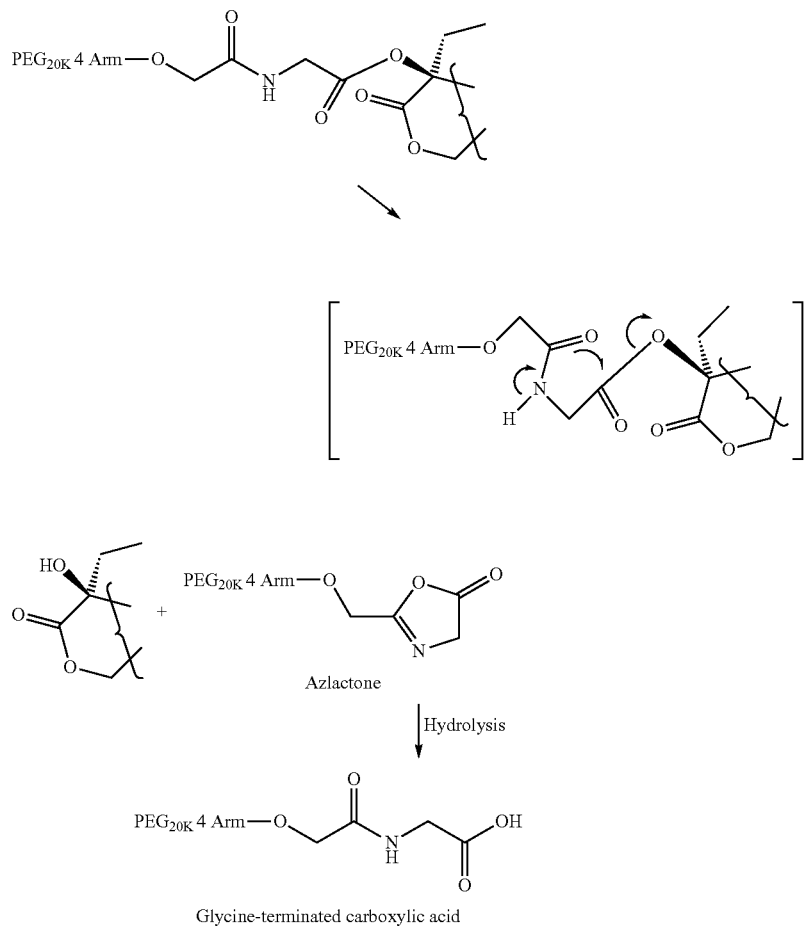

While N-hydroxysuccinimide is generally considered to be a much better leaving group than an alcohol (such as that present in, e.g., irinotecan or camptothecin), steric hindrance may be a driving force for this process in molecules that have a tertiary alcohol (e.g., irinotecan or camptotecin). The result, in the illustrated example, is that the terminating group is an azlactone or its hydrolysis product—the glycine-terminated PEG arm.

An azlactone, if formed, represents an impurity since it may react with amine groups of endogenous proteins to form unwanted conjugates in vivo. See U.S. Pat. No. 5,321,095.

It is believed that the conjugates, reagents, and methods described herein possess, among other things, the advantages of increased drug loading while avoiding impurities. In addition, the instant conjugates demonstate superior in-vivo anti-cancer activity, and reduced toxicity, along with an efficacy that is significantly enhanced over unconjuated drug alone.

The features of such conjugates will now be discussed in greater detail below.

Structural Features of the Polymer Conjugate

As described above, a conjugate as provided herein comprises a multi-arm polymer, i.e., having three or more arms, where the conjugate possesses the following generalized structure, Compound I

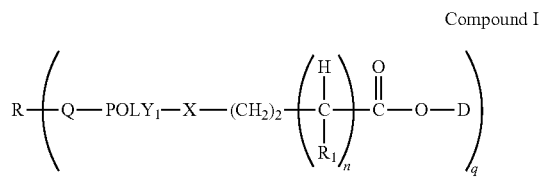

where: R is an organic core radical comprising from about 3 to about 150 carbon atoms; Q is a linker; $POLY_1$ is a water-soluble and non-peptidic polymer segment; X is a spacer that is optionally present; $R_1$, in each occurrence, is independently selected from the group consisting of H, lower alkyl, and an electron withdrawing group; n is an integer from 1 to 7; D is a residue of a small molecule, preferably a small molecule drug, having a molecular weight of less than about 800 daltons; and q is 3 or greater. Each arm of the multi-armed polymer is independent from the other. That is to say, each of the "q" arms of the multi-armed polymer may be composed of a different Q, $POLY_1$, X, $R_1$, n and so forth. Typical of such embodiments, a generalized structure corresponds to: R[(-$Q_1$-$POLY_{1A}$-$X_1$—$(CH_2)_2(CR_{1A}H)_{n1}C(O)$—O-$D_1$)(-$Q_2$-$POLY_{1B}$-$X_2$—$(CH_2)_2(CR_{1B}H)_{n2}C(O)$—O-$D_2$)(-$Q_3$-$POLY_{1C}$—$X_3$—$(CH_2)_2(CR_AH)_{n2}C(O)$—O-$D_3$) . . . ], and so forth for each of the arms emanating from the central organic core radical. Generally, however, each arm of the multi-armed prodrug is the same, with certain exceptions to be addressed in greater detail below.

As described in the preceding section, the multi-armed polymer contains the feature of an alkanoate segment, an alkanoate segment within the —X—$(CH_2)_2(CR_1H)_nC(O)$—O-D moiety. The alkanoate is of a length and nature sufficient to prevent or reduce neighboring group participation (e.g., from the linker group, "X"). An alpha or beta alkyl group or the like (e.g., when $R_1$ is alkyl) can offer value in providing steric hindrance to improve the selectivity of the ultimate active ester reagent. As can be seen in the supporting examples, use of the alkanoate linker is effective to result in exemplary multi-arm polymer drug conjugates having high drug loading efficiencies.

Each of the variable components of Compound I will now be described in detail. Each of the components described herein in relationship to the corresponding conjugate similarly extends to the corresponding multi-armed polymer reagent, e.g., where D as presented in Compound I as a residue of a small molecule, D can be substituted for, for example, H or a functional group corresponding to an activated ester.

Organic Core, "R"

In Compound I, R is an organic core radical possessing from about 3 to about 150 carbon atoms. Preferably, R contains from about 3 to about 50 carbon atoms, and even more preferably, R contains from about 3 to about 10 carbon atoms. That is to say, R, in one embodiment, may possess a number of carbon atoms selected from the group consisting of 3, 4, 5, 6, 7, 8, 9, and 10. The organic core may optionally contain one or more heteroatoms (e.g., O, S, or N), depending of course on the particular core molecule employed. R may be linear or cyclic, and typically, emanating therefrom are at least 3 independent polymer arms, at least one of which possesses an active agent moiety covalently attached thereto. Preferred organic core molecules are saturated aliphatics. Looking at Compound I, "q" corresponds to the number of polymer arms emanating from "R." In some instances one or more of the polymer arms may not have an active agent covalently attached thereto, but rather may have a relatively unreactive or unreacted functional group at its terminus, typically resulting from a synthesis that has failed to go to completion or due to hydrolysis. In this instance, D is absent and the individual structure of at least one of the polymer arms is in its precursor form (or is a derivative thereof), i.e., having at its terminus not an active agent, D, but rather, a functional group. However, one particularly advantageous feature of the multi-armed conjugates provided herein is their degree of drug loading on each of the water-soluble polymer arms of the multi-armed polymer. Preferably, due to the absence of any potential neighboring group interactions, the degree of drug loading of the multi-armed polymer (within a composition of multi-armed polymers) is greater than about 92%. For example, for a multi-armed polymer conjugate having q polymer arms, the average drug loading (within a composition of multi-armed polymers) will preferably be 0.92(q) or greater. Even more preferably, a multi-armed polymer conjugate as provided herein will possess a degree of drug loading (within a composition of multi-armed polymers) of at least 93%, 94%, 95%, 96%, 97%, 98% or even 99% or greater.

The central core organic radical, R, corresponds to a discrete molecule that provides a number of polymer attachment sites approximately equal to the desired number of water-soluble and non-peptidic polymer arms. Preferably, the central core molecule of the multi-arm polymer structure is the residue of a polyol, polythiol, or a polyamine bearing at least three hydroxyl, thiol, or amino groups available for polymer attachment. A "polyol" is a molecule comprising a plurality (3 or more) of available hydroxyl groups. A "polythiol" is a molecule that possesses a plurality (3 or more) thiol groups. A "polyamine" is a molecule comprising a plurality (3 or more) available amino groups. Depending on the desired number of polymer arms, the precursor polyol, polyamine or polythiol, (prior to covalent attachment of $POLY_1$) will typically contain 3 to about 25 hydroxyl, or amino groups or thiol groups, respectively, preferably from 3 to about 10 hydroxyl, amino groups or thiol groups, (i.e., 3, 4, 5, 6, 7, 8, 9, 10), most preferably, will contain from 3 to about 8 (e.g., 3, 4, 5, 6, 7, or 8) hydroxyl, amino groups or thiol groups suitable for covalent attachment of $POLY_1$. The polyol, polyamine or polythiol may also include other protected or unprotected functional groups. Focusing on organic cores derived from polyols or polyamines, although the number of intervening atoms between each hydroxyl or amino group will vary, preferred cores are those having a length of from about 1 to about 20 intervening core atoms, such as carbon atoms, between each hydroxyl or amino group, preferably from about 1 to about 5. In referring to intervening core atoms and lengths, —CH$_2$—, for example, is considered as having a length of one intervening atom, although the methylene group itself contains three atoms total, since the Hs are substituents on the carbon, and —CH$_2$CH$_2$—, for instance, is considered as having a length of two carbon atoms, etc. The particular polyol or polyamine precursor depends on the desired number of polymer arms in the final conjugate. For example, a polyol or polyamine core molecule having 4 functional groups, Q, is suitable for preparing a prodrug in accordance with Compound I having four polymer arms extending therefrom and covalently attached to active agent.

The precursor polyol or polyamine core will typically possess a structure R—(OH)$_p$ or R—(NH$_2$)$_p$ prior to functionalization with a polymer. The value of p corresponds to the value of q in Compound I, since each functional group, typically —OH or —NH$_2$, in the parent core organic molecule, if sterically accessible and reactive, is covalently attached to a polymer arm, POLY$_1$. Note that in Compound I, the variable "Q," when taken together with R, typically represents a residue of the core organic radical as described herein. That is to say, when describing preferred organic core molecules, particularly by name, the core molecules are described in their precursor form, rather than in their radical form after removal of, for example, a proton. So, if for example, the organic core radical is derived from pentaerythritol, the precursor polyol possesses the structure C(CH$_2$OH)$_4$, and the organic core radical, together with Q, corresponds to C(CH$_2$O—)$_4$, where Q is O. The core is non-crosslinked, and when taken together with POLY$_1$ excludes star-type polymers.

Illustrative polyols that are preferred for use as the polymer core include aliphatic polyols having from 1 to 10 carbon atoms and from 3 to 10 hydroxyl groups, including for example, trihydroxyalkanes, tetrahydroxyalkanes, polyhydroxy alkyl ethers, polyhydroxyalkyl polyethers, and the like. Cycloaliphatic polyols include straight chained or closed-ring sugars and sugar alcohols, such as mannitol, sorbitol, inositol, xylitol, quebrachitol, threitol, arabitol, erythritol, adonitol, dulcitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. Additional examples of aliphatic polyols include derivatives of glucose, ribose, mannose, galactose, and related stereoisomers. Aromatic polyols may also be used, such as 1,1,1-tris(4'-hydroxyphenyl)alkanes, such as 1,1,1-tris(4-hydroxyphenyl)ethane, 2,6-bis(hydroxyalkyl)cresols, and the like. Other core polyols that may be used include polyhydroxycrown ethers, cyclodextrins, dextrins and other carbohydrates (e.g., monosaccharides, oligosaccharides, and polysaccharides, starches and amylase).

Preferred polyols include glycerol, trimethylolpropane, pentaerythritol, dipentaerythritol, tripentaerythritol, ethoxylated forms of glycerol, trimethylolpropane, pentaerythritol, dipentaerythritol, tripentaerythritol. Also, preferred are reducing sugars such as sorbitol and glycerol oligomers, such as diglycerol, triglycerol, hexaglycerol and the like. A 21-arm polymer can be synthesized using hydroxypropyl-β-cyclodextrin, which has 21 available hydroxyl groups. Additionally, a polyglycerol having an average of 24 hydroxyl groups is commercially available.

Exemplary polyamines include aliphatic polyamines such as diethylene triamine, N,N',N''-trimethyldiethylene triamine, pentamethyl diethylene triamine, triethylene tetramine, tetraethylene pentamine, pentaethylene hexamine, dipropylene triamine, tripropylene tetramine, bis-(3-aminopropyl)-amine, bis-(3-aminopropyl)-methylamine, and N,N-dimethyl-dipropylene-triamine. Naturally occurring polyamines that can be used in the present invention include putrescine, spermidine, and spermine. Numerous suitable pentamines, tetramines, oligoamines, and pentamidine analogs suitable for use in the present invention are described in Bacchi et al. (2002) *Antimicrobial Agents and Chemotherapy*, 46(1):55-61, which is incorporated by reference herein.

Provided below are illustrative structures corresponding to the organic radical portion of the conjugate, R, and the corresponding idealized conjugate, assuming that each of the hydroxyls in the parent polyol has been transformed to a polymer arm and that each polymer arm has drug covalently attached thereto. Note that the organic radicals shown below, derived from polyols, include the oxygens, which, in the context of Compound I, for the arms that are polymer arms, are considered as Q. It is not necessary that all hydroxyls in, for example, a polyol-derived organic radical, form part of a polymer arm. In the illustrative examples below, Q is shown as O, but can equally be considered as corresponding to S, —NH—, or —NH—C(O)—. Additionally, the last two exemplary core structures illustrate two-polyol cores interconnected by a bifunctional linker such as the representative disulfide or dipeptide shown. Similar structures can be envisioned using any of the illustrative core molecules. See, e.g., International Patent Publication No. WO 2007/098466 for examples of additional multi-armed polymers suitable for preparing the multi-armed polymer alkanoate conjugates described herein, the contents of which is expressly incorporated herein by reference.

Organic Radical*/Illustrative Conjugate (*includes Q)

II

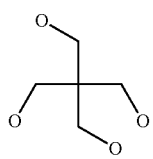

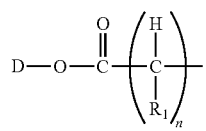 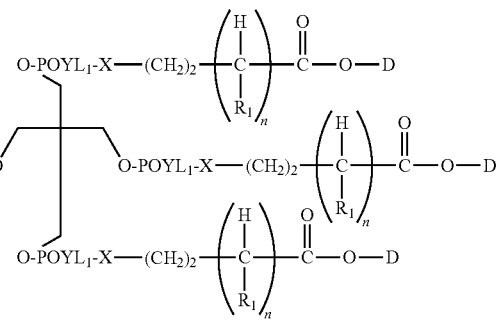
II-A
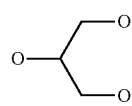
III
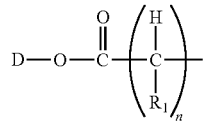
III-A
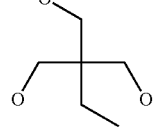
IV
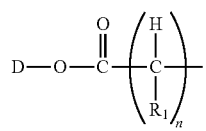 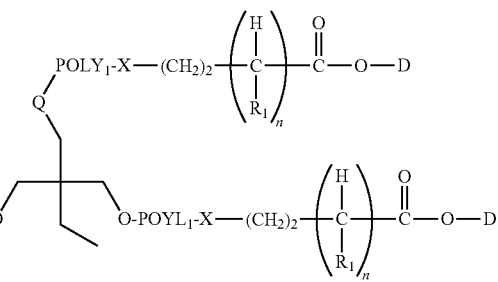
IV-A
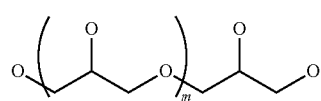
V
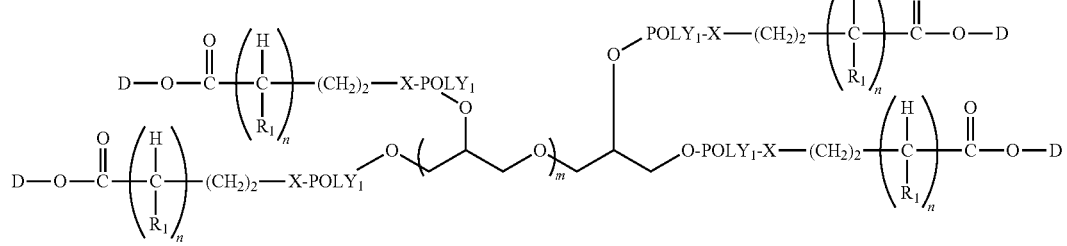
V-A
m=0-40, preferably 0-10, or 0-5 (e.g., 0, 1, 2, 3, 4, 5)

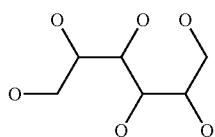
VI
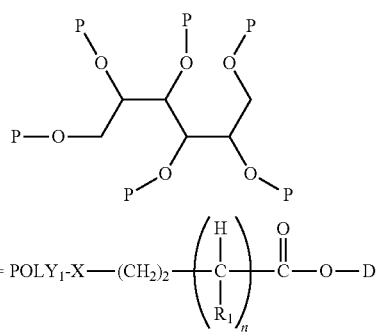
where P = POLY$_1$-X—(CH$_2$)$_2$—$\left(\underset{R_1}{\overset{H}{C}}\right)_n$—$\overset{O}{\underset{\|}{C}}$—O—D
VI-A
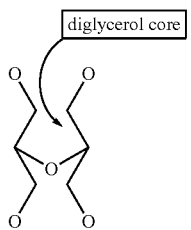
VII
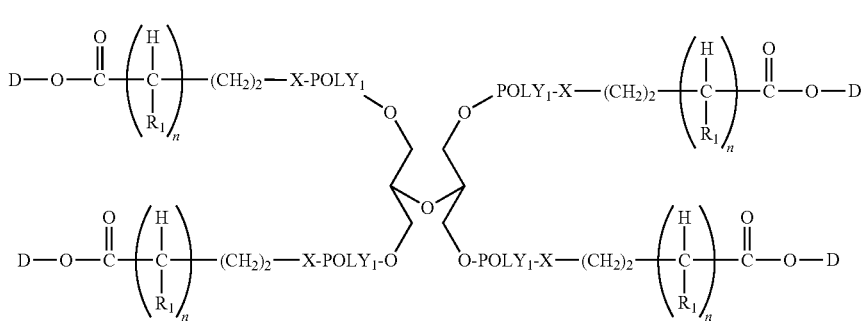
VII-A
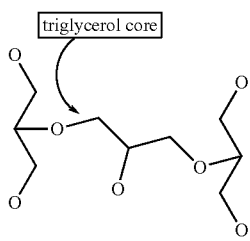
VIII
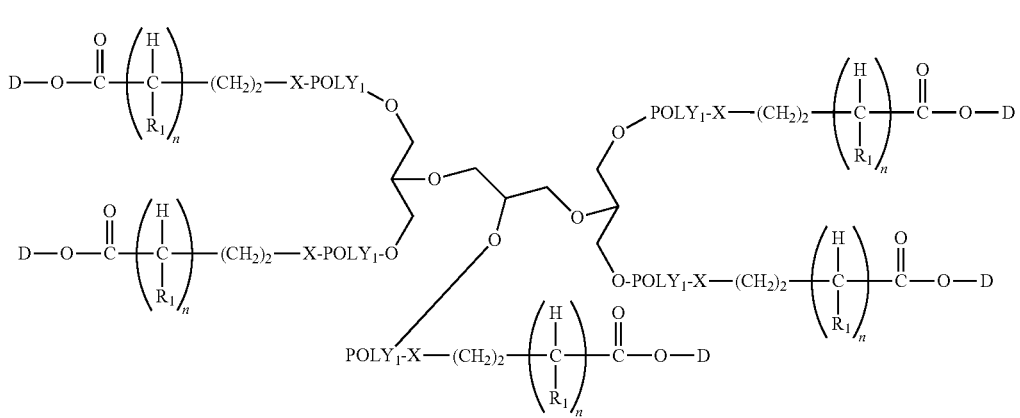
VIII-A -continued
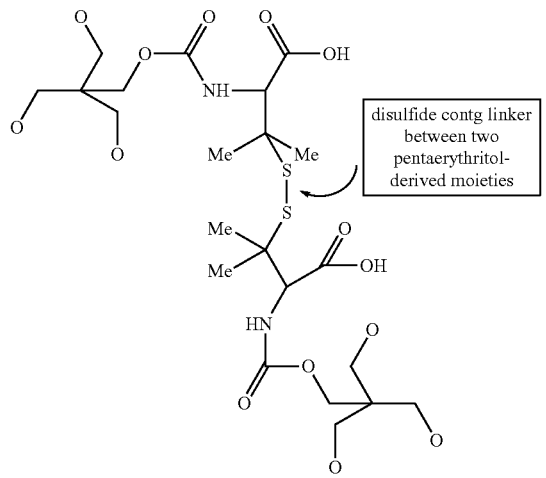
IX
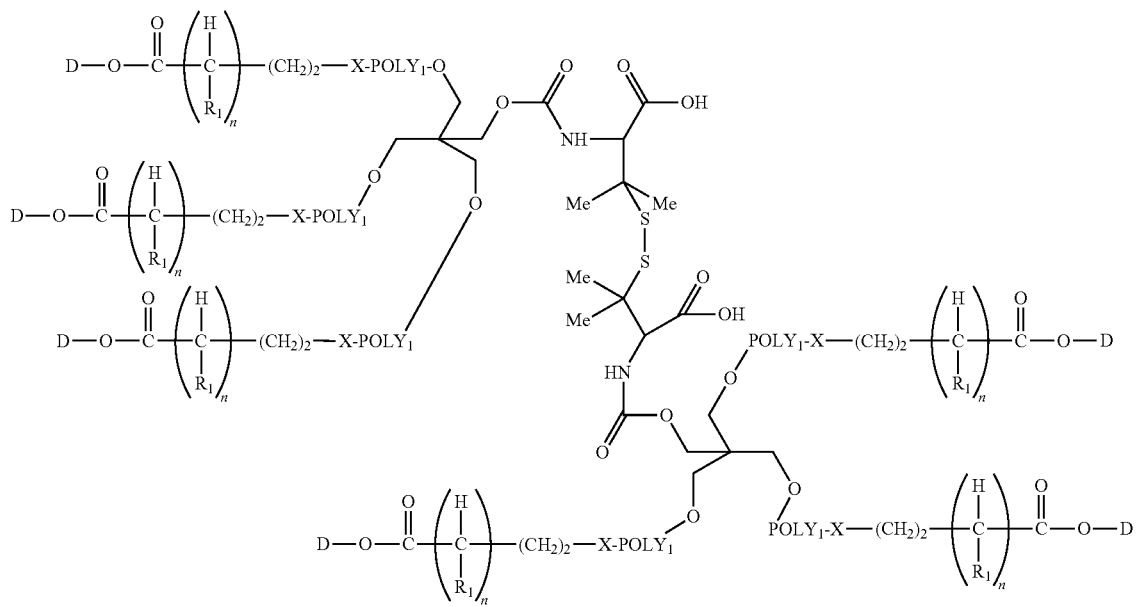
IX-A
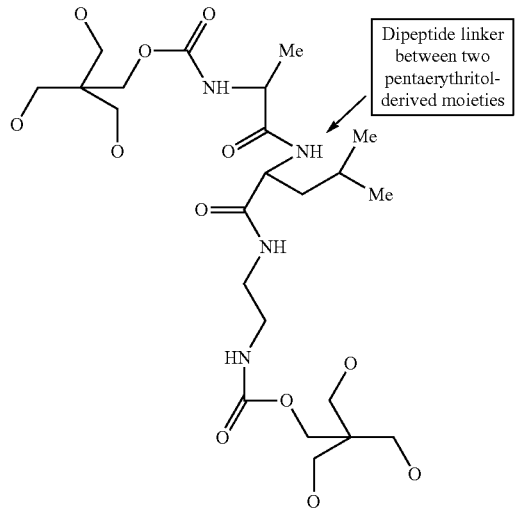
X

X-A

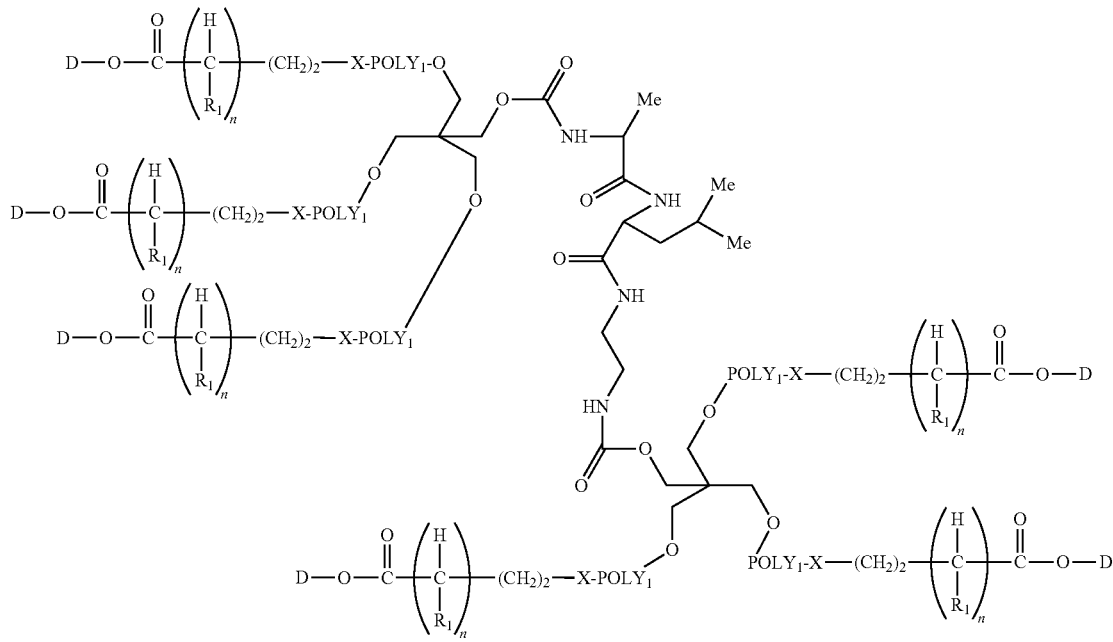

Additional multi-armed polymer starting materials suitable for preparing a multi-armed polymer alkanoate conjugate as described herein (corresponding to R-(Q-POLY$_1$~)$_q$ are available from, for example, NOF Corporation (Japan) through their catalogs, which are incorporated herein by reference.

Alternatively, a multi-armed polymer regent for preparing a multi-armed polymer drug may be synthetically prepared. For instance, any of a number of suitable polyol core materials can be purchased from a chemical supplier such as Aldrich (St. Louis, Mo.). Certain highly derivatized polyols are also available, e.g., a polyglycerol having an average of 24 hydroxyl groups, from Hyperpolymers GmbH. The terminal hydroxyls of the polyol are first converted to their anionic form, using, for example, a strong base, to provide a site suitable for initiating polymerization, followed by direct polymerization of monomer subunits, e.g., ethylene oxide, onto the core. Chain building is allowed to continue until a desired length of polymer chain is reached in each of the arms, followed by terminating the reaction, e.g., by quenching.

In yet another approach, an activated multi-armed polymer reagent can be synthetically prepared by first providing a desired polyol core material, and reacting the polyol under suitable conditions with a heterobifunctional PEG mesylate of a desired length, where the non-mesylate PEG terminus is optionally protected to prevent reaction with the polyol core. The resulting multi-armed polymer is then suitable for additional transformations or direct coupling to an active agent, following deprotection if necessary.

Multi-armed polymer reagents based on polyamino cores can be prepared, for example, by direct coupling to a polymer reagent activated with an acylating agent such as an NHS ester, a succinimidyl carbonate, a BTC ester or the like, to provide multi-armed polymer precursors having an amide linker, Q. Alternatively, a core molecule having multiple amino groups can be coupled with an aldehyde teiniinated polymer, such as a PEG, by reductive amination (using, for example, a reducing agent such as sodium cyanoborohydride) to provide a multi-armed polymer precursor having an internal amine linker, Q.

Figure 1B:
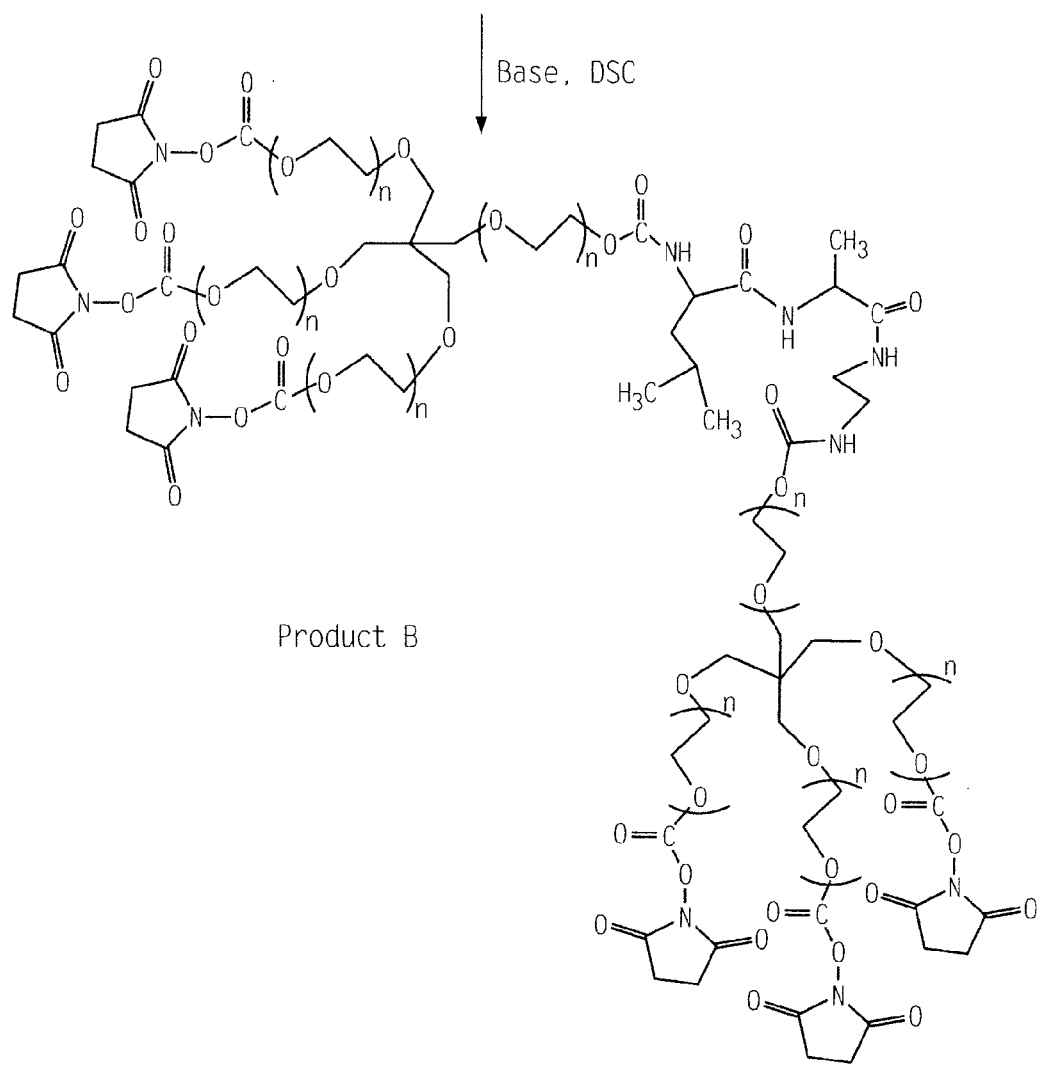
Figure 1C:
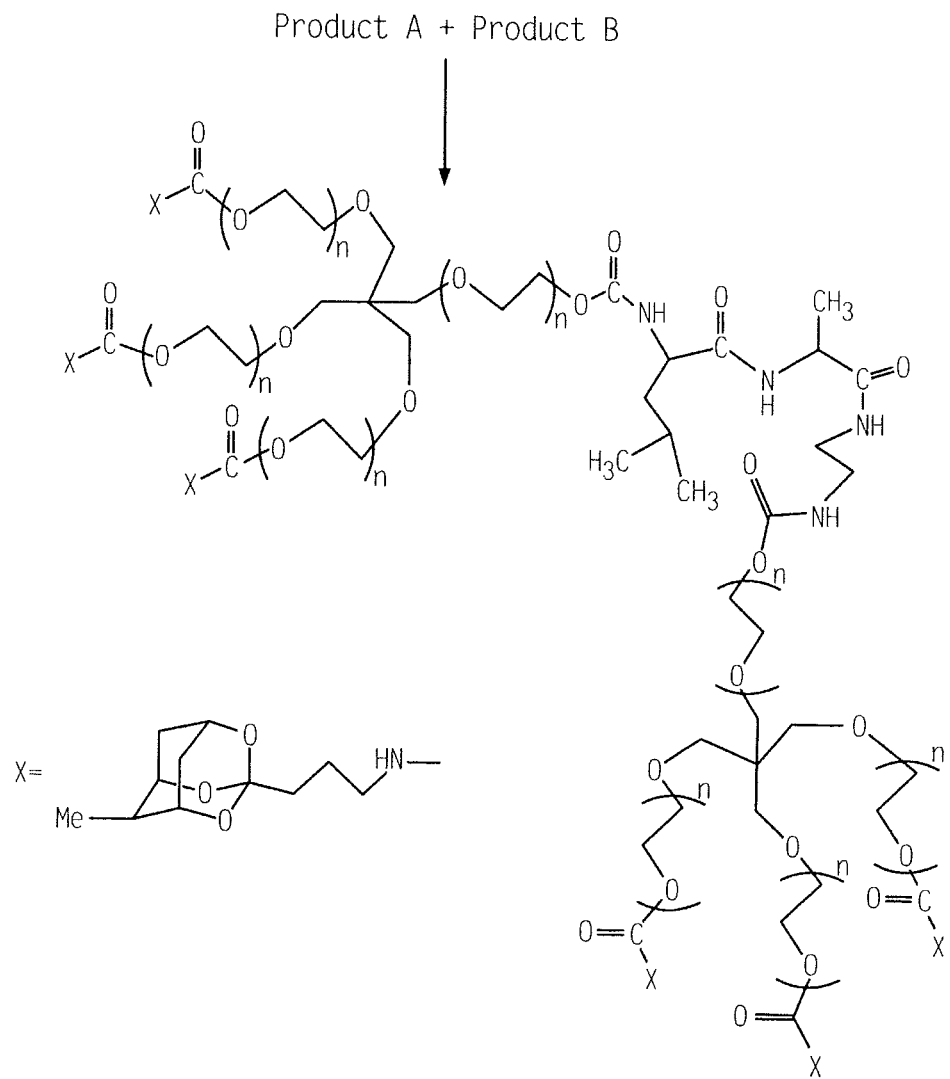

An illustrative synthesis of a dipeptide-linked pentaerythritolyl core-containing multi-armed polymer is provided herein as FIGS. 1A-1C.

Although the polymer, PEG, is described as a representative polymer in the synthetic descriptions above, such approaches apply equally as well to other water-soluble polymers described herein.

Linkages Q and X

The linkages between the organic radical, R, and the polymer segment, POLY$_1$, or between POLY$_1$ and the alkanoate moiety, result from the reaction of various reactive groups contained within R and POLY$_1$. Illustrative linking chemistry useful for preparing the polymer conjugates of the invention can be found, for example, in Wong, S. H., (1991), "Chemistry of Protein Conjugation and Crosslinking", CRC Press, Boca Raton, Fla. and in Brinkley, M. (1992) "A Brief Survey of Methods for Preparing Protein Conjugates with Dyes, Haptens, and Crosslinking Reagents", in Bioconjug. Chem., 3, 2013. The alkanoate portion of the multi-armed polymer conjugate provides a hydrolytically degradable bond (i.e., an ester linkage) to the small molecule active agent, so that the active agent is released over time from the multi-armed polymer core.

The multi-arm polymeric conjugates provided herein (as well as the corresponding reactive polymer precursor molecules, and so forth) comprise a linker segment, Q, and optionally, a spacer segment, X. Exemplary spacers or linkers can include segments such as those independently selected from the group consisting of —O—, —S—, —NH—, —C(O)—, —O—C(O)—, —C(O)—O—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—

CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —O—C(O)—NH—CH$_2$—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—C(O)—CH$_2$—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—NH—, —CH$_2$—CH$_2$—CH$_2$—C(O)—NH—CH$_2$—CH$_2$—NH—C(O)—, —CH$_2$—CH$_2$—CH$_2$—C(O)—NH—CH$_2$—CH$_2$—NH—C(O)—, —CH$_2$—NH—C(O)—CH$_2$—, —CH$_2$—CH$_2$—CH$_2$—C(O)—NH—CH$_2$—CH$_2$—NH—C(O)—CH$_2$—CH$_2$—, —O—C(O)—NH—[CH$_2$]$_{0-6}$—(OCH$_2$CH$_2$)$_{0-2}$—, —C(O)—NH—(CH$_2$)$_{1-6}$—NH—C(O)—, and —NH—C(O)—NH—(CH$_2$)$_{1-6}$—NH—C(O)—.

In any of the above examples, a simple cycloalkylene group, e.g. 1,3- or 1,4-cyclohexylene, may replace any two, three or four carbon alkylene group. For purposes of the present disclosure, however, a series of atoms is not a spacer moiety when the series of atoms is immediately adjacent to a water-soluble polymer segment and the series of atoms is but another monomer, such that the proposed spacer moiety would represent a mere extension of the polymer chain. A spacer or linker as described herein may also comprise a combination of any two or more of the above groups, in any orientation.

Referring to Compound I, Q is a linker, preferably one that is hydrolytically stable. Typically, Q contains at least one heteroatom such as O, or S, or NH, where the atom proximal to R in Q, when taken together with R, typically represents a residue of the core organic radical R. Generally, Q contains from 1 to about 10 atoms, or from 1 to about 5 atoms. Q typically contains one of the following numbers of atoms: 1, 2, 3, 4, 5, 6, 7, 8, 9, or 10. Illustrative and preferred Qs include O, S, —NH—, and —NH—C(O)—. Preferably, Q is oxygen, meaning that the organic core molecule is a polyol.

Again in reference to Compound I, X is a spacer that connects POLY$_1$ with the dimethylene group of the alkanoate segment. Generally speaking, the spacer has an atom length of from about 1 atom to about 50 atoms, or more preferably from about 1 atoms to about 25 atoms, or even more preferably from about 1 atom to about 10 atoms. Typically, the spacer is of an atom length selected from the group consisting of 1, 2, 3, 4, 5, 6, 7, 8, 9, or 10. When considering atom chain length, only atoms contributing to the overall distance are considered. For example, a spacer having the structure, —CH$_2$—C(O)—NH—CH$_2$CH$_2$O—CH$_2$CH$_2$O—C(O)—O— has a chain length of 11 atoms, since substituents are not considered to contribute significantly to the length of the spacer. Spacer X may be hydrolytically stable or hydrolytically degradable. In a particular embodiment, e.g., when POLY$_1$ is a polyethylene glycol, e.g., in several of the exemplary alkanoate conjugates and corresponding multi-arm polymer reagents provided in the accompanying Examples, X is oxygen. For instance, when POLY$_1$ corresponds to the structure —(CH$_2$CH$_2$O)$_n$CH$_2$CH$_2$—, X may correspond to oxygen or —O—, such that the final structure including the "X" oxygen, may, for simplification, appear in shorthand fashion as —(CH$_2$CH$_2$O)$_n$—.

In yet another embodiment, X possesses the structure: Y—Z, where Y is a spacer fragment covalently attached to Z, a hydrolytically degradable linkage. In certain embodiments, Z itself may not constitute a hydrolytically degradable linkage, however, when taken together with Y, or at least a portion of Y, forms a linkage that is hydrolytically degradable.

In yet a more particular embodiment of the spacer, X, Y has the structure: —(CR$_x$R$_y$)$_a$—K—(CR$_x$R$_y$)$_b$—(CH$_2$CH$_2$O)$_c$—, wherein each R$_x$ and R$_y$, in each occurrence, is independently H or an organic radical selected from the group consisting of alkyl, substituted alkyl, alkenyl, substituted alkenyl, alkynyl, substituted alkynyl, aryl, and substituted aryl, a ranges from 0 to 12 (i.e., can be 0, 1, 2, 3, 4, 5, 6, 7, 8, 9, 10, 11, or 12), b ranges from 0 to 12 (i.e., can be 0, 1, 2, 3, 4, 5, 6, 7, 8, 9, 10, 11, or 12), K is selected from —C(O)—, —C(O)NH—, —NH—C(O)—, —O—, —S—, O—C(O)—, C(O)—O—, O—C(O)—O—, O—C(O)—NH—, NH—C(O)—O—, c ranges from 0 to 25, and Z is selected from C(O)—O—, O—C(O)—O—, —O—C(O)—NH—, and NH—C(O)—O—. The particular structure of K and of Z will depend upon the values of each of a, b, and c, such that none of the following linkages result in the overall structure of spacer X: —O—O—, NH—O—, NH—NH—.

In yet another embodiment of the spacer, X, Y has the structure: —(CR$_x$R$_y$)$_a$—K—(CR$_x$R$_y$)$_b$—(CH$_2$CH$_2$NH)$_c$—, where the variables have the values previously described. In certain instances, the presence of the short ethylene oxide or ethyl amino fragments in spacer, X, can be useful in achieving good yields during preparation of the prodrug conjugate, since the presence of the linker can help to circumvent problems associated with steric hindrance, due to the multi-armed reactive polymer, the structure of the active agent, or a combination of both. Preferably, c is selected from the group consisting of 0, 1, 2, 3, 4, 5, 6, 7, 8, 9, and 10.

Preferably, R$_x$ and R$_y$ in each occurrence are independently H or lower alkyl. In one embodiment, R$_x$ and R$_y$ are in each occurrence H. In yet another embodiment, "a" ranges from 0 to 5, i.e., is selected from 0, 1, 2, 3, 4, or 5. In yet another embodiment, b ranges from 0 to 5, i.e., is selected from 0, 1, 2, 3, 4, or 5. In yet another embodiment, c ranges from 0 to 10. In yet another embodiment, K is —C(O)—NH. Any of the embodiments described herein is meant to apply not only to generalized Compound I, but also extend to particular combinations of embodiments.

Spacer X, when present, may also correspond to an amino acid, di- or tri-acid or the like, or a peptide or oligopeptide, in particular due to the presence of the alkanoate group which is sufficient to prevent any neighboring group interactions from occurring. Suitable amino acids include amino acids such as alanine, valine, leucine, isoleucine, glycine, threonine, serine, cysteine, methionine, tyrosine, phenylalanine, tryptophan, aspartic acid, glutamic acid, lysine, arginine, histidine, proline, and the like, as well as non-naturally occurring amino acids.

A preferred spacer, when present, is oxygen (—O—).

The Polymer, POLY1

In Compound I, $POLY_1$ represents a water-soluble and non-peptidic polymer. $POLY_1$ in each polymer arm of Compound I is independently selected, although preferably, each polymer arm will comprise the same polymer. That is to say, most preferably, each $POLY_1$ in each arm of the multi-armed polymer conjugate is the same. Preferably, each of the arms, i.e., each "(-Q-$POLY_1$-X-D)" of Compound I is also identical. Any of a variety of polymers that are non-peptidic and water-soluble can be used to form a conjugate in accordance with the present invention. Examples of suitable polymers include, but are not limited to, poly(alkylene glycols), copolymers of ethylene glycol and propylene glycol, poly(olefinic alcohol), poly(vinylpyrrolidone), poly(hydroxyalkylmethacrylamide), poly(hydroxyalkylmethacrylate), poly(saccharides), poly(α-hydroxy acid), poly(acrylic acid), poly(vinyl alcohol), polyphosphazene, polyoxazoline, poly(N-acryloylmorpholine), such as described in U.S. Pat. No. 5,629,384, which is incorporated by reference herein in its entirety, and copolymers, terpolymers, and mixtures of any one or more of the above.

Preferably, $POLY_1$ is a polyethylene glycol or PEG. $POLY_1$ can be in any of a number of geometries or forms, including linear chains, branched, forked, etc., although preferably $POLY_1$ is linear (i.e., in each arm of the overall multi-arm structure) or forked. A preferred structure for a multi-armed polymer prodrug having a "forked" polymer configuration is as follows:

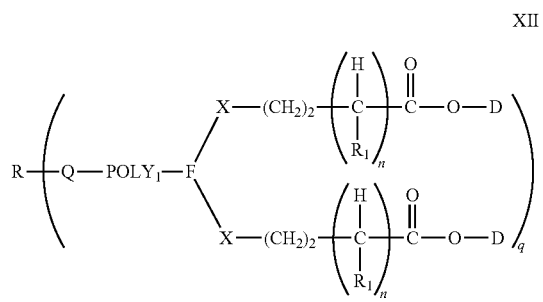

XII

F represents a forking group, and the remaining variables are as previously described. Preferably, the fork point in the forking group, F, comprises or is (—CH), although it may also be a nitrogen atom (N). In this way, each polymer arm is forked to possess two active agent moieties releasably covalently attached thereto, rather than one.

Illustrative forked polymers useful for preparing a multi-armed polymer of the type shown in structure XII are described in U.S. Pat. No. 6,362,254.

When $POLY_1$ is PEG, its structure typically comprises —$(CH_2CH_2O)_n$—, which may also be represented as —$(CH_2CH_2O)_nCH_2CH_2$—, where n may range from about 5 to about 400, preferably from about 10 to about 350, or from about 20 to about 300. In a preferred embodiment of the multi-armed polymer conjugates provided herein, $POLY_1$ is linear polyethylene glycol.

In the multi-arm embodiments described here, each polymer arm, $POLY_1$, typically has a molecular weight corresponding to one of the following: 200, 250, 300, 400, 500, 600, 700, 800, 900, 1000, 1500, 2000, 3000, 4000, 5000, 6000, 7000, 7500, 8000, 9000, 10000, 12,000, 15000, 17,500, 18,000, 19,000, 20,000 daltons or greater. Overall molecular weights for the multi-armed polymer configurations described herein (that is to say, the molecular weight of the multi-armed polymer as a whole) generally correspond to one of the following: 800, 1000, 1200, 1600, 2000, 2400, 2800, 3200, 3600, 4000, 5000, 6000, 8000, 10,000, 12,000, 15,000, 16,000, 20,000, 24,000, 25,000, 28,000, 30,000, 32,000, 36,000, 40,000, 45,000, 48,000, 50,000, 60,000, 80,000 or 100,000 or greater.

Typically, the overall molecular weight for a multi-armed polymer of the invention ranges from about 800 to about 80,000 daltons, or from about 900 to about 70,000 daltons. Other preferred molecular weight ranges for a multi-armed polymer of the invention are from about 1,000 to about 40,000 daltons, or from about 5,000 to about 30,000 daltons, or even from about 20,000 to about 80,000 daltons for higher molecular weight embodiments of the present conjugates.

The Alkanoate Segment

The multi-armed polymer conjugates provided herein comprise, in q polymer arms, an alkanoate segment. The alkanoate segment is provided to both conjugate to and then ultimately release the drug. Also, the alkanoate structure is designed to prevent the occurrence of possible neighboring group interactions that can lead to less than optimal drug loading and the formation of undesirable impurities in multi-armed polymer conjugate compositions. This is provided by both the length of the alkanoate segment and by the particular atoms and functional groups contained therein. Each of q polymer arms as illustrated in Compound I terminates in an alkanoate segment, in which the small molecule drug (or -hydrogen or active ester functionality) is covalently attached to the polymer arm via an ester linkage (forming part of the alkanoate). The alkanoate segment corresponds to: —$(CH_2)_2$—$(CHR_1)_n$C(O)—O-D, where $R_1$ is, in each occurrence, independently H, lower alkyl, alkylene, or an electron withdrawing group, and n is an integer from 1 to about 7. As can be seen from $R_1$, the carbon in the position alpha, beta, gamma, etc., to the carbonyl may be independently substituted, e.g., with a lower alkyl, alkylene, or electron withdrawing group. A substituent, such as a methyl or like group, in the alpha position, and to a lesser extent in the beta or gamma position, can provide steric hindrance to allow greater control or selectivity of the reagent, such that its reactivity with nucleophilic groups such as those present on drug molecules (e.g., alcohols, thiols) is diminished. Such a substituent may provide additional control of the hydrolytic stability of multi-armed conjugate. See, e.g., U.S. Pat. No. 6,495,659, the contents of which are incorporated herein by reference. Typically, the presence of an alkyl group at the alpha position will impart additional hydrolytic stability to the adjacent ester bond over that observed for such alkanoate absent such alkyl group.

$R_1$ may be, for example, H, or an alkyl group containing from 1 to about 6 carbon atoms. The lower alkyl group may be straight chain or branched, as exemplified by methyl, ethyl, propyl, i-propyl, n-butyl, i-butyl, sec-butyl, t-butyl, pentyl, i-pentyl, and the like. If an alkylene group is substituted on, e.g., the alpha position, and tied back to, e.g., the delta position, the structure has an alkanoate group that is cyclic in nature, as shown below.

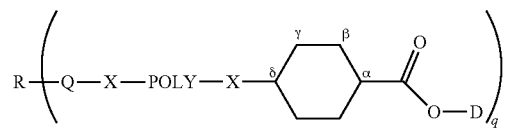

Alternatively, $R_1$ may be an electron withdrawing group (EWG) such as a halide (e.g., F, Cl, Br, or I), a nitrile, —$NO_2$, CF₃, —SO₃, or any other EWG commonly known in the art. The integer, n, typically has a value selected from 1, 2, 3, 4, 5, 6, and 7.

Thus, the portion —(CHR₁)ₙ— may correspond to any one of —CHR₁—, —CHR₁—CHR₁—, —CHR₁—CHR₁—CHR₁—CHR₁—CHR₁—CHR₁—, —CHR₁—CHR₁—CHR₁—CHR₁—CHR₁—CHR₁—CHR₁—CHR₁—CHR₁—CHR₁—CHR₁ where each R₁ in each chain is independently selected. In one particular embodiment, each R₁ in each of the foregoing, is hydrogen. In yet another embodiment, in each of the foregoing, each R₁ is hydrogen with the exception of the R₁ in the position alpha or adjacent to the carbonyl, in which case, this particular R₁ alone is lower alkyl. In yet an additional embodiment, in each of the foregoing structures, each R₁ is hydrogen with the exception of the R₁ in the position alpha or adjacent to the carbonyl, in which case, this particular R₁ alone is an EWG as described above.

Active Agent, D

Returning now to Compound I, D represents the residue of a small molecule active agent, and q (the number of polymer arms) ranges from about 3 to about 50. Illustrative ranges are from about 3 to about 10, from about 11 to about 25, from about 26 to 40, or from about 41 to about 50. Preferably, q ranges from about 3 to about 25. More preferably, q is from 3 to about 10, e.g., q possesses a value of 3, 4, 5, 6, 7, 8, 9, or 10. In a preferred embodiment, q is four. The active agent residue, D contains at least one hydroxyl functional group suitable for covalent attachment to the multi-armed polymer described herein to form a hydrolyzable ester linkage, such that upon hydrolysis, the active agent is released in its unmodified form.

In accordance with one embodiment of the invention, a multi-armed polymer conjugate is characterized as having from about 3 to about 25 active agent molecules covalently attached thereto. More particularly, the conjugate possesses 3, 4, 5, 6, 7, 8, 9, 10, 11, 12, 13, 14, 15, 16, 17, 18, 19, 20, 21, 22, 23, 24, or 25 active agent molecules covalently attached thereto. In a further embodiment, the conjugate of the invention has from about 3 to about 8 active agent molecules covalently attached to the water-soluble polymer. Typically, although not necessarily, the number of polymer arms will correspond to the number of active agents covalently attached to the water-soluble polymer. That is to say, in the case of a polymer having a certain number of polymer arms (e.g., q), each having a reactive alkanoate functional group at its terminus, the number of active agents covalently attached thereto in the resulting conjugate is most desirably q. In a preferred embodiment, a composition comprising the subject multi-armed polymer conjugate is characterized by a degree of drug loading of 92 percent or greater. That is to say, for a composition containing a multi-armed polymer conjugate having q polymer arms, the composition is characterized as having a drug loading on average per species of 0.92(q) or greater. That is to say, the composition is characterized by a drug loading on average per species satisfying or more of the following: 0.92(q) or greater; 0.93(q) or greater; 0.94(q) or greater; 0.95(q) or greater; 0.96(q) or greater; 0.97(q) or greater; 0.98(q) or greater; 0.99(q) or greater; and 1(q).

In yet another embodiment, rather than having multiple polymer arms emanating from a central organic radical core, a conjugate of the invention is characterized as a water-soluble polymer having pendant active agent moieties covalently attached thereto, each preferably covalently attached by a degradable linkage such as the alkanoate linkage described herein. In such an embodiment, the structure of the polymer prodrug conjugate is described generally as POLY₁(—X—(CH₂)₂(CR₁H)ₙC(O)—O-D)_q, where each drug residue is covalently attached to POLY₁ via the alkanoate linker, and the variables POLY₁, X, R₁, n, D, and q are as set forth above, and the polymer, typically a linear polymer, possesses "q" active agent residues attached thereto, typically at discrete lengths along the polymer chain, via spacer X, which is connected to the alkanoate linker-drug moiety.

In a specific embodiment, the active agent moiety or residue is a small molecule possessing a molecular weight of less than about 1000. In yet additional embodiments, the small molecule drug possesses a molecular weight of less than about 800, or even less than about 750. In yet another embodiment, the small molecule drug possesses a molecular weight of less than about 500 or, in some instances, even less than about 300.

Preferred active agent moieties are anticancer agents. Particularly preferred are oncolytics bearing at least one hydroxyl group (i.e., suitable for forming the alkanoate attachment). Particularly preferred are alkaloid cytotoxic agents such as the taxanes and camptothecins, as well as the vinca alkaloids vincristine, vinorelbine, vinblastine, and vidensine.

One preferred class of active agents is the camptothecins. In a preferred embodiment, D is a taxane or taxane derivative such as paclitaxel or docetaxel. For purposes of the present disclosure, the term "taxane" includes all compounds within the taxane family of terpenes. Thus, taxol (paclitaxel), 3'-substituted tert-butoxy-carbonyl-amine derivatives (taxoteres) and the like as well as other analogs available from, for example, Sigma-Aldrich, are within the scope of the present disclosure. One particularly preferred D is docetaxel, where the H at the 2' position is absent in the final multi-armed polymer conjugate:

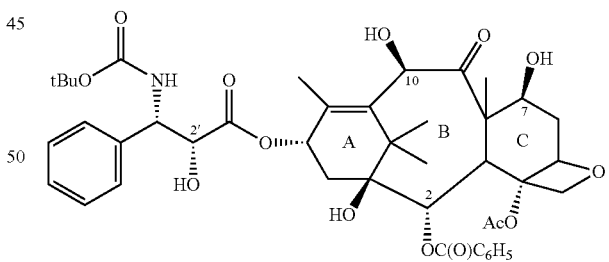

Other preferred taxanes are those capable of undergoing modification at the 2' position of the taxane skeleton, such as described herein in certain embodiments and in the accompanying examples.

Additionally, within the scope of the disclosure are taxanes such as docetaxel, where attachment to the multi-armed alkanoate scaffold may be at any —OH position within the taxane skeleton.

Yet another preferred class of active agents is the camptothecins. In one embodiment, a camptothecin for use in the invention corresponds to the structure,

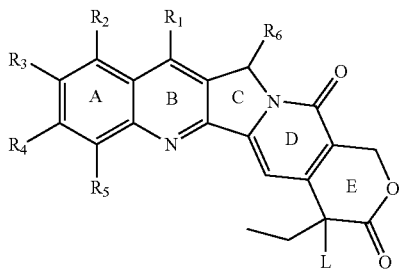

XIII wherein:

$R_1$-$R_5$ are each independently selected from the group consisting of hydrogen; halo; acyl; alkyl (e.g., C1-C6 alkyl); substituted alkyl; alkoxy (e.g., C1-C6 alkoxy); substituted alkoxy; alkenyl; alkynyl; cycloalkyl; hydroxyl; cyano; nitro; azido; amido; hydrazine; amino; substituted amino (e.g., monoalkylamino and dialkylamino); hydroxcarbonyl; alkoxycarbonyl; alkylcarbonyloxy; alkylcarbonylamino; carbamoyloxy; arylsulfonyloxy; alkylsulfonyloxy; —C($R_7$)=N—(O)$_i$—$R_8$ wherein $R_7$ is H, alkyl, alkenyl, cycloalkyl, or aryl, i is 0 or 1, and $R_8$ is H, alkyl, alkenyl, cycloalkyl, or heterocycle; and $R_9$C(O)O— wherein $R_9$ is halogen, amino, substituted amino, heterocycle, substituted heterocycle, or $R_{10}$—O—(CH$_2$)$_m$— where m is an integer of 1-10 and $R_{10}$ is alkyl, phenyl, substituted phenyl, cycloalkyl, substituted cycloalkyl, heterocycle, or substituted heterocycle; or $R_2$ together with $R_3$ or $R_3$ together with $R_4$ form substituted or unsubstituted methylenedioxy, ethylenedioxy, or ethyleneoxy;

$R_6$ is H or OR', wherein R' is alkyl, alkenyl, cycloalkyl, haloalkyl, or hydroxyalkyl; and L is the site of attachment to the multi-armed polymer conjugate.

Although L is shown at the 20 ring position above, the site of attachment may be at any suitable position within the camptothecin structure.

The term "camptothecin compound" as used herein includes the plant alkaloid 20(S)-camptothecin, as well as pharmaceutically active derivatives, analogues and metabolites thereof. Examples of camptothecin derivatives include, but are not limited to, 9-nitro-20(S)-camptothecin, 9-amino-20(S)-camptothecin, 9-methyl-camptothecin, 9-chloro-camptothecin, 9-fluoro-camptothecin, 7-ethyl camptothecin, 10-methyl-camptothecin, 10-chloro-camptothecin, 10-bromo-camptothecin, 10-fluoro-camptothecin, 9-methoxy-camptothecin, 11-fluoro-camptothecin, 7-ethyl-10-hydroxy camptothecin (SN38), 10,11-methylenedioxy camptothecin, and 10,11-ethylenedioxy camptothecin, and 7-(4-methylpiperazinomethylene)-10,11-methylenedioxy camptothecin, 7-ethyl-10-(4-(1-piperidino)-1-piperidino)-carbonyloxy-camptothecin, 9-hydroxy-camptothecin, and 11-hydroxy-camptothecin. Particularly preferred camptothecin compounds include camptothecin, irinotecan, and topotecan.

Native and unsubstituted, the plant alkaloid camptothecin can be obtained by purification of the natural extract, or may be obtained from the Stehlin Foundation for Cancer Research (Houston, Tex.). Substituted camptothecins can be obtained using methods known in the literature or can be obtained from commercial suppliers. For example, 9-nitro-camptothecin may be obtained from SuperGen, Inc. (San Ramon, Calif.), and 9-amino-camptothecin may be obtained from Idec Pharmaceuticals (San Diego, Calif.). Camptothecin and various analogues and derivatives may also be obtained from standard fine chemical supply houses, such as Sigma Chemicals.

Certain preferred camptothecin compounds correspond to the generalized structure below

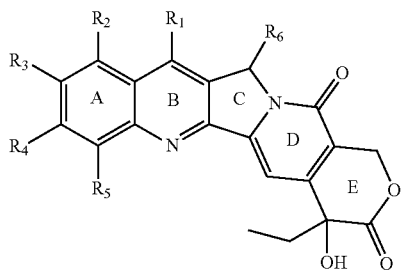

XI wherein:

$R_1$-$R_5$ are each independently selected from the group consisting of hydrogen; halo; acyl; alkyl (e.g., C1-C6 alkyl); substituted alkyl; alkoxy (e.g., C1-C6 alkoxy); substituted alkoxy; alkenyl; alkynyl; cycloalkyl; hydroxyl; cyano; nitro; azido; amido; hydrazine; amino; substituted amino (e.g., monoalkylamino and dialkylamino); hydroxcarbonyl; alkoxycarbonyl; alkylcarbonyloxy; alkylcarbonylamino; carbamoyloxy; arylsulfonyloxy; alkylsulfonyloxy; —C($R_7$)=N—(O)$_i$—$R_8$ wherein $R_7$ is H, alkyl, alkenyl, cycloalkyl, or aryl, i is 0 or 1, and $R_8$ is H, alkyl, alkenyl, cycloalkyl, or heterocycle; and $R_9$C(O)O— wherein $R_9$ is halogen, amino, substituted amino, heterocycle, substituted heterocycle, or $R_{10}$—O—(CH$_2$)$_m$— where m is an integer of 1-10 and $R_{10}$ is alkyl, phenyl, substituted phenyl, cycloalkyl, substituted cycloalkyl, heterocycle, or substituted heterocycle; or $R_2$ together with $R_3$ or $R_3$ together with $R_4$ form substituted or unsubstituted methylenedioxy, ethylenedioxy, or ethyleneoxy; and $R_6$ is H or OR', wherein R' is alkyl, alkenyl, cycloalkyl, haloalkyl, or hydroxyalkyl.

Exemplary substituting groups include hydroxyl, amino, substituted amino, halo, alkoxy, alkyl, cyano, nitro, hydroxycarbonyl, alkoxycarbonyl, alkylcarbonyloxy, alkylcarbonylamino, aryl (e.g., phenyl), heterocycle, and glycosyl groups.

For example, in embodiment, D is irinotecan, where the H on the 20-position hydroxyl is absent in the final multi-armed prodrug conjugate.

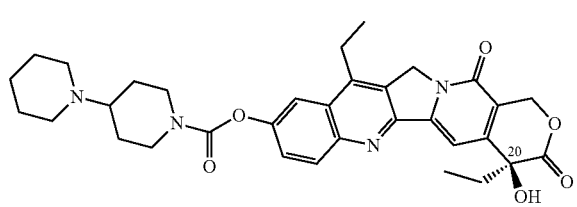 [SMILES: CCc1c2c(nc3ccc(OC(=O)N4CCC(N5CCCCC5)CC4)cc13)-c1cc3c(c(=O)n1C2)COC(=O)[C@]3(O)CC]

Alternatively, D is SN-38.

More particularly, the active agent may fall into one of a number of structural classes, including but not limited to small molecules, oligopeptides, polypeptides or protein mimetics, fragments, or analogues, steroids, nucleotides, oligonucleotides, electrolytes, and the like, and typically contains as least one free hydroxyl group, or the like (i.e., "handle") suitable for covalent attachment to the multi-armed polymer.

Alternatively, the drug is modified by introduction of a suitable "handle," preferably by conversion of one of its existing functional groups to a functional group suitable for formation of the herein described alkanoate linkage. Ideally, such a modification should not adversely impact the therapeutic effect or activity of the active agent to a significant degree. That is to say, any modification of an active agent to facilitate its attachment to a multi-armed polymer of the invention should result in no greater than about a 30% reduction of its bioactivity relative to the known parent active agent prior to modification. More preferably, any modification of an active agent to facilitate its attachment to a multi-armed polymer of the invention preferably results in a reduction of its activity relative to the known parent active agent prior to modification of no greater than about 25%, 20%, 15%, 10% or 5%.

The above exemplary drugs are meant to encompass, where applicable, analogues, agonists, antagonists, inhibitors, isomers, polymorphs, and pharmaceutically acceptable salt forms thereof.

Compositions/populations of prodrug conjugates

As stated above, in certain instances, a composition comprising a multi-arm polymer conjugate as described herein may contain a species of the prodrug having one or more of its polymer arms absent drug, D. Such an occurrence may arise, for example, due to incomplete reaction of the multi-armed reactive polymer with drug, D. Often, even in the instance of favorable stoichiometry, i.e., using an excess of drug relative to the number of reactive polymer arms, it can be difficult to drive the reaction to completion such that the product may comprise a mixture polymer species. However, by way of employing the present alkanoate linker, when characterizing a multi-armed polymer prodrug composition as provided herein, the degree (i.e., percentage) of drug loading for the final conjugate is advantageously high, typically at 92% or greater, e.g., from about 92% to 100% loading.

However, for the sake of completeness, it should be noted that a composition of the invention may, in certain instances, comprise a multi-arm polymer conjugate generally characterized as $R(-Q_1-POLY_1-X_1-(CH_2)_2(CR_1H)_nC(O)-O-D)_q$, where one or more polymer arms are absent drug. Assuming that each arm of the starting multi-armed polymer reagent has an alkanoic acid function attached thereto, the resulting conjugate may, and preferably will, possess drug covalently attached to each polymer arm, or alternatively, may lack drug, D. The variable D is a small molecule, where $D_1$ indicates the presence of D and $D_0$ indicates its absence. So, for example, a composition may comprise: $R(-Q-POLY_1-X-(CH_2)_2(CR_1H)_nC(O)-O-D)_m(-Q-POLY_1-X-(CH_2)_2(CR_1H)_nC(O)-O-D_0)_s$, where m+s=q, the only caveat being that m (the number of polymer arms having drug attached) is 1 or greater (e.g., from 1 to q). The value of m will correspondingly range from 0 to (q−1). Typically, when drug is absent, i.e., is $D_0$, the polymer arm will terminate in functional group, Y, where Y is –H or a derivative (reaction product) of the corresponding alkanoic acid or activated carboxysuccinimide. More specifically, a composition of the invention may comprise one or more multi-armed polymer conjugate species having the structure: $R(-Q-POLY_1-X-(CH_2)_2(CR_1H)_nC(O)-O-D)_m(-Q-POLY_1-X-(CH_2)_2(CR_1H)_nC(O)-O-Y)_s$, where Y corresponds to H or a derivative of the corresponding alkanoic acid or activated carboxysuccinimide. Preferred compositions are those in which, when characterized overall, possess a value of m that is 0.92(q) or greater. Ideally, in the instance of quantitative substitution of active agent, s equals zero and m equals q.

As an illustration, in an instance in which the multi-armed polymer conjugate contains four polymer arms, the idealized value of the number of covalently attached drug molecules per multi-armed polymer is four, and an average number of drug molecules per multi-armed polymer ranges from about 92% to about 100% of the idealized value. This corresponds to an average number of D per multi-arm polymer conjugate ranging from about 3.68 to 4.0.

In yet another embodiment, for a multi-aimed polymer conjugate composition, e.g., where the number of polymer arms ranges from about 3 to about 8, the majority species present in the composition are those having either an idealized number of drug molecules attached to the polymer core ("q") or those having a combination of ("q") and ("q−1") drug molecules attached to the polymer core.

For example, a preferred multi-armed polymer prodrug composition in accordance with the invention may comprise one or more of the following conjugate species:

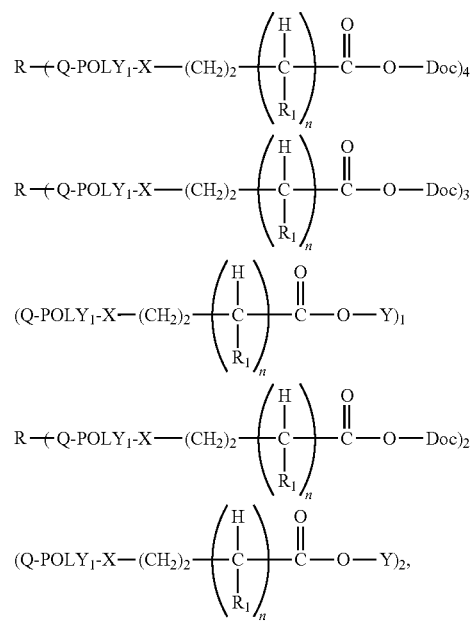

and so forth, where O-Doc corresponds to:

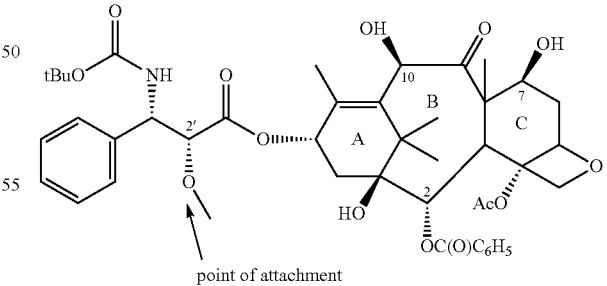

and preferably predominantly comprises the first species, that is, where each polymer arm has drug, in this case, docetaxel, covalently attached thereto. That is to say, most preferably, a multi-arm polymer conjugate as provided herein possesses active agent covalently attached to each polymer arm, such that essentially quantitative substitution of active agent in each of the polymer arms has taken place. In such an embodiment, a composition of the invention is characterized by having an average number of drug molecules per multi-armed polymer that corresponds essentially to its idealized value (i.e., is essentially 100% of its idealized value).

This disclosure is meant to encompass each prodrug species described herein, whether described singly or as forming part of a prodrug composition.

One exemplary and preferred conjugate is described in Example 2, 4-ARM-PEG$_{20K}$-BA-DOC. That is to say, in a preferred embodiment, a multi-armed polymer conjugate as provided herein possesses a pentaerythritol-derived core (such that R-Q-corresponds to pentaerythritolyl), a POLY$_1$ that corresponds to PEG, —(CH$_2$CH$_2$O)$_n$CH$_2$CH$_2$—, a value of X that corresponds to oxygen, O, and an alkanoate linker portion that corresponds to butanoate, such that n=1, R$_1$=H, and q equals 4. As described in Example 2, the substitution value for the four-armed polymer conjugate was approximately 98-100%. Additional characterization of extent of drug loading is provided in Example 11 (see, e.g., Table 1). As can be seen from the comparative data provided in Example 11, average drug loading values for glycine-linked and carboxymethylene-linked multi-armed conjugates were significantly lower, averaging from about 75% to about 80% of their idealized values, indicating the value of the instant alkanoate-linked multi-armed polymer conjugates and their improvement over earlier described multi-armed polymer conjugates.

The preparation of additional exemplary multi-armed polymer conjugates having an alkanoate linker is described in Example 12. Such conjugates possess the following features: a pentaerythritolyl core (e.g., where R-Q corresponds to pentaerythritolyl), a water-soluble and non-peptidic polymer segment, POLY), that is PEG, —(CH$_2$CH$_2$O)$_n$CH$_2$CH$_2$—, a spacer, X, that is oxygen, a value of q that equals 4, and the following alkanoate linkers: α-methylpropanoate, α-methylpentanoate, hexanoate, octanoate, and decanoate.

Method of Forming a Multi-armed Polymer Prodrug Conjugate

Multi-armed reactive polymers, such as those for preparing a conjugate of the invention can be readily prepared from commercially available starting materials in view of the guidance presented herein, coupled with what is known in the art of chemical synthesis.

Hydroxyl-terminated multi-armed PEGs having either a pentaerythritol core or a glycerol core are available from NOF Corporation. Such multi-armed PEGs can be used directly for preparing the conjugates provided herein, by functionalization to prepare the corresponding alkanoic acids for coupling to hydroxyls present on an active agent. See, e.g., Example 1, which describes formation of 4-ARM-PEG-Butanoic Acid, followed by conjugation as described in Example 2. In the approach described, the multi-arm 4-ARM-PEG-OH starting material is reacted with a protected bromobutanoic acid in the presence of a strong base to form the desired multi-armed PEG alkanoic acid reagent. See, e.g., U.S. Patent Application Publication No. US 2005/0036978. This approach is applicable to the preparation of any multi-armed PEG-OH starting material. The resulting multi-armed polymer alkanoic acid can be coupled to the target hydroxyl-containing drug, e.g., using a suitable condensing agent such as diisopropylcarbodiimide (DIC). This is shown schematically below,

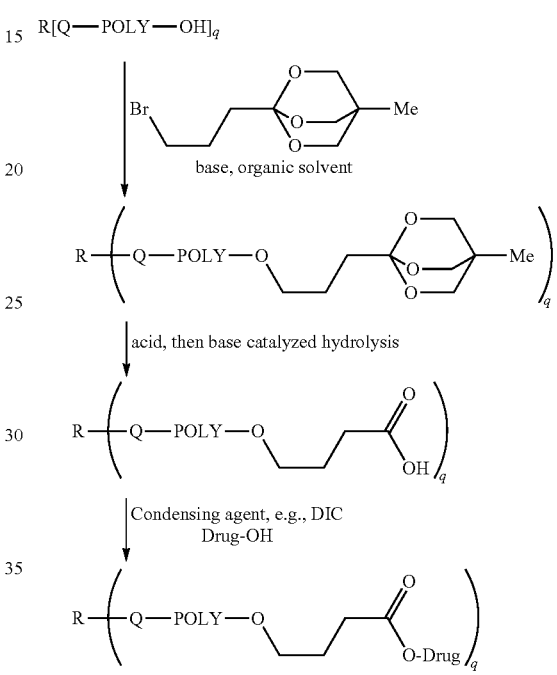

In an alternative approach, the drug is functionalized to contain the alkanoic acid moiety, followed by covalent attachment to the multi-armed polymer to provide a conjugate as described herein. This method is illustrated below using a PEG BTC active ester to ultimately yield a urethane bond between the linker and the PEG segment. Many variations on the methods described can be envisioned by one skilled in the art.

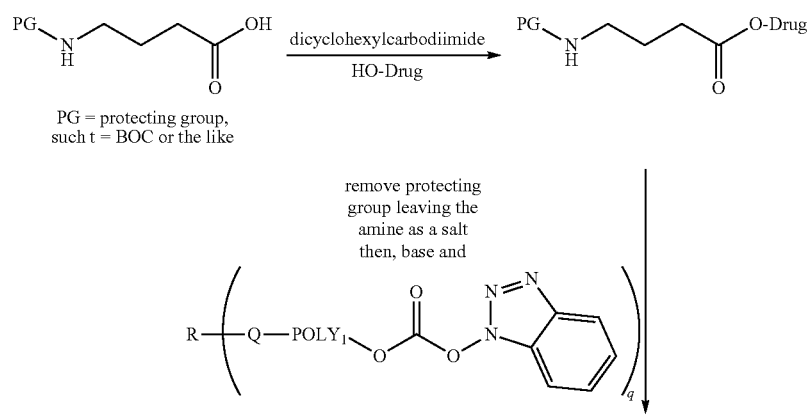

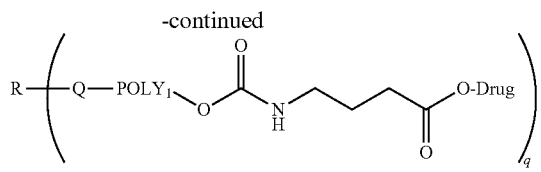

The methods described herein are flexible enough to allow many variations in the exact structures of the reactants and products. For example, one may readily substitute alkyl chlorides or mesylates for the respective alkyl bromides in substitution reactions. Also, where active NHS esters are used for illustration, other active esters, such as p-nitrophenolates or BTCs can be used. Also, extender groups, especially those containing ethyleneoxy subunits, may be used as a second linker, between the core multiarm PEG structure and the terminating linker. Selection of suitable functional groups, linkers, protecting groups, and the like to achieve a multi-arm polymer prodrug in accordance with the invention, will depend, in part, on the functional groups on the active agent and on the multi-armed polymer starting material and will be apparent to one skilled in the art, based upon the contents of the present disclosure.

The prodrug product may be further purified. Methods of purification and isolation include precipitation followed by filtration and drying, as well as chromatography. Suitable chromatographic methods include gel filtration chromatography, ion exchange chromatography, and Biotage Flash chromatography.

Pharmaceutical Compositions

The invention provides pharmaceutical formulations or compositions, both for veterinary and for human medical use, which comprise one or more multi-armed polymer conjugates of the invention or a pharmaceutically acceptable salt thereof, with one or more pharmaceutically acceptable carriers, and optionally any other therapeutic ingredients, stabilizers, or the like. The carrier(s) must be pharmaceutically acceptable in the sense of being compatible with the other ingredients of the formulation and not unduly deleterious to the recipient thereof. The compositions of the invention may also include polymeric excipients/additives or carriers, e.g., polyvinylpyrrolidones, derivatized celluloses such as hydroxymethylcellulose, hydroxyethylcellulose, and hydroxypropylmethylcellulose, Ficolls (a polymeric sugar), hydroxyethylstarch (HES), dextrates (e.g., cyclodextrins, such as 2-hydroxypropyl-β-cyclodextrin and sulfobutylether-β-cyclodextrin), polyethylene glycols, and pectin. The compositions may further include diluents, buffers, binders, disintegrants, thickeners, lubricants, preservatives (including antioxidants), flavoring agents, taste-masking agents, inorganic salts (e.g., sodium chloride), antimicrobial agents (e.g., benzalkonium chloride), sweeteners, antistatic agents, surfactants (e.g., polysorbates such as "TWEEN 20" and "TWEEN 80," and pluronics such as F68 and F88, available from BASF), sorbitan esters, lipids (e.g., phospholipids such as lecithin and other phosphatidylcholines, phosphatidylethanolamines, fatty acids and fatty esters, steroids (e.g., cholesterol)), and chelating agents (e.g., EDTA, zinc and other such suitable cations). Other pharmaceutical excipients and/or additives suitable for use in the compositions according to the invention are listed in "Remington: The Science & Practice of Pharmacy," 19th ed., Williams & Williams, (1995), and in the "Physician's Desk Reference," 52nd ed., Medical Economics, Montvale, N.J. (1998), and in "Handbook of Pharmaceutical Excipients," Third Ed., Ed. A. H. Kibbe, Pharmaceutical Press, 2000.

The prodrugs of the invention may be formulated in compositions including those suitable for oral, rectal, topical, nasal, ophthalmic, or parenteral (including intraperitoneal, intravenous, subcutaneous, or intramuscular injection) administration. The compositions may conveniently be presented in unit dosage form and may be prepared by any of the methods well known in the art of pharmacy. All methods include the step of bringing the active agent or compound (i.e., the prodrug) into association with a carrier that constitutes one or more accessory ingredients. In general, the compositions are prepared by bringing the active compound into association with a liquid carrier to form a solution or a suspension, or alternatively, bringing the active compound into association with formulation components suitable for forming a solid, optionally a particulate product, and then, if warranted, shaping the product into a desired delivery form. Solid formulations of the invention, when particulate, will typically comprise particles with sizes ranging from about 1 nanometer to about 500 microns. In general, for solid formulations intended for intravenous administration, particles will typically range from about 1 nm to about 10 microns in diameter. Particularly preferred are sterile, lyophilized compositions that are reconstituted in an aqueous vehicle prior to injection.

A preferred formulation is a solid formulation comprising the multi-arm polymer conjugate where the active agent, D, is docetaxel. The solid formulation is typically diluted with 5% dextrose injection or 0.9% sodium chloride injection prior to intravenous infusion.

The amount of multi-armed polymer conjugate in the formulation will vary depending upon the specific active agent employed, its activity, the molecular weight of the conjugate, and other factors such as dosage form, target patient population, and other considerations, and will generally be readily determined by one skilled in the art. The amount of conjugate in the formulation will be that amount necessary to deliver a therapeutically effective amount of the compound, e.g., an alkaloid anticancer agent, to a patient in need thereof to achieve at least one of the therapeutic effects associated with the compound, e.g., for treatment of cancer. In practice, this will vary widely depending upon the particular conjugate, its activity, the severity of the condition to be treated, the patient population, the stability of the formulation, and the like. Compositions will generally contain anywhere from about 1% by weight to about 99% by weight conjugate, typically from about 2% to about 95% by weight conjugate, and more typically from about 5% to 85% by weight conjugate, and will also depend upon the relative amounts of excipients/additives contained in the composition. More specifically, the composition will typically contain at least about one of the following percentages of conjugate: 2%, 5%, 10%, 20%, 30%, 40%, 50%, 60%, or more by weight.

Compositions of the present invention suitable foral administration may be provided as discrete units such as capsules, cachets, tablets, lozenges, and the like, each containing a predetermined amount of the conjugate as a powder or granules; or a suspension in an aqueous liquor non-aqueous liquid such as a syrup, an elixir, an emulsion, a draught, and the like.

Formulations suitable for parenteral administration conveniently comprise a sterile aqueous preparation of the prodrug conjugate, which can be formulated to be isotonic with the blood of the recipient.

Nasal spray formulations comprise purified aqueous solutions of the multi-armed polymer conjugate with preservative agents and isotonic agents. Such formulations are preferably adjusted to a pH and isotonic state compatible with the nasal mucous membranes.

Formulations for rectal administration may be presented as a suppository with a suitable carrier such as cocoa butter, or hydrogenated fats or hydrogenated fatty carboxylic acids.

Ophthalmic formulations are prepared by a similar method to the nasal spray, except that the pH and isotonic factors are preferably adjusted to match that of the eye.

Topical formulations comprise the multi-armed polymer conjugate dissolved or suspended in one or more media such as mineral oil, petroleum, polyhydroxy alcohols or other bases used for topical formulations. The addition of other accessory ingredients as noted above may be desirable.

Pharmaceutical formulations are also provided which are suitable for administration as an aerosol, e.g., by inhalation. These formulations comprise a solution or suspension of the desired multi-armed polymer conjugate or a salt thereof. The desired formulation may be placed in a small chamber and nebulized. Nebulization may be accomplished by compressed air or by ultrasonic energy to form a plurality of liquid droplets or solid particles comprising the conjugates or salts thereof.

Features of the Multi-armed Polymer Prodrug Conjugate

The pharmacokinetics of exemplary multi-armed polymer prodrugs in accordance with the disclosure was evaluated in different animal models to determine, at least in part, whether sustained systemic exposure to drug was achieved upon administration. The examples provided herein demonstrate that sustained systemic exposure to drug, e.g., docetaxel, is achieved upon administration of a multi-armed prodrug having the features described herein, as supported by various in-vivo studies, and moreover, that such increased and sustained exposure to drug is effective to contribute to the superior antitumor activity observed for the subject prodrugs of the instant disclosure.

As an illustration, Example 14 describes administration of 4-ARM-PEG$_{20K}$-BA-docetaxel versus docetaxel to rats. Based upon the results described herein, 4-ARM-PEG$_{20K}$-BA-docetaxel when administered to rats exhibits a low clearance and low volume of distribution, resulting in a long 4-ARM-PEG$_{20K}$-BA-docetaxel terminal half life of about 65 hours. Plasma docetaxel $C_{max}$ is approximately 6-fold lower following administration of equivalent 4-ARM-PEG$_{20K}$-BA-docetaxel compared to docetaxel doses, while AUC is similar. Plasma docetaxel half-life is estimated to be about 4-fold longer following 4-ARM-PEG$_{20K}$-BA-docetaxel administration than that observed following docetaxel administration (168 vs. 40 hours), thereby demonstrating sustained systemic docetaxel exposure upon administration of prodrug.

In further support of the exemplary prodrugs described herein as providing sustained systemic exposure to drug (e.g., docetaxel) upon administration, Example 15 demonstrates similar results in dogs. Specifically, Example 15 demonstrates a long 4-ARM-PEG$_{20K}$-BA-docetaxel terminal half-life of 31 hours. Plasma docetaxel $C_{max}$ and AUC are about 110- and 7-fold lower, respectively, following administration of equivalent 4-ARM-PEG$_{20K}$-BA-docetaxel and docetaxel doses. Moreover, the plasma docetaxel half-life following administration of 4-ARM-PEG$_{20K}$-BA-docetaxel is estimated to be about 8-fold longer than that observed following docetaxel administration (199 vs. 25 hours).

Population modeling methods applied to the pharmacokinetic data obtained further support that plasma docetaxel concentrations are sustained for an extended and prolonged period following administration of 4-ARM-PEG$_{20K}$-BA-docetaxel relative to administration of docetaxel, independent of species and dose as described in Example 16.

The observed and enhanced antitumor activity of the exemplary prodrugs of the disclosure is described in greater detail below and in the accompanying examples.

Methods of Use

The multi-armed polymer prodrugs provided herein can be used to treat or prevent any condition responsive to the unmodified active agent in any animal, particularly in mammals, including humans.

The multi-arm polymer conjugates of the invention are particularly useful as anticancer agents, i.e., have been shown to be effective in significantly reducing the growth of certain solid tumors as evidenced by representative in-vivo studies provided herein. That is to say, when the small molecule drug is an anticancer agent such as a camptothecin compound or other oncolytic such as docetaxel, the conjugates provided herein may be used to treat cancer. Types of cancer suitable for treatment by administering a multi-armed polymer alkanoate conjugates as provided herein include breast cancer, ovarian cancer, colon cancer, colorectal cancer, prostate cancer, gastric cancer, malignant melanoma, small cell lung cancer, non-small cell lung cancer, thyroid cancers, kidney cancer, cancer of the bile duct, brain cancer, cancer of the head and neck, lymphomas, leukemias, rhabdomyosarcoma, neuroblastoma, and the like. The multi-arm polymer conjugates of the invention are particularly effective in targeting and accumulating in solid tumors. The multi-arm polymer conjugates are also useful in the treatment of HIV and other viruses.

The multi-arm polymer conjugate may also provide improved anti-tumor activity in patients with refractory cancer, i.e., cancer that has not responded to various other treatments. Also, an added advantage of administering the multi-arm polymer conjugate is the likelihood of reduced patient myelosuppression when compared to administration of unmodified active agent.

Methods of treatment comprise administering to a mammal in need thereof a therapeutically effective amount of a composition or formulation containing a multi-arm polymer conjugate as provided herein. A therapeutically effective dosage amount of any specific multi-arm polymer conjugate will vary from conjugate to conjugate, patient to patient, and will depend upon factors such as the condition of the patient, the activity of the particular active agent employed, the route of delivery, and condition being treated.

For camptothecin-type active agents, dosages from about 0.5 to about 100 mg camptothecin/kg body weight, preferably from about 10.0 to about 60 mg/kg, are preferred. For taxane-type active agents, dosages from about 5 to about 500 mg/m$^2$, preferably from about 25 to about 125 mg/m$^2$ are preferred, based upon the amount of the taxane moiety. When administered conjointly with other pharmaceutically active agents, even less of the multi-arm polymer conjugate may be therapeutically effective. The range set above is illustrative and those skilled in the art will determine optimal dosing of the multi-arm polymer conjugate based on clinical experience and the particular treatment indication.

Methods of treatment also include administering a therapeutically effective amount of a composition or formulation comprising a multi-arm polymer conjugate of an anticancer agent, e.g., a camptothecin or taxane compound as described herein, in conjunction with a second anticancer agent. For example, in the treatment of colorectal cancer, a multi-aim polymer prodrug of a camptothecin or docetaxel type compound may be administered in conjuction with chemotherapeutics such as 5-fluorouracil or leucovorin xeloda, or with agents such as avastin, Erbitux® (cetuximab), or Vectibix™ (panitumumab). In the treatment of breast cancer, therapy may include administration of a multi-arm polymer conjugate as described herein, optionally in combination with xeloda, paclitaxel, docetaxel, or abraxane. In treating lung cancer, therapy may include, along with administration of a multi-arm polymer conjugate of the invention, administration of cis-platin, carboplatin, gemcitabine, alimpta, and docetaxel (the latter in the instance in which the multi-arm polymer conjugate itself does not comprise docetaxel).

In one embodiment, a multi-armed polymer camptothecin-containing conjugate as described herein is administered in combination with 5-fluorouracil and folinic acid, as described in U.S. Pat. No. 6,403,569.

The multi-arm polymer conjugate of the invention may be administered once or several times a day, preferably once a day or less. Illustrative dosing schedules include once per week, once every two weeks, or once every three weeks. In the instance of a maintenance dose, dosing may take place even less frequently than once every three weeks, such as once monthly. The duration of the treatment may be once per day for a period of from two to three weeks and may continue for a period of months or even years. The daily dose can be administered either by a single dose in the form of an individual dosage unit or several smaller dosage units or by multiple administration of subdivided dosages at certain intervals.

The multi-arm polymer conjugates provided herein exhibit improved efficacy, improved tolerability and reduced vehicle-associated toxicity when compared to administration of the corresponding unmodified small molecule drug, absent the multi-arm polymer alkanoate scaffold.

Supporting examples illustrate the anti-tumor activity of a representative multi-armed polymer alkanoate conjugate in various in-vivo mouse xenograft models for various types of cancer. As described in detail in Example 13, 4-ARM-PEG$_{20K}$-BA-DOC exhibits greater anti-tumor activity than docetaxel per se in H460 and LS174T mouse xenograft models. Partial regressions were observed in two of the three cell lines examined for 4-ARM-PEG$_{20K}$-BA-DOC, while no regressions were observed for docetaxel. Additionally, as shown in Example 13, at the maximum tolerated dose, the percentage tumor growth delay (TGD) for 4-ARM-PEG$_{20K}$-BA-DOC was 2.5-, 2.0-, and 1.6-fold-greater than for docetaxel in 1-1460, LoVo, and LS174T xenograft models, respectively—all pointing to the vastly superior features of the multi-armed conjugates provided herein.

It is to be understood that while the invention has been described in conjunction with the preferred specific embodiments thereof, that the foregoing description as well as the examples that follow are intended to illustrate and not limit the scope of the invention. Other aspects, advantages and modifications within the scope of the invention will be apparent to those skilled in the art to which the invention pertains.

EXPERIMENTAL

The practice of the invention will employ, unless otherwise indicated, conventional techniques of organic synthesis and the like, which are within the skill of the art. Such techniques are fully described in the literature. Reagents and materials are commercially available unless specifically stated to the contrary. See, for example, M. B. Smith and J. March, *March's Advanced Organic Chemistry: Reactions Mechanisms and Structure, 6th Ed.* (New York: Wiley-Interscience, 2007), supra, and Comprehensive Organic Functional Group Transformations II, Volumes 1-7, Second Ed.: A Comprehensive Review of the Synthetic Literature 1995-2003 (Organic Chemistry Series), Eds. Katritsky, A. R., et al., Elsevier Science.

In the following examples, efforts have been made to ensure accuracy with respect to numbers used (e.g., amounts, temperatures, etc.) but some experimental error and deviation should be accounted for. Unless indicated otherwise, temperature is in degrees C. and pressure is at or near atmospheric pressure at sea level.

The following examples illustrate certain aspects and advantages of the present invention, however, the present invention is in no way considered to be limited to the particular embodiments described below.

Abbreviations

CM carboxymethyl or carboxymethylene ($-CH_2COOH$)

DCC 1,3-dicyclohexylcarbodiimide

DCM dichloromethane

DIC N,N'-diisopropylcarbodiimide

DPTS 4-(dimethylamino)-pyridinium-p-toluenesulfonate

DMF dimethylformamide

DMAP 4-(N,N-dimethylamino)pyridine

DMSO dimethyl sulfoxide

DI deionized

HCl hydrochloric acid

HOBT hydroxybenzyltriazole

HPLC high performance liquid chromatography

IPA isopropyl alcohol

K or kDa kilodaltons

MALDI-TOF Matrix Assisted Laser Desorption Ionization Time-of-Flight

MeOH methanol

MW molecular weight

NMR nuclear magnetic resonance

RT room temperature

SCM succinimidylcarboxymethyl ($-CH_2-COO-N$-succinimidyl)

SDS-PAGE sodium dodecyl sulfate-polyacrylamide gel electrophoresis

SEC size exclusion chromatography

TFA trifluoroacetic acid

THF tetrahydrofuran

TLC thin layer chromatography

Materials and Methods

Docetaxel (Taxotere®) was purchased from Hangzhou HETD Pharm & Chem. Co., Ltd, The People's Republic of China.

Pentaerythitol based 4-ARM-PEG$_{10K}$-OH, 4-ARM-PEG$_{20K}$-OH, 4-ARM-PEG$_{30K}$-OH, and 4-ARM-PEG$_{40K}$-OH were obtained from NOF Corporation (Japan). 4-ARM-PEG$_{20K}$-OH possesses the following structure: $C-(CH_2O-(CH_2CH_2O)_nH)_4$, as shown structurally below:

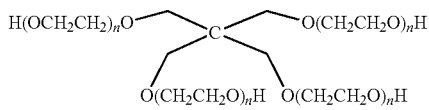

The variable "n" in each arm represents the number of monomer subunits corresponding to a PEG average molecular weight of 2.5, 5, 7.5, or 10 kilodaltons, such that the shorthand abbreviation for the 4-arm structure indicates an overall average molecular weight for the polymer portion of the molecule of 10, 20, 30, or 40 kilodaltons, respectively.

All $^1$HNMR data was generated by a 300 or 400 MHz NMR spectrometer manufactured by Bruker.

Example 1

Synthesis of 4-ARM-PEG$_{20K}$-Butanoic Acid ("4-ARM-PEG$_{20K}$-BA")

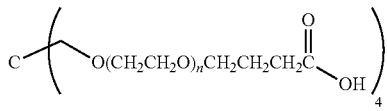

A solution of pentaerythritol-based 4-ARM-PEG$_{20K}$-OH (100.0 g, 0.020 equivalents) (NOF Corporation) in toluene (750 ml) was azeotropically dried by distilling off 150 ml of toluene. 1.0M solution of potassium tert-butoxide in tert-butanol (60 ml, 0.060 moles) and 1-(3-bromopropyl)-4-methyl-2,6,7-trioxabicyclo[2,2,2]octane (12.6 g, 0.052 moles) were added and the mixture was stirred overnight at 70° C. under argon atmosphere. The solvent was distilled off under reduced pressure and the residue was dissolved in distilled water (1,000 ml). The pH of the solution was adjusted to 2 with 5% phosphoric acid and the solution was stirred for 15 minutes at room temperature. Next, the pH was readjusted to 12 by addition of 1M sodium hydroxide, and the solution was stirred for two hours keeping the pH at 12 by periodic addition of 1M sodium hydroxide. Thereafter, the pH was adjusted to 3 by addition of 5% phosphoric acid and the product was extracted with dichloromethane.

The extract was dried over anhydrous magnesium sulfate, filtered, and then added to isopropyl alcohol. The precipitated product was removed by filtration and dried under reduced pressure.

Yield 95.0 g. $^1$H NMR (d$_6$-DMSO): δ1.72 ppm (q, C$\underline{H}_2$—CH$_2$—COO—), 2.24 ppm (t, —CH$_2$—COO—), 3.51 ppm (s, PEG backbone). Substitution=~100% (meaning that, within the accuracy of the NMR method, each OH— group located on the ends of each arm of the 4-ARM-PEG starting material was converted to the corresponding butanoic acid).

Example 2

Synthesis of 4-ARM-PEG$_{20K}$-Butanoate-Linked Docetaxel Conjugate ("4-ARM-PEG$_{20K}$-BA-DOC")

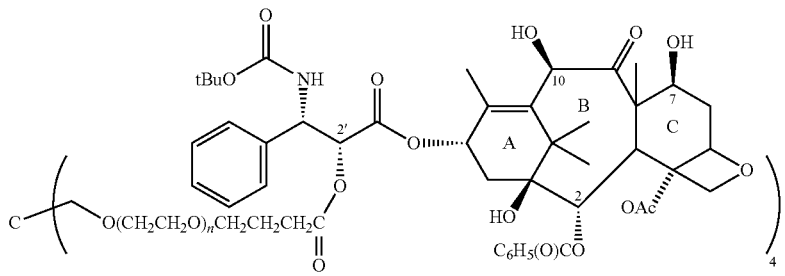

To a solution of 4-ARM-PEG$_{20K}$-butanoic acid (5.0 g, 0.0010 equivalents, Example 1), docetaxel (1.0 g, 0.0012 moles), and p-toluenosulfonic acid 4-dimethylaminopyridine salt (0.15 g, 0.00051 moles) in 60 ml of anhydrous dichloromethane, N,N'-diisopropylcarbodiimide (0.63 g, 0.005 mole) was added and the mixture was stirred overnight at room temperature under an argon atmosphere. The solvent was distilled off under reduced pressure. The residue was dissolved in dichloromethane (7.5 ml) and added to a 1:1 mixture of isopropyl alcohol and diethyl ether (100 ml). The precipitated product was filtered off and dried under reduced pressure. The precipitation was repeated giving 3.8 g of white solid product.

$^1$H NMR (400 MHz, CDCl$_3$): δ 1.06 (s, 12H), 1.16 (s, 12H), 1.27 (s, 36H), 1.68 (s, 12H), 1.84 (m, 8H), 2.20-2.60 (m, 14H), 3.30-3.80 (m, ~1900H), 3.90 (d, 4H), 4.12 (d, 4H), 4.20 (m, 4H), 4.26 (d, 4H), 4.97 (d, 4H), 5.15 (s, 4H), 5.28 (s, 4H), 5.38 (m, 8H), 5.62 (d, 4H), 6.30 (t, 4H), 7.24 (m, 8H), 7.30 (m, 8H), 7.44 (m, 8H), 7.54 (m, 4H), 8.04 (d, 8H).

NMR analysis of the product in CDCl$_3$ as a solvent showed that to each molecule of 4ARM-PEG$_{20K}$-butanoic acid (4-ARM-PEG$_{20K}$-BA) was connected 4 molecules of docetaxel. Substitution: ~98-100%.

Example 3

Synthesis of 4-ARM-PEG$_{20K}$-Glycine (Pentaerythritolyl-4-ARM-(PEG-1-Methylene-2 Oxo-Vinylamino Acetic acid)-20K) ("4-ARM-PEG$_{20K}$-CM-GLY")

The following example is provided as a basis for comparing the extent of drug (i.e., docetaxel) substitution on the 4-ARM-PEG-OH starting material described in Example 1, 4-ARM-PEG$_{20K}$-butanoic acid, versus 4-ARM-PEG$_{20K}$-CM-glycine.

A. Formation of 4-ARM-PEG$_{20K}$-Acetic Acid (4-ARM-PEG$_{20K}$-CM)

A solution of pentaerythitol-based 4-ARM-PEG$_{20K}$-OH (100.0 g, 0.020 equivalents) (NOF Corporation) in toluene (750 ml) was azeotropically dried by distilling off 150 ml of toluene. 1.0M solution of potassium tert-butoxide in tert-butanol (60 ml, 0.060 moles) and tert-butyl bromoacetate (12.9 g, 0.066 moles) were added and the mixture was stirred overnight at 45° C. under argon atmosphere. The solvent was distilled off under reduced pressure and the residue was dissolved in distilled water (1,000 ml). The pH of the solution was adjusted to 12 by addition of 1M sodium hydroxide and the solution was stirred overnight keeping the pH at 12.0 by periodic addition of 1M sodium hydroxide. The pH was adjusted to 2 by addition of 1M phosphoric acid. The resulting product, 4-ARM-PEG$_{20K}$-acetic acid (also referred to as "4-ARM-PEG$_{20K}$-CM") was extracted with dichloromethane. The extract was dried over anhydrous sodium sulfate, filtered, and concentrated. The concentrated extract was then added to ethyl ether.

The precipitated product was collected by filtration and dried under reduced pressure. Yield 95.5 g. $^1$H NMR (d$_6$-DMSO): δ 3.51 ppm (s, PEG backbone), 4.01 ppm (s, —CH$_2$—COO—). Substitution 100%. Substitution=~100% (meaning that, within the accuracy of the NMR method, each OH— group located on the ends of each arm of the 4-ARM-PEG starting material was converted to the corresponding acetic acid).

B. Formation of 4-ARM-PEG$_{20K}$-Acetic Acid, N-Hydroxysuccinimide ester (NHS)

4-ARM-PEG$_{20K}$-acetic acid (90.0 g, 0.018 equivalents) was dissolved in dichloromethane (270 ml) and N-hydroxysuccinimide (2.20 g, 0.019 mol) was added. Next dicyclohexylcarbodiimide (4.13 g, 0.020 moles) was added, and the solution was stirred at room temperature overnight. The reaction mixture was filtered, concentrated, and precipitated by addition to isopropyl alcohol.

Yield of final product: 82 g. $^1$H NMR (d$_6$-DMSO): δ 2.81 ppm (s, succinimide), 3.51 ppm (s, PEG backbone), 4.60 ppm (s, —CH$_2$—COO—). Substitution 100%.

C. Formation of 4-ARM-PEG$_{20K}$-CM-Glycine ("4-ARM-PEG$_{20K}$-CM-GLY")

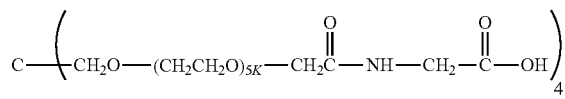

4-ARM-PEG$_{20K}$-CM-Glycine

4-ARM-PEG$_{20K}$-acetic acid, N-hydroxysuccinimide ester (80.0 g, 0.016 equivalents) was dissolved in dichloromethane (240 ml) and glycine, tert-butyl ester hydrochloride (3.22 g, 0.019 moles) was added. Next triethylamine (6.90 g) was added, and the solution was stirred at room temperature overnight. The reaction mixture was concentrated by distilling off under reduced pressure 160 ml of dichloromethane, followed by addition of 80 ml of trifluoroacetic acid. The mixture was stirred for three hours at room temperature, followed by distillation under reduced pressure to remove dichloromethane and trifluoroacetic acid. The crude product was dissolved in 120 ml dichloromethane and precipitated by addition of isopropyl alcohol.

The precipitate, (4-ARM-PEG$_{20K}$-CM-GLY) was collected and dried to provide 74 g of a white solid product. $^1$H NMR (CDCl$_3$): δ 3.64 ppm (s, PEG backbone), 4.05 ppm (s, —CH$_2$—COO—), 4.09 ppm (d, —CH$_2$—, glycine). Substitution ~100%.

Example 4

Synthesis of 4-ARM-PEG$_{70K}$-CM-Glycine-Linked Docetaxel Conjugate ("4-ARM-PE-PEG$_{20K}$-CM-GLY-DOC")

To a solution of 4-ARM-PEG$_{20K}$-acetate linked glycine (4-ARM-PEG$_{20K}$-CM-GLY, 5.0 g, 0.0010 equivalents), docetaxel (1.0 g, 0.0012 moles), and p-toluenosulfonic acid 4-dimethylaminopyridine salt (1.5 g, 0.0051 moles) in 60 ml of anhydrous dichloromethane, N,N'-diisopropylcarbodiimide (0.63 g, 0.005 mole) was added and the mixture was stirred overnight at room temperature under argon atmosphere. The solvent was distilled off under reduced pressure. The residue was dissolved in dichloromethane (7.5 ml) and added to a 1:1 mixture of isopropyl alcohol and diethyl ether (100 ml). The precipitated product was filtered off and dried under reduced pressure. The precipitation was repeated giving 3.7 g of white solid product.

NMR analysis of the product (4-ARM-PEG$_{20K}$-CM-GLY-DOC) in CDCl$_3$ as a solvent showed that substitution was ~75%. This means that each molecule of 4ARM-PEG$_{20K}$-CM-GLY was connected to ~3 molecules of docetaxel rather than the desired 4.

Example 5

Synthesis of Additional 4-ARM-PEG$_{10K}$-CM-Glycine-linked Docetaxel Conjugates: ("4-ARM-PE-PEG$_{10K}$-CM-GLY-DOC")

4-ARM-PEG$_{10K}$-CM-glycine-linked docetaxel conjugates were prepared in a similar fashion as described above, with the exception of their molecular weights, the average molecular mass of starting pentaerythitol based 4-ARM-PEG-OH was 10 kDa.

$^1$H NMR analysis of the 4ARM-PEG$_{(10k)}$-glycine-linked docetaxel indicated ~84% substitution.

Example 6

Synthesis of 4-ARM-PEG$_{20K}$-TEG-α-Methylpropionic Acid ("4-ARM-PEG$_{20K}$-TEG-α-MPA")

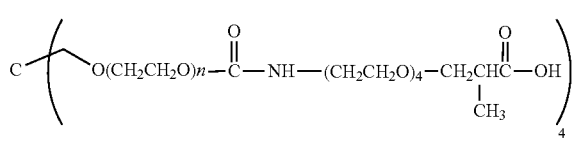

I. Synthesis of tetra(ethylene glycol)-(α-amine,sulfuric acid salt)-ω-α-methylpropionic acid, methyl ester)

A. Tetra(ethylene glycol)mono-α-methylpropionitrile

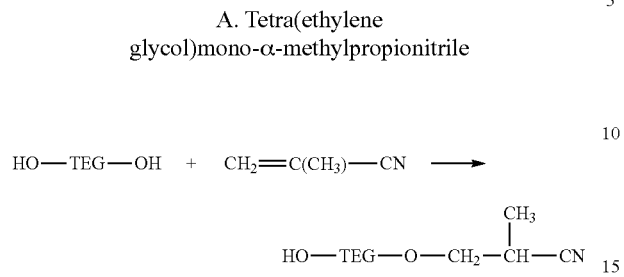

A mixture of tetra(ethylene glycol), "TEG" (194.2 g, 1.0 mole), tetrabutylammonium bromide (9.6 g), and toluene (350 ml) was azeotropically dried by distilling off toluene under reduced pressure. Solid potassium hydroxide (powder, 2.2 g) was added and the mixture was stirred for 30 minutes at room temperature. Next methacrylonitrile (50 ml) was added dropwise during two hours and the reaction mixture was stirred for 92 hours at room temperature under argon atmosphere. The crude product was dissolved in 1500 ml deionized water and the resulting solution was filtered through active carbon (50 g) and desalting column composed from Amberlite IR 120 plus (500 ml) and Amberlite IR 67. Sodium chloride (300 g) was added and the product was extracted with dichloromethane (500, 300, and 200 ml). The extract was dried (MgSO$_4$) and the solvent was distilled off under reduced pressure.

Yield: 54.0 g. $^1$H NMR (D2O): δ1.21 ppm (d, C$\underline{H_3}$—C—), 3.00 ppm (m, —CH—CN), 3.62 ppm (bm, —OCH$_2$CH$_2$O—). Purity: ~100%.

B. Tetra(ethylene glycol)mono-α-methylpropionamide

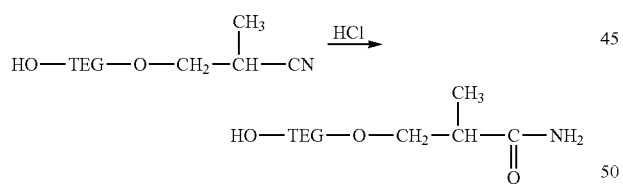

Tetra(ethylene glycol)mono-α-methylpropionitrile (54 g) was dissolved in concentrated hydrochloric acid (180 ml) and the resulting solution was stirred for 20 hours at room temperature. Deionized water (250 ml) was added and the pH was adjusted to 7.6 with 10% solution of sodium hydroxide at 7-8° C. Water was distilled under reduced pressure and the product was extracted from solid residue with anhydrous ethyl alcohol (200 ml). Ethyl alcohol was distilled from the extract and the crude product was dissolved in dichloromethane (150 ml). The solution was dried with anhydrous MgSO$_4$ and the solvent was distilled off under reduced pressure.

Yield: 53.3 g. $^1$H NMR (D$_2$O): δ 0.89 ppm (d, C$\underline{H_3}$—C—), 2.55 ppm (m, —CH—(C═O)NH$_2$), 3.47 ppm (bm, —OCH$_2$CH$_2$O—). Purity: ~100%.

C. Tetra(ethylene glycol)mono-α-methylpropionic acid

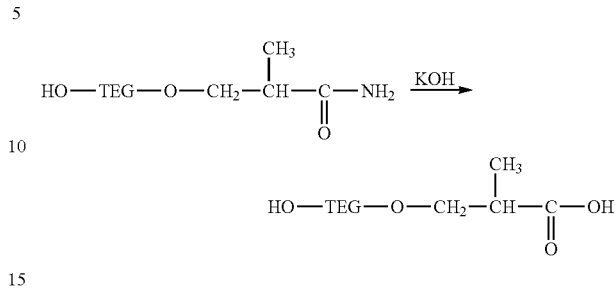

Tetra(ethylene glycol)mono-α-methylpropionamide (45 g) was dissolved in potassium hydroxide solution (concentration 6.67%, 450 ml) and the resulting solution was stirred 70 h at room temperature. Next the pH of the reaction mixture was adjusted to 7.5 with 10% phosphoric acid at temperature 7-8° C. Water was distilled under reduced pressure and the product was extracted from solid residue with anhydrous ethyl alcohol (300 ml). Then ethyl alcohol was distilled from the extract. The crude product was dissolved in deionized water (50 ml) and impurities were extracted with dichloromethane (4×100 ml). NaCl (10 g) was added and the pH of the solution was adjusted to 3.0 with 10% hydrochloric acid. The product was extracted with dichloromethane (100, 100, and 80 ml). The extract was dried with anhydrous MgSO$_4$ and the solvent was distilled off under reduced pressure.

Yield: 25.3 g. $^1$H NMR (D$_2$O): δ 1.06 ppm (d, C$\underline{H_3}$—C—), 2.73 ppm (m, —CH—COO—), 3.60 ppm (bm, —OCH$_2$CH$_2$O—). Purity: ~100%.

D. Tetra(ethylene glycol)mono-α-methylpropionic acid, methyl ester

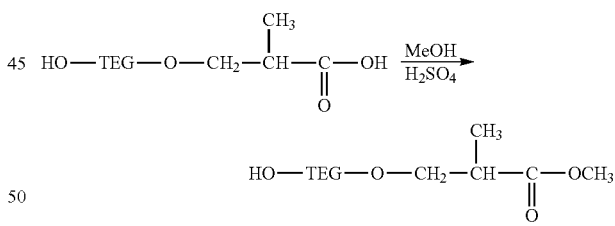

Tetra(ethylene glycol)mono-α-methylpropionic acid (25 g) was dissolved in anhydrous methyl alcohol (350 ml), concentrated sulfuric acid (6.5 ml) was added and the solution was stirred for three hours at room temperature. The pH of the reaction mixture was adjusted to 6.0 with 8% NaHCO$_3$ aqueous solution and methyl alcohol was distilled off under reduced pressure. The product was extracted with dichloromethane (100, 80, and 50 ml). The extract was dried with anhydrous MgSO$_4$ and the solvent was distilled off under reduced pressure.

Yield: 24.0 g. $^1$H NMR (d6-DMSO): 6 1.06 ppm (d, C$\underline{H_3}$—C—), 2.69 ppm (m, —CH—COO), 3.47 ppm (bm, —OCH$_2$CH$_2$O—), 360 ppm (s, CH$_3$O—). Purity: ~100%.

E. Tetra(ethylene glycol)-α-mesylate-ω-(α-methyl-propionic acid, methyl ester)

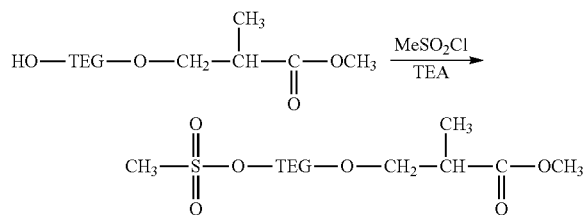

A mixture of tetra(ethylene glycol)mono-α-methylpropionic acid, methyl ester (24 g, 0.0815 moles) and toluene (240 ml) was azeotropically dried by distilling off toluene under reduced pressure. The dried tetra(ethylene glycol)mono-α-methylpropionic acid, methyl ester was dissolved in anhydrous toluene (200 ml). To the solution were added 40 ml of anhydrous dichloromethane and 12.5 ml of triethylamine (0.0897 moles). Then 10.0 g of methanesulfonyl chloride (0.0873 moles) dissolved in dichloromethane (50 ml) was added dropwise at 0 ~5° C. The solution was stirred at room temperature under argon atmosphere overnight. Next sodium carbonate (10 g) was added, the mixture was stirred for one hour. Then the solution was filtered and solvents were distilled off under reduced pressure.

Yield: 28.3 g. $^1$H NMR ($d_6$-DMSO): 1.06 ppm (d, $CH_3$—C—) 2.70 ppm (m, —CH—COO—), 3.18 ppm (s, $CH_3$—, methanesulfonate), 3.49 ppm (bm, —$OCH_2CH_2O$—), 3.60 ppm (s, $CH_3O$—), 3.67 ppm (m, —$CH_2$—$CH_2$-methanesulfonate), 4.31 ppm (m, —$CH_2$-methanesulfonate). Purity: ~100%.

F. Tetra(ethylene glycol)-(α-amine, hydrochloride)-ω-(-α-methylpropionic acid)

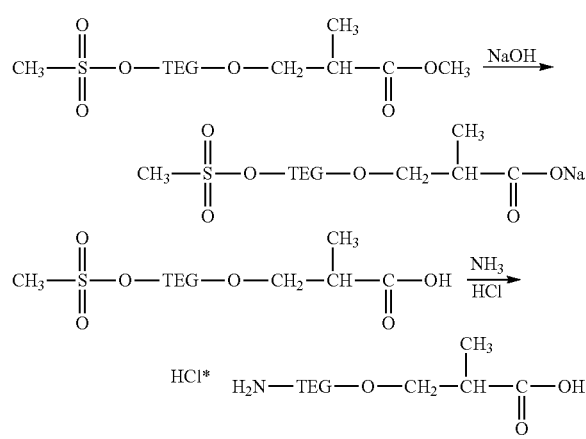

To a mixture of tetra(ethylene glycol)-α-mesylate-ω-(-α-methylpropionic acid, methyl ester) (23.8 g) and deionized water (50 ml), 70 ml of 5-% NaOH solution was added gradually during for six hours keeping the pH at 12.0-12.3. Next concentrated ammonium hydroxide (1500 ml) was added and the mixture was stirred for 64 hours at room temperature. Then the mixture was concentrated to dryness under reduced pressure. The residue was dissolved in deionized water (150 ml) and the pH of the solution was adjusted to 3.0 with 1 M HCl. Water was distilled off under reduced pressure and the crude product was dissolved in dichloromethane (150 ml). The solution was filtered, dried with anhydrous $MgSO_4$, and the solvent was distilled off under reduced pressure.

Yield: 19.4 g. $^1$H NMR ($D_2O$): 1.06 ppm (d, $CH_3$—C—) 2.72 ppm (m, —CH—COO—), 3.13 ppm (t, —$CH_2$—$NH_2$*HCl), 3.64 ppm (bm, —$OCH_2CH_2O$—). Purity: ~100%.

G. Tetra(ethylene glycol)-(α-amine,sulfuric acid salt)-ω-(-α-methylpropionic acid, methyl ester)

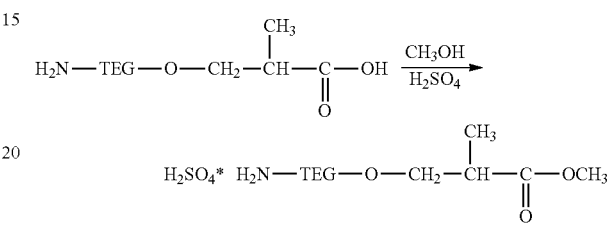

Tetra(ethylene glycol)-(α-amine, hydrochloride)-ω-(-α-methylpropionic acid) (19.4 g) was dissolved in anhydrous methyl alcohol (280 ml), concentrated sulfuric acid (5.2 ml) was added and the solution was stirred for three hours at room temperature. The pH of the reaction mixture was adjusted to 6.0 with 8% $NaHCO_3$ aqueous solution and the solvents were distilled off under reduced pressure. The crude product was dissolved in dichloromethane (250 ml). The solution was dried with anhydrous $MgSO_4$ and the solvent was distilled off under reduced pressure.

Yield: 15.7 g. $^1$H NMR ($D_2O$): 1.04 ppm (d, $CH_3$—C—) 2.77 ppm (m, —CH—COO—), 3.11 ppm (t, —$CH_2$—$NH_2$*$H_2SO_4$), 3.62 ppm (bm, —$OCH_2CH_2O$—). Purity: ~100%.

II. Synthesis of 4-ARM-PEG$_{20K}$-Benzotriazolyl Carbonate ("4-ARM-PEG$_{20K}$-BTC")

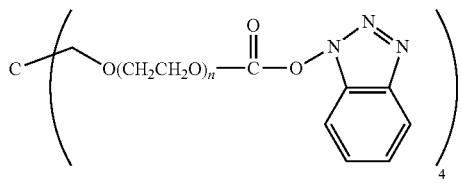

A solution of pentaerythitol-based 4-ARM-PEG$_{20K}$-OH (10.0 g, 0.0020 equivalents) (NOF Corporation) in acetonitrile (100 ml) was azeotropically dried by distilling off the solvent. Next the product was redissolved in 50 ml of anhydrous acetonitrile and pyridine (0.49 ml) and di(1-benzotriazolyl)carbonate (1.31 g of 59% dispersion in trichloroethane) was added and the mixture was stirred at room temperature under nitrogen atmosphere overnight. The solvent was distilled off under reduced pressure and the product was precipitated with isopropyl alcohol. The precipitated product was dissolved in dichloromethane (10 ml) and reprecipitated with isopropyl alcohol, filtered off and dried under reduced pressure.

Yield: 9.8 g. $^1$H NMR ($d_6$-DMSO): 3.51 ppm (s, polymer backbone), 4.62 ppm (m, PEG-$OCH_2$—$CH_2$—$OCO_2$—, 2H), 7.41-8.21 ppm (complex mult, benzotriazole protons, 4H). Substitution=~100% (meaning that, within the accuracy of the NMR method, each OH— group located on the ends of each arm of the 4-ARM-PEG starting material was converted to the corresponding benzotriazolyl carbonate group).

III. Synthesis of 4-ARM-PEG$_{20K}$-TEG-α-Methyl-propionic Acid ("4-ARM-PEG$_{20K}$-TEG-α-MPA")

To a solution of tetra(ethylene glycol)-(α-amine,sulfuric acid salt)-ω-(-α-methylpropionic acid, methyl ester) (0.75 g) in anhydrous dichloromethane (80 ml), triethylamine (0.56 ml) was added and then solid 4-ARM-PEG$_{20K}$-benzotriazolyl carbonate ("4-ARM-PEG$_{20K}$-BTC") (8.0 g) was added portionwise and the resulting solution was stirred overnight at room temperature under argon atmosphere. Next the solution was concentrated under reduced pressure and the product was precipitated with isopropyl alcohol and dried under vacuum. Next it was dissolved in distilled water (200 ml). The pH of the solution was adjusted to 12.1 with 1M sodium hydroxide, and the solution was stirred for five hours keeping the pH at 12.1 by periodic addition of 1M sodium hydroxide. Thereafter, NaCl (10 g) was added and the pH was adjusted to 3 by addition of 10% phosphoric acid and the product was extracted with dichloromethane. The extract was dried over anhydrous sodium sulfate, filtered, and concentrated. The concentrated extract was then added to isopropyl alcohol.

The precipitated product was collected by filtration and dried under reduced pressure. Yield: 7.4 g. $^1$H NMR (d$_6$-DMSO): δ 1.00 ppm (d, CH$_3$—C—), 2.55 ppm (m, —CH—COO—), 3.08 ppm (q, —CH$_2$N—NH—), 3.51 ppm (s, PEG backbone), 4.00 ppm (s, —CH$_2$—COO—), 7.16 ppm (t, —(C=O)—NH—). Substitution ~100% (meaning that each OH— group located on the ends of each arm of the 4-ARM-PEG starting material was converted to the corresponding □-methyl propionic acid).

Example 7

Synthesis of 4-ARM-PEG$_{20K}$-Hexanoic Acid ("4-ARM-PEG$_{20K}$-HA")

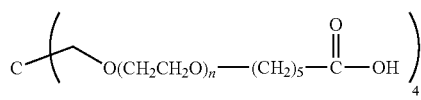

A solution of pentaerythitol-based 4-ARM-PEG$_{20K}$-OH (50.0 g, 0.010 equivalents) (NOF Corporation) in anhydrous toluene (500 ml) was azeotropically dried by distilling off toluene. The dried product was dissolved in anhydrous toluene (500 ml) and 1.0 M solution of potassium tert-butoxide in tert-butanol (30 ml, 0.030 moles) and 1-(5-bromopentyl)-4-methyl-2,6,7-trioxabicyclo[2,2,2]octane (7.8 g, 0.028 moles) were added and the mixture was stirred overnight at 72° C. under argon atmosphere. The solvent was distilled off under reduced pressure and the residue was dissolved in distilled water (400 ml). The pH of the solution was adjusted to 2 with 10% phosphoric acid and the solution was stirred for 15 minutes at room temperature. Next, the pH was readjusted to 12.5 by addition of 1M sodium hydroxide, and the solution was stirred for two hours keeping the pH at 12.1-12.5 by periodic addition of 1M sodium hydroxide. Thereafter, the pH was adjusted to 3 by addition of 10% phosphoric acid and the product was extracted with dichloromethane.

The extract was dried over anhydrous magnesium sulfate, filtered, concentrated under reduced pressure and then added to ethyl ether. The precipitated product was removed by filtration and dried under reduced pressure.

Yield: 48.5 g. $^1$H NMR (d$_6$-DMSO): δ 1.28 ppm (m, —CH$_2$—CH$_2$—CH$_2$—CH$_2$—CH$_2$—COO—), 1.48 ppm (m, —CH$_2$—CH$_2$—CH$_2$—CH$_2$—CH$_2$—COO—), 2.18 ppm (t, —CH$_2$—COO—), 3.51 ppm (s, PEG backbone). Substitution=~100% (meaning that each OH— group located on the ends of each arm of the 4-ARM-PEG starting material was converted to the corresponding hexanoic acid).

Example 8

Synthesis of 4-ARM-PEG$_{20K}$-Octanoic Acid ("4-ARM-PEG$_{20K}$-OA")

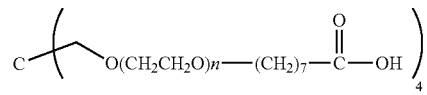

I. Synthesis of 8-Bromooctanoate Ester of 3-Methyl-3-Oxetanemethanol

To a solution of 8-bromooctanoic acid (22.5 g, 0.101 moles), 3-methyl-3-oxetanemethanol (11.0 g, 0.108 moles), and 1-hydroxybenzotriazole (1.6 g) in anhydrous dichloromethane (500 ml) cooled to 0-5° C., a solution of N,N'-dicycloxehyldicarbodiimide (22.3 g, 0.108 moles) in anhydrous dichloromethane (110 ml) was added dropwise during 45 minutes. Next, 4-(dimethylamino)pyridine (1.8 g) was added and the mixture was stirred overnight at room temperature under argon atmosphere. The solution was filtered and washed two times with 5-% phosphoric acid (2×250 ml). Next it was dried with anhydrous MgSO4 and the solvent was distilled off. Yield of crude product 28.0 g.

II. Synthesis of 1-(7-bromoheptyl)-4-methyl-2,6,7-trioxabicyclo[2,2,2]octane 8-Bromooctanoate ester of 3-methyl-3-oxetanemethanol (14.0 g) was dissolved in anhydrous dichloromethane (70 ml) and the solution was cooled to 0-5° C. Boron trifluoride diethyl etherate (1.49 ml) was added and the mixture was stirred for four hours at 0-5° C. Triethylamine (7.2 ml) was added and the mixture was stirred for 15 minutes at 0-5° C. The solvent was distilled off under reduced pressure. The residue was dissolved in ethyl ether (200 ml) and the solution was filtered. Next the solvent was distilled off under reduced pressure. Yield 13.5 g.

III. Synthesis of 4-ARM-PEG$_{20K}$-Octanoic Acid

A solution of pentaerythitol-based 4-ARM-PEG$_{20K}$-OH (20.0 g, 0.004 equivalents) (NOF Corporation) in anhydrous toluene (200 ml) was azeotropically dried by distilling off toluene. The dried product was dissolved in anhydrous toluene (400 ml) and 1.0 M solution of potassium tert-butoxide in tert-butanol (12 ml, 0.012 moles) and 1-(7-bromoheptyl)-4-methyl-2,6,7-trioxabicyclo[2,2,2]octane (3.7 g, 0.012 moles) were added and the mixture was stirred overnight at 72° C. under argon atmosphere. The solvent was distilled off under reduced pressure and the residue was dissolved in distilled water (300 ml). The pH of the solution was adjusted to 2 with 10% phosphoric acid and the solution was stirred for 45 minutes at room temperature. Next, the pH was readjusted to 12.5 by addition of 1M sodium hydroxide, and the solution was stirred for three hours keeping the pH at 12.1-12.5 by periodic addition of 1M sodium hydroxide. Thereafter, the pH was adjusted to 3 by addition of 10% phosphoric acid and the product was extracted with dichloromethane.

The extract was dried over anhydrous magnesium sulfate, filtered, concentrated under reduced pressure and then precipitated with isopropyl alcohol. The precipitated product was removed by filtration and dried under reduced pressure, then it was dissolved in dichloromethane (15 ml) and reprecipitated with isopropyl alcohol. Yield: 15.5 g.

Yield: 48.5 g. $^1$H NMR (d$_6$-DMSO): δ 1.25 ppm (m, —CH$_2$—CH$_2$—CH$_2$—CH$_2$—CH$_2$—CH$_2$—CH$_2$—COO—), 1.47 ppm (m, —CH$_2$—CH$_2$—CH$_2$—CH$_2$—CH$_2$—CH$_2$—CH$_2$—COO—), 2.15 ppm (t, —CH$_2$—COO—), 3.51 ppm (s, PEG backbone). Substitution=~100% (meaning that each OH— group located on the ends of each arm of the 4-ARM-PEG starting material was converted to the corresponding octanoic acid).

Example 9

Synthesis of 4-ARM-PEG$_{20K}$-Decanoic Acid ("4-ARM-PEG$_{20K}$-DA")

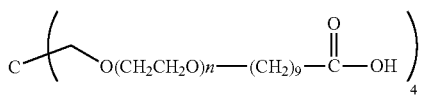

I. Synthesis of 10-Bromodecanoate Ester of 3-Methyl-3-Oxetanemethanol

To a solution of 10-bromooctanoic acid (25.0 g, 0.100 moles), 3-methyl-3-oxetanemethanol (10.9 g, 0.107 moles), and 1-hydroxybenzotriazole (1.6 g) in anhydrous dichloromethane (500 ml) cooled to 0-5° C., a solution of N,N'-dicycloxehyldicarbodiimide (22.1 g, 0.107 moles) in anhydrous dichloromethane (110 ml) was added dropwise during 45 minutes. Next 4-(dimethylamino)pyridine (1.8 g) was added and the mixture was stirred overnight at room temperature under argon atmosphere. The solution was filtered and washed two times with 5-% phosphoric acid (2×250 ml). Next it was dried with anhydrous MgSO4 and the solvent was distilled off Yield 29.0 g.

II. Synthesis of 1-(9-bromononyl)-4-methyl-2,6,7-trioxabicyclo[2,2,2]octane

10-Bromodecanoate ester of 3-methyl-3-oxetanemethanol (29.0 g) was dissolved in anhydrous dichloromethane (300 ml) and the solution was cooled to 0-5° C. Boron trifluoride diethyl etherate (2.83 ml) was added and the mixture was stirred for four hours at 0-5° C. Triethylamine (13.7 ml) was added and the mixture was stirred for 15 minutes at 0-5° C. The solvent was distilled off under reduced pressure. The residue was dissolved in ethyl ether (400 ml) and the solution was filtered. Next the solvent was distilled off under reduced pressure. Yield 28.0 g.

III. Synthesis of 4-ARM-PEG$_{20K}$-Decanoic Acid

A solution of pentaerythitol-based 4-ARM-PEG$_{20K}$-OH (20.0 g, 0.004 equivalents) (NOF Corporation) in anhydrous toluene (200 ml) was azeotropically dried by distilling off toluene. The dried product was dissolved in anhydrous toluene (400 ml) and 1.0 M solution of potassium tert-butoxide in tert-butanol (12 ml, 0.012 moles) and 1-(9-bromononyl)-4-methyl-2,6,7-trioxabicyclo[2,2,2]octane (4.0 g, 0.012 moles) were added and the mixture was stirred overnight at 72° C. under argon atmosphere. The solvent was distilled off under reduced pressure and the residue was dissolved in distilled water (300 ml). The pH of the solution was adjusted to 2 with 10% phosphoric acid and the solution was stirred for 45 minutes at room temperature. Next, the pH was readjusted to 12.5 by addition of 1M sodium hydroxide, and the solution was stirred for three hours keeping the pH at 12.1-12.5 by periodic addition of 1M sodium hydroxide. Thereafter, the pH was adjusted to 3 by addition of 10% phosphoric acid and the product was extracted with dichloromethane.

The extract was dried over anhydrous magnesium sulfate, filtered, concentrated under reduced pressure and then precipitated with isopropyl alcohol. The precipitated product was removed by filtration and dried under reduced pressure, then it was dissolved in dichloromethane (15 ml) and reprecipitated with isopropyl alcohol. Yield: 15.5 g.

$^1$H NMR (d$_6$-DMSO): δ 1.24 ppm (m, —CH$_2$—CH$_2$—CH$_2$—CH$_2$—CH$_2$—CH$_2$—CH$_2$—CH$_2$—CH$_2$—COO—), 1.46 ppm (m, —CH$_2$—CH$_2$—CH$_2$—CH$_2$—CH$_2$—CH$_2$—CH$_2$—CH$_2$—CH$_2$—COO—), 2.14 ppm (t, —CH$_2$—COO—), 3.51 ppm (s, PEG backbone). Substitution=~100% (meaning that each OH-group located on the ends of each arm of the 4-ARM-PEG starting material was converted to the corresponding decanoic acid).

Example 10

Synthesis of 4-ARM-PEG$_{20K}$-β-Methylpentanoic Acid ("4-ARM-PEG$_{20K}$-β-MPA")

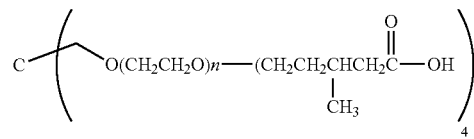

I. Synthesis of β-Methyl-δ-valerolactone

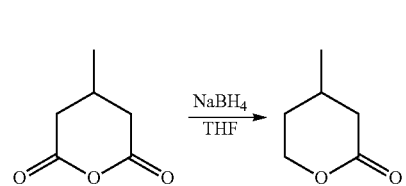

To a suspension of sodium borohydride (8.0 g) in anhydrous tetrahydrofuran (160 ml), cooled to 0-5° C., a solution of 3-methylglutaric anhydride (25.6 g) in anhydrous tetrahydrofuran (80 ml) was added and the mixture was stirred overnight at room temperature. Next, the mixture was cooled to 0-5° C. and hydrochloric acid (20% solution, 80 ml) was added during 40 minutes. The mixture was stirred for 15 minutes at 0-5° C. and at four hours h at room temperature, next it was concentrated under reduced pressure, filtered, and the crude product was extracted with chloroform. The extract was dried with anhydrous MgSO₄ and the solvent was distilled under reduced pressure.

The crude product was purified by vacuum distillation collecting the fraction boiling at 78° C. at 2.6 mm Hg. Yield 13.1 g. NMR~100% pure product.

II. Synthesis of 5-Bromo-3-Methylpentanoic Acid

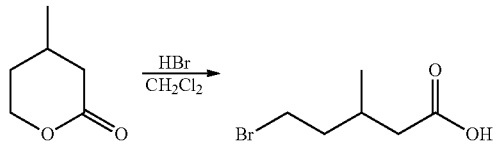

A solution of β-methyl-δ-valerolactone (3.0 g) in anhydrous dichloromethane (30 ml), cooled to 0-5° C., was saturated with hydrogen bromide gas and the mixture was stirred for three days at room temperature. The mixture was diluted with dichloromethane (100 ml) and the resulting solution was washed with 10-% NaCl (3×30 ml). Next the solution was dried with anhydrous MgSO₄ and the solvent was distilled under reduced pressure, Yield: 4.6 g. NMR 100% pure product.

III. Synthesis of 5-Bromo-3-Methylpentanoate Ester of 3-Methyl-3-Oxetanemethanol

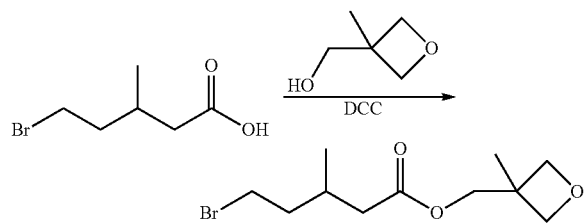

To a solution of 5-bromo-3-methylpentanoic acid (4.6 g, 0.024 moles), 3-methyl-3-oxetanemethanol (2.65 g, 0.026 moles), and 1-hydroxybenzotriazole (0.40 g) in anhydrous dichloromethane (100 ml) cooled to 0-5° C., a solution of N,N'-dicycloxehyldicarbodiimide (5.35 g, 0.026 moles) in anhydrous dichloromethane (20 ml) was added dropwise during 5 min. Next 4-(dimethylamino)pyridine (0.045 g) was added and the mixture was stirred overnight at room temperature under argon atmosphere. The solution was filtered and washed two times with 5-% phosphoric acid (2×50 ml). Next it was dried with anhydrous MgSO₄ and the solvent was distilled off. Yield 5.4 g. NMR purity~95%.

IV. Synthesis of 1-(4-bromo-2-methylbutyl)-4-methyl-2,6,7 trioxabicyclo [2,2,2]octane

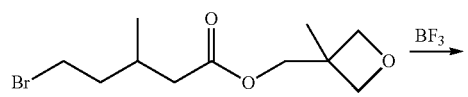

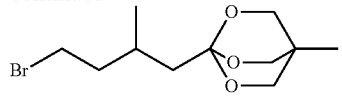

5-Bromo-3-methylpentanoate ester of 3-methyl-3-oxetanemethanol (5.4 g) was dissolved in anhydrous dichloromethane (400 ml) and the solution was cooled to 0-5° C. Boron trifluoride diethyl etherate (0.7 ml) was added and the mixture was stirred for four hours at 0-5° C. Triethylamine (3.4 ml) was added and the mixture was stirred for 15 minutes at 0-5° C. The solvent was distilled off under reduced pressure. The residue was dissolved in ethyl ether (50 ml) and the solution was filtered. Next the solvent was distilled off under reduced pressure. Yield: 4.6 g.

V. Synthesis of 4-ARM-PEG$_{20K}$-α-Methylpentanoic Acid

A solution of pentaerythritol-based 4-ARM-PEG$_{20K}$-OH (7.5 g, 0.0015 equivalents) (NOF Corporation) in anhydrous toluene (37.5 ml) was azeotropically dried by distilling off toluene. The dried product was dissolved in anhydrous toluene (37.5 ml) and 1.0 M solution of potassium tert-butoxide in tert-butanol (9 ml, 0.0090 moles) and 1-(4-bromo-2-butyl)-4-methyl-2,6,7-trioxabicyclo[2,2,2]octane (2.3 g, 0.0083 moles) were added and the mixture was stirred overnight at 70° C. under argon atmosphere. The solvent was distilled off under reduced pressure and the residue was dissolved in distilled water (100 ml). The pH of the solution was adjusted to 2 with 10% phosphoric acid and the solution was stirred for 15 minutes at room temperature. Next, the pH was readjusted to 12.5 by addition of 1M sodium hydroxide, and the solution was stirred for three hours keeping the pH at 12.1-12.5 by periodic addition of 1M sodium hydroxide. Thereafter, the pH was adjusted to 3 by addition of 10% phosphoric acid and the product was extracted with dichloromethane. The extract was dried over anhydrous magnesium sulfate, filtered, concentrated under reduced pressure and then precipitated with isopropyl alcohol. The precipitated product was removed by filtration and dried under reduced pressure. Yield: 3.2 g.

$^1$H NMR (D₂O): δ 0.88 ppm (d, —CH₃), 1.44 ppm and 1.56 ppm (m, —CH₂—CH₂—CH(CH₃)—CH₂—COO—), 1.93 ppm (m, CH—CH₃), 2.11 ppm and 2.31 ppm (m, —CH₂—COO—), 3.24 ppm (s, —OCH₃), 3.51 ppm (s, PEG backbone). Substitution=~75.5%.

Example 11

Characterization of Conjugates

The extent of drug substitution for various multi-arm conjugates of docetaxel is summarized below, as determined by $^1$H NMR.

Drug substitution: Calculation of drug substitution by $^1$H NMR

Samples of different 4-ARM-PEG-Docetaxel conjugates in deuterated chloroform (CDCl₃) were analyzed by $^1$H NMR, and the integral of the polymer backbone was compared with that of aromatic protons of docetaxel at 8.10 ppm. Based upon the averaged proton peak integration of all spectra obtained, the extent of drug substitution was determined.

TABLE 1

| Conjugate | NMR % (percent substitution) |
|---|---|
| 4-ARM-PEG$_{20K}$-GLY-DOC | (74% or on average 3 molecules drug per multi-arm polymer) |
| 4-ARM-PEG$_{10K}$-GLY-DOC | (81% or on average 3.2 molecules drug per multi-arm polymer) |
| 4-ARM-PEG$_{20K}$-BA-DOC | (95%* or on average 3.8 molecules drug per multi-arm polymer) |

*Drug substitution values average about 98% substitution for the BA-linked conjugate, 4-ARM-PEG$_{20K}$-BA-DOC (95-100%).

Example 12

Synthesis of Additional Multi-Armed Polymer Alkanoate-Linked Docetaxel Conjugates The following 4-ARM-PEG$_{20K}$-alkanoic acids were prepared as described in Example 1: 4-ARM-PEG$_{20K}$-α-methylpropionic acid (4-ARM-PEG$_{20K}$-MPA), 4-ARM-PEG$_{20K}$-hexanoic acid (4-ARM-PEG$_{20K}$-HA), 4-ARM-PEG$_{20K}$-octanoic acid (4-ARM-PEG$_{20K}$-OA), and 4-ARM-PEG$_{20K}$-decanoic acid (4-ARM-PEG$_{20K}$-DA). The following multi-armed butanoic acids were also prepared: 4-ARM-PEG$_{10K}$-butanoic acid (4-ARM-PEG$_{10K}$-BA), 4-ARM-PEG$_{30K}$-butanoic acid (4-ARM-PEG$_{30K}$-BA), and 4-ARM-PEG$_{40K}$-butanoic acid (4-ARM-PEG$_{40K}$-BA). Detailed descriptions of the synthesis follow as Examples 12A-C respectively.

Docetaxel (1.03 g, 1.20 mmol), the corresponding 4-ARM-PEG$_{20K}$-Acid [α-methylpropionic acid (4-ARM-PEG$_{20K}$-MPA), 4-ARM-PEG$_{20K}$-hexanoic acid (4-ARM-PEG$_{20K}$-HA), 4-ARM-PEG$_{20K}$-octanoic acid (4-ARM-PEG$_{20K}$-OA), 4-ARM-PEG$_{20K}$-decanoic acid (4-ARM-PEG$_{20K}$-DA), 4-ARM-PEG$_{10K}$-butanoic acid (4-ARM-PEG$_{10K}$-BA), 4-ARM-PEG$_{30K}$-butanoic acid (4-ARM-PEG$_{10K}$-BA), or 4-ARM-PEG$_{40K}$-butanoic acid (4-ARM-PEG$_{40K}$-BA), 0.25 mmol], and DPTS (0.15 g, 0.50 mmol) were dissolved in 50 mL DCM. The resulting solution was cooled in an ice-salt (NaCl) bath (−15 to −5° C.) for 20 minutes. Before DIC (0.38 g, 3.00 mmol, in 5 mL of DCM) was added with stirring. The reaction mixture was stirred for an additional 12 hours at −15 to −5° C. The solution was filtered to remove any solids and then concentrated under reduced pressure to half the volume. The resulting solution was slowly added to 400 mL of ether/IPA (1:1) with stirring. The white solid was collected and precipitated again using the above method. The product was dried in vacuo (yield: approximately 90% for all syntheses).

4-ARM-PEG$_{20K}$-MPA-Docetaxel: $^1$H NMR (300 MHz, CDCl$_3$): δ 1.02-1.20 (m, 2414), 1.21 (s, 12H), 1.32 (s, 36H), 1.65 (d, 4H), 1.74 (s, 12H), 1.85 (m, 4H), 1.93 (s, 12H), 2.10-2.38 (m, 8H), 2.41 (s, 12H), 2.60 (m, 4H), 2.80 (m, 4H), 3.30-3.92 (m, ~2180 H), 4.10-4.30 (m, 23H), 4.95 (d, 4H), 5.21 (s, 4H), 5.47 (m, 4H), 5.52 (br., 10H), 6.21 (t, 4H), 7.26 (m, 8H), 7.40 (m, 8H), 7.50 (m, 8H), 7.60 (m, 4H), 8.12 (d, 8H).

4-ARM-PEG$_{20K}$-HA-Docetaxel: $^1$H NMR (300 MHz, CDCl$_3$): δ 1.12 (s, 12H), 1.22 (s, 12H), 1.32 (s, 36H), 1.34-1.70 (m, 15H), 1.74 (s, 12H), 1.80-1.95 (m, 16H), 2.10-2.38 (m, 16H), 2.43 (s, 12H), 2.60 (m, 4H), 3.30-3.90 (m, ~1950H), 3.91 (d, 4H), 4.12-4.26 (m, 8H), 4.30 (d, 4H), 4.97 (d, 4H), 5.28 (s, 4H), 5.25-5.55 (m, 10H), 5.68 (d, 4H), 6.21 (t, 4H), 7.26 (m, 8H), 7.40 (m, 8H), 7.50 (m, 8H), 7.60 (m, 4H), 8.11 (d, 8H).

4-ARM-PEG$_{20K}$-OA-Docetaxel $^1$H NMR (300 MHz, CDCl$_3$): δ 1.11 (s, 12H), 1.13-1.24 (m, 40H), 1.33 (s, 36H), 1.40-1.60 (m, 18H), 1.74 (m, 12H), 1.83-2.00 (m, 16H), 2.00-2.20 (m, 4H), 2.220-2.40 (m, 13H), 2.43 (s, 12H), 2.60 (br., 4H), 3.32-3.89 (m, ~2180H), 3.90 (d, 4H), 4.12-4.20 (m, 12H), 4.26 (d, 4H), 4.96 (d, 4H), 5.21 (s, 4H), 5.38 (m, 8H), 5.50 (br. 4H), 5.68 (d, 4H), 6.23 (t, 4H), 7.24 (m, 8H), 7.38 (m, 8H), 7.50 (m, 8H), 7.61 (m, 4H), 8.12 (d, 8H).

4-ARM-PEG$_{20K}$-DA-Docetaxel $^1$H NMR (300 MHz, CDCl$_3$): δ 1.11 (s, 12H), 1.22 (s, 12H), 1.23-1.30 (m, 44H), 1.33 (s, 36H), 1.40-1.60 (m, 18H), 1.74 (m, 12H), 1.84-2.00 (m, 16H), 2.00-2.20 (m, 4H), 2.20-2.40 (m, 13H), 2.43 (s, 12H), 2.60 (br., 4H), 3.30-3.88 (m, ~2100H), 3.90 (d, 4H), 4.12-4.20 (m, 12H), 4.26 (d, 4H), 4.96 (d, 4H), 5.21 (s, 4H), 5.38 (m, 8H), 5.50 (br. 4H), 5.68 (d, 4H), 6.23 (t, 4H), 7.24 (m, 8H), 7.38 (m, 8H), 7.50 (m, 8H), 7.61 (m, 4H), 8.12 (d, 8H).

4-ARM-PEG$_{10K}$-BA-Docetaxel $^1$H NMR (500 MHz, CDCl$_3$): δ 1.10 (s, 12H), 1.21 (s, 12H), 1.33 (s, 36H), 1.74 (s, 12H), 1.85 (m, 12H), 1.94 (m, 12H), 2.15 (m, 4H), 2.30 (m, 4H), 2.41 (m, 15H), 2.55 (m, 8H), 3.30-3.80 (m, ~960H), 3.90 (d, 4H), 4.18 (m, 8H), 4.25 (m, 4H), 4.30 (d, 4H), 4.97 (d, 4H), 5.19 (s, 4H), 5.30 (s, 4H), 5.45 (m, 8H), 5.64 (d, 4H), 6.30 (t, 4H), 7.24 (m, 8H), 7.35 (m, 8H), 7.49 (m, 8H), 7.60 (m, 4H), 8.01 (d, 8H).

4-ARM-PEG$_{30K}$-BA-Docetaxel $^1$H NMR (500 MHz, CDCl$_3$): δ 1.11 (s, 12H), 1.21 (s, 12H), 1.33 (s, 36H), 1.74 (s, 12H), 1.85 (m, 12H), 1.94 (m, 12H), 2.15 (m, 4H), 2.30 (m, 4H), 2.41 (m, 15H), 2.55 (m, 8H), 3.30-3.80 (m, ~2840H), 3.90 (d, 4H), 4.18 (m, 8H), 4.25 (m, 4H), 4.30 (d, 4H), 4.97 (d, 4H), 5.19 (s, 4H), 5.30 (s, 4H), 5.45 (m, 8H), 5.64 (d, 4H), 6.30 (t, 4H), 7.24 (m, 8H), 7.35 (m, 8H), 7.49 (m, 8H), 7.60 (m, 4H), 8.01 (d, 8H).

4-ARM-PEG$_{40K}$-BA-Docetaxel $^1$H NMR (500 MHz, CDCl$_3$): δ 1.11 (s, 12H), 1.21 (s, 12H), 1.33 (s, 36H), 1.74 (s, 12H), 1.85 (m, 1214), 1.94 (m, 12H), 2.15 (m, 4H), 2.30 (m, 4H), 2.41 (m, 15H), 2.55 (m, 8H), 3.30-3.80 (m, ~4050H), 3.90 (d, 4H), 4.18 (m, 8H), 4.25 (m, 4H), 4.30 (d, 4H), 4.97 (d, 4H), 5.19 (s, 4H), 5.30 (s, 4H), 5.45 (m, 8H), 5.64 (d, 4H), 6.30 (t, 4H), 7.24 (m, 8H), 7.35 (m, 8H), 7.49 (m, 8H), 7.60 (m, 4H), 8.09 (d, 8H).

Example 12A

Synthesis of 4-ARM-PEG$_{10K}$-Butanoic Acid ("4-ARM-PEG$_{10K}$-BA")

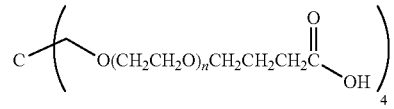

A solution of pentaerythritol-based 4-ARM-PEG$_{10K}$-OH (50.0 g, 0.020 equivalents) (NOF Corporation) in toluene (450 ml) was azeotropically dried by distilling off 100 ml of toluene. A 1.0M solution of potassium tert-butoxide in tert-butanol (50 ml, 0.050 moles) and 1-(3-bromopropyl)-4-methyl-2,6,7-trioxabicyclo[2,2,2]octane (14.0 g, 0.056 moles) was added and the mixture was stirred overnight at 70° C. under argon atmosphere. The solvent was distilled off under reduced pressure and the residue was dissolved in distilled water (600 ml). The pH of the solution was adjusted to 2 with 5% phosphoric acid and the solution was stirred for 15 minutes at room temperature. Next, the pH was readjusted to 12 by addition of 1M sodium hydroxide, and the solution was stirred for two hours keeping the pH at 12 by periodic addition of 1M sodium hydroxide. Thereafter, the pH was adjusted to 3 by addition of 5% phosphoric acid and the product was extracted with dichloromethane.

The extract was dried over anhydrous magnesium sulfate, filtered, and then added to isopropyl alcohol. The precipitated product was removed by filtration and dried under reduced pressure.

Yield: 45.0 g. $^1$H NMR (d$_6$-DMSO): δ 1.72 ppm (q, C$\underline{H}_2$—CH$_2$—COO—), 2.24 ppm (t, —CH$_2$—COO—), 3.51 ppm (s, PEG backbone). Substitution=~100% (meaning that each OH— group located on the end of each arm of the 4-ARM-PEG starting material was converted to the corresponding butanoic acid).

Example 12B

Synthesis of 4-ARM-PEG$_{30k}$-Butanoic Acid ("4-ARM-PEG$_{30K}$-BA")

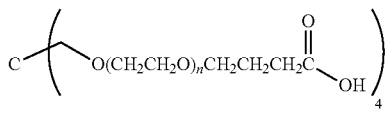

A solution of pentaerythritol-based 4-ARM-PEG$_{30k}$-OH (50.0 g, 0.0067 equivalents) (ChemOrganics, Houston Tex.) in toluene (450 ml) was azeotropically dried by distilling off 100 ml of toluene. A 1.0M solution of potassium tert-butoxide in tert-butanol (20 ml, 0.020 moles) and 1-(3-bromopropyl)-4-methyl-2,6,7-trioxabicyclo[2,2,2]octane (5.9 g, 0.023 moles) was added and the mixture was stirred overnight at 70° C. under argon atmosphere. The solvent was distilled off under reduced pressure and the residue was dissolved in distilled water (600 ml). The pH of the solution was adjusted to 2 with 5% phosphoric acid and the solution was stirred for 15 minutes at room temperature. Next, the pH was readjusted to 12 by addition of 1M sodium hydroxide, and the solution was stirred for two hours keeping the pH at 12 by periodic addition of 1M sodium hydroxide. Thereafter, the pH was adjusted to 3 by addition of 5% phosphoric acid and the product was extracted with dichloromethane, The extract was dried over anhydrous magnesium sulfate, filtered, and then added to isopropyl alcohol. The precipitated product was removed by filtration and dried under reduced pressure.

Yield: 46 g. $^1$H NMR (d$_6$-DMSO): δ 1.72 ppm (q, C$\underline{H}_2$—CH$_2$—COO—), 2.24 ppm (t, —CH$_2$—COO—), 3.51 ppm (s, PEG backbone). Substitution=~100% (meaning that each OH-group located on the ends of each arm of the 4-ARM-PEG starting material was converted to the corresponding butanoic acid).

Example 12C

Synthesis of 4-ARM-PEG$_{40k}$-Butanoic Acid ("4-ARM-PEG$_{40k}$-BA")

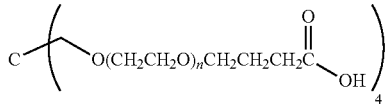

A solution of pentaerythritol-based 4-ARM-PEG$_{40K}$-OH (50.0 g, 0.005 equivalents) (NOF Corporation) in toluene (450 ml) was azeotropically dried by distilling off 100 ml of toluene. A 1.0M solution of potassium tert-butoxide in tert-butanol (15 ml, 0.015 moles) and 1-(3-bromopropyl)-4-methyl-2,6,7-trioxabicyclo[2,2,2]octane (4.4 g, 0.018 moles) was added and the mixture was stirred overnight at 70° C. under argon atmosphere. The solvent was distilled off under reduced pressure and the residue was dissolved in distilled water (600 ml). The pH of the solution was adjusted to 2 with 5% phosphoric acid and the solution was stirred for 15 minutes at room temperature. Next, the pH was readjusted to 12 by addition of 1M sodium hydroxide, and the solution was stirred for two hours keeping the pH at 12 by periodic addition of 1M sodium hydroxide. Thereafter, the pH was adjusted to 3 by addition of 5% phosphoric acid and the product was extracted with dichloromethane.

The extract was dried over anhydrous magnesium sulfate, filtered, and then added to isopropyl alcohol. The precipitated product was removed by filtration and dried under reduced pressure.

Yield: 48.0 g. $^1$H NMR (d$_6$-DMSO): δ 1.72 ppm (q, C$\underline{H}_2$—CH$_2$—COO—), 2.24 ppm (t, —CH$_2$—COO—), 3.51 ppm (s, PEG backbone). Substitution=~100% (meaning that each OH— group located on the ends of each arm of the 4-ARM-PEG starting material was converted to the corresponding butanoic acid).

Example 13

Anti-Tumor Activity of 4-ARM-PEG$_{70K}$-BA-docetaxel in Mouse Xenograft Models of Human Lung and Colon Cancer The purpose of the following studies was to evaluate the anti-tumor activity of 4-ARM-PEG$_{20K}$-BA-DOC in non-small cell lung (H460) and colorectal (LS174T, LoVo) mouse tumor xenograft models exhibiting limited docetaxel sensitivity.

H460, LS174T and LoVo tumors were established in female athymic nude mice. Groups of 10 mice received a total of three single doses of 4-ARM-PEG$_{20K}$-BA-DOC or docetaxel administered every 7 days (q7dx3) at several doses up to a maximum tolerated dose (MTD). Control groups received no treatment after tumor implant. Animals were weighed daily for the first five days and twice weekly thereafter. Tumor volumes were measured twice weekly after the first drug injection.

Tumor endpoint volume was 1500 mm$^3$ for LS174T, 1000 mm$^3$ for LoVo, and 2000 mm$^3$ for H460.

Anti-tumor activity was measured as changes in tumor volume, time to reach endpoint, and complete or partial tumor regression.

Treatment outcome was evaluated by Tumor Growth Delay (TGD), which is defined as the increase in median time to endpoint in a treatment group compared to the control group. Here it is expressed as % TGD, as a percentage to the median time to endpoint of the control group.

A tumor whose volume was reduced to 50% or less for three consecutive measurements compared to its volume on Day 1 was considered to be in partial regression. Complete regression was defined as volume equal to or greater than 13.5 mm$^3$ for three consecutive measurements.

Acceptable toxicity was defined as a group mean body weight (BW) loss of less than 20% during the study and not more than one treatment-related death among ten treated animals. Any dosing regimen that resulted in greater toxicity was considered above the maximum tolerated dose (MTD).

Results were as follows.

Figure 3A:
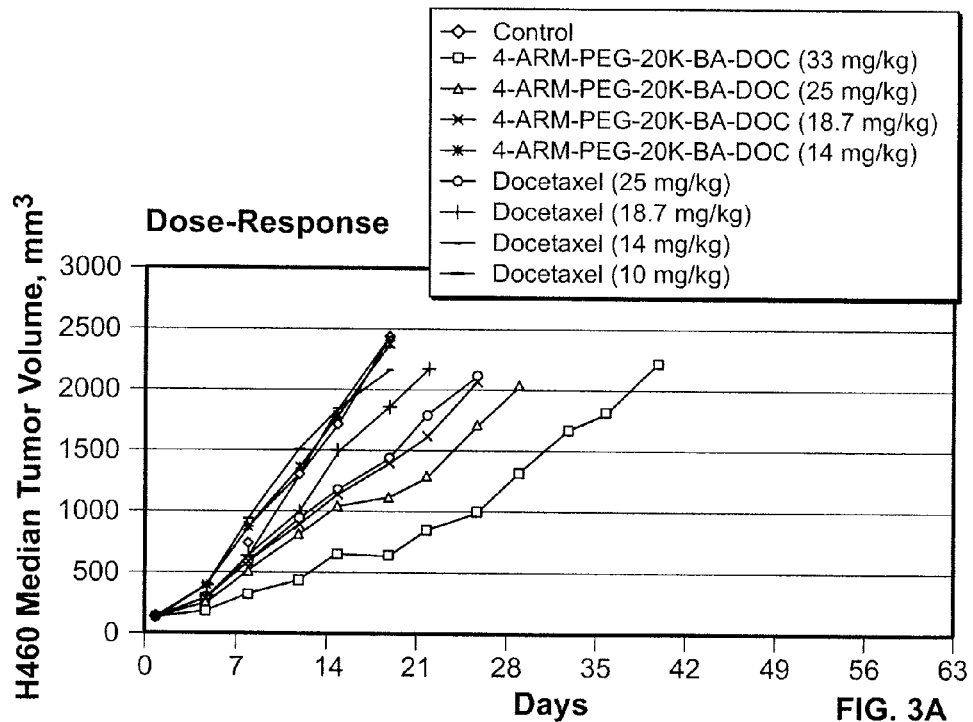
FIGS. 3A and 3B illustrate significantly increased tumor growth delay (TGD) for mice implanted with H460 tumors and treated with either docetaxel (Taxotere®) or 4-ARM-$PEG_{20K}$-BA-DOC as described in detail in Example 13.
Figure 3B:
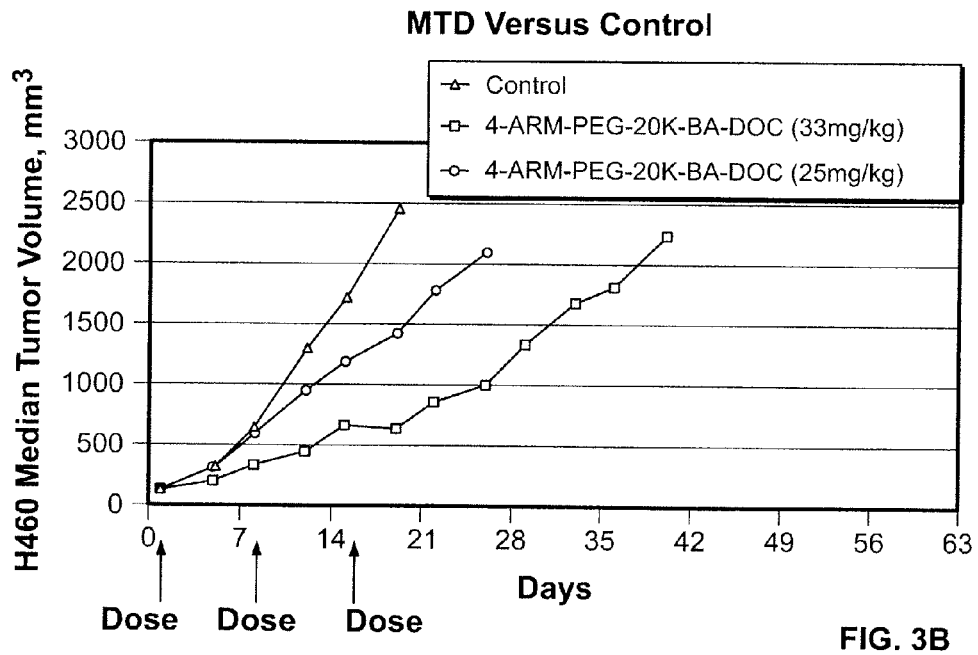

Non-small cell lung cancer model (H460): 4-ARM-PEG$_{20K}$-BA-DOC treatment resulted in a statistically significant (p<0.05), dose-related increase in tumor growth delay (TGD) in H460 tumor bearing mice at MTD (33 mg/kg 4-ARM-PEG$_{20K}$-BA-DOC, 25 mg/kg docetaxel) with % TGD values of 122% and 48% in 4-ARM-PEG$_{20K}$-BA-DOC and docetaxel treated groups, respectively. See FIGS. 3A (all dosage groups) and 3B (control and MTD groups only) as well as Table 2A below. Decreases in body weight were comparable between 4-ARM-PEG$_{20K}$-BA-DOC and docetaxel at MTD (14.2% and 15.5%, respectively).

To assess whether the improved antitumor activity was due to greater plasma and tumor docetaxel exposure following 4-ARM-PEG$_{20K}$-BA-DOC administration, plasma and tumor homogenates were analyzed after a single IV administration of 4-ARM-PEG$_{20K}$-BA-DOC or docetaxel in mice bearing H460 tumors. In looking at each of 4-ARM-PEG$_{20K}$-BA-DOC and docetaxel dosed at their respective maximum tolerated doses (MTDs) of 33 and 25 mg/kg, the following was observed. After 4-ARM-PEG$_{20K}$-BA-DOC administration, plasma docetaxel concentrations remained above 5 ng/mL for as long as 168 hr, whereas docetaxel concentrations fell below 1 ng/mL by 72 hr after docetaxel administration. The maximum plasma docetaxel concentration with 4-ARM-PEG$_{20K}$-BA-DOC was 13-fold lower than that with docetaxel. While both treatments achieved a similar plasma docetaxel area under the concentration-time curve (AUC), 4-ARM-PEG$_{20K}$-BA-DOC treatment resulted in tumor docetaxel concentrations that were 0.4 to 4-fold higher than those for docetaxel, leading to a 2-fold greater tumor docetaxel AUC. This greater and sustained tumor exposure to docetaxel after 4-ARM-PEG$_{20K}$-BA-DOC administration was associated with significantly longer tumor growth delay over docetaxel (122% vs 48%). 4-ARM-PEG$_{20K}$-BA-DOC retained significant antitumor activity at 19 mg/kg (58% of its MTD), whereas docetaxel doses less than 25 mg/kg did not.

TABLE 2A

Response Summary Following Treatment with 4-ARM-PEG$_{20K}$-BA-DOC and Docetaxel in H460 Xenografts

| Treatment Group | Dose (mg/kg) | Dose (mg/m²) | TGD[1] (%) | BW Loss (%)/Day of BW Nadir | No. Surviving/ No. Treated Mice |
|---|---|---|---|---|---|
| No Treatment | 0 | 0 | — | 0/0[2] | 10/10 |
| Docetaxel | 10 | 30 | −2 | 0/0 | 10/10 |
| | 14 | 42 | 4 | 4.1/19 | 10/10 |
| | 18.7 | 56.1 | 23 | 9.7/22 | 10/10 |
| | 25 | 75 | 48* | 15.5/26 | 10/10 |
| 4-ARM-PEG$_{20K}$-BA-DOC | 14 | 42 | −1 | 0/0 | 10/10 |
| | 18.7 | 56.1 | 56* | 6.2/22 | 10/10 |
| | 25 | 75 | 72** | 10.4/29 | 10/10 |
| | 33.3 | 99.9 | 122** | 14.2/22 | 10/10 |

*p < 0.05 as compared to no treatment group.
**p < 0.01 as compared to no treatment group.
[1]Tumor growth delay is based on a study endpoint of either 2000 mm³ or 57-days.
[2]0/0 indicates no decrease in body weight was observed.
3 Statistical significance was not evaluated, since treatment exceeded MTD.

TABLE 2B

| Treatment | Dose (mg/kg)[&] | | Tumor growth delay (%) | AUC (hr * ng/mL) | | 4-ARM-PEG$_{20K}$-BA-DOC to Docetaxel Ratio | |
|---|---|---|---|---|---|---|---|
| | | | | Plasma | Tumor | Plasma | Tumor |
| Docetaxel | 25 | MTD | 48 | 6146 | 138,715 | — | — |
| 4-ARM-PEG$_{20K}$-BA-DOC | 33 | MTD | 122 | 6013 | 313,558 | 1.0 | 2.3 |
| | 19 | 58% MTD | 56 | 3488[#] | 181,864[#] | 0.6 | 1.3 |

[&]Administeied q7dx3
[#]Extrapolated from the 33 mg/kg dose.

Colon (LS174T) cancer model: TGD with 4-ARM-PEG$_{20K}$-BA-DOC treatment in LS174T tumor bearing mice was dose-related and resulted in three partial regressions (PR) at MTD; no partial regressions were observed with docetaxel. In LS174T tumor bearing mice, 4-ARM-PEG$_{20K}$-BA-DOC demonstrated a significantly (p<0.0001) greater TGD than docetaxel; 266% vs. 166% at MTD (40 mg/kg 4-ARM-PEG$_{20K}$-BA-DOC, 30 mg/kg docetaxel). At 30 mg/kg, 4-ARM-PEG$_{20K}$-BA-DOC demonstrated a 250% TGD and one partial regression while 30 mg/kg docetaxel resulted in 166% TGD and no regressions. Decreases in body weight were comparable between 4-ARM-PEG$_{20K}$-BA-DOC and docetaxel at MTD (18.8% and 16.6%, respectively).

Figure 2A:
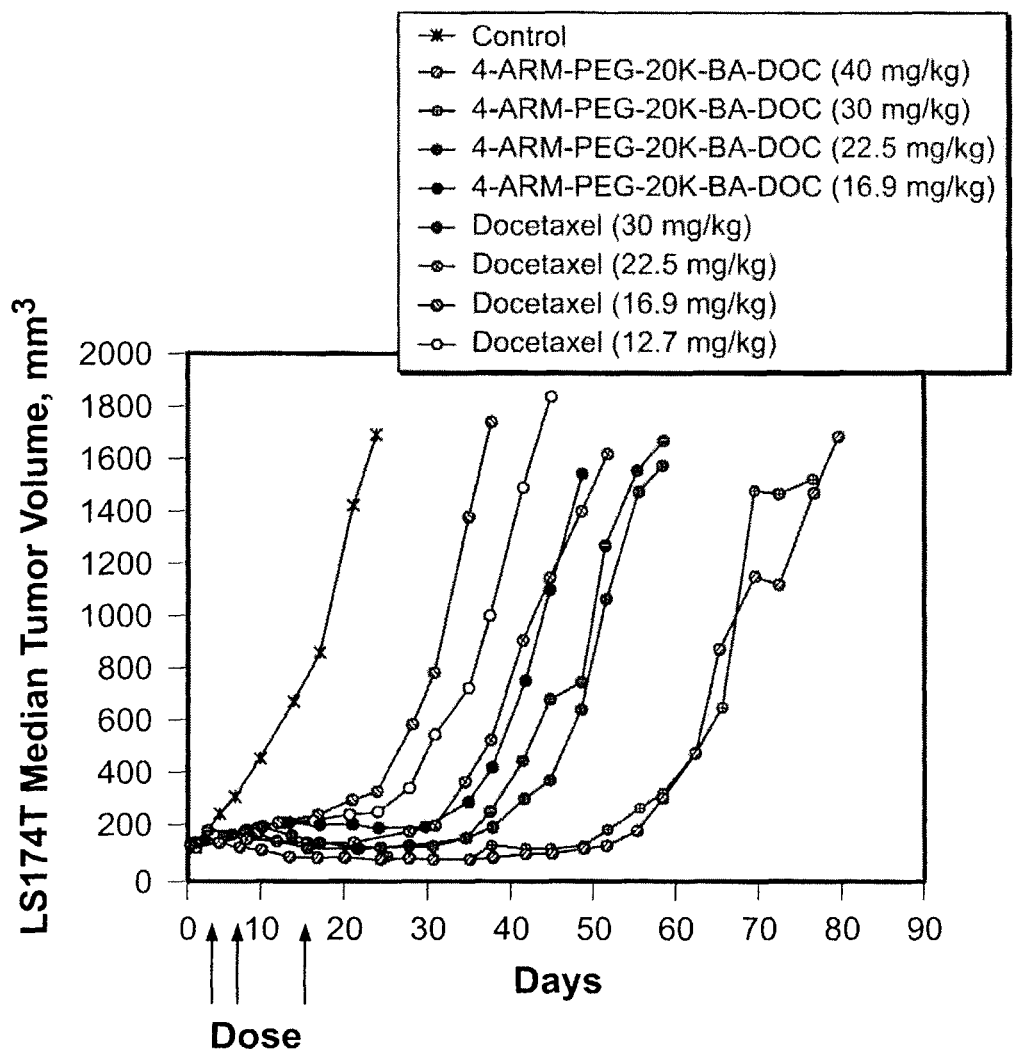
FIGS. 2A and 2B are graphs illustrating the median tumor volume (MTV) over time for mice implanted with LS174T (colorectal) tumors and treated with either docetaxel (Taxotere®) or 4-ARM-$PEG_{20K}$-BA-DOC as described in detail in Example 13.
Figure 2B:
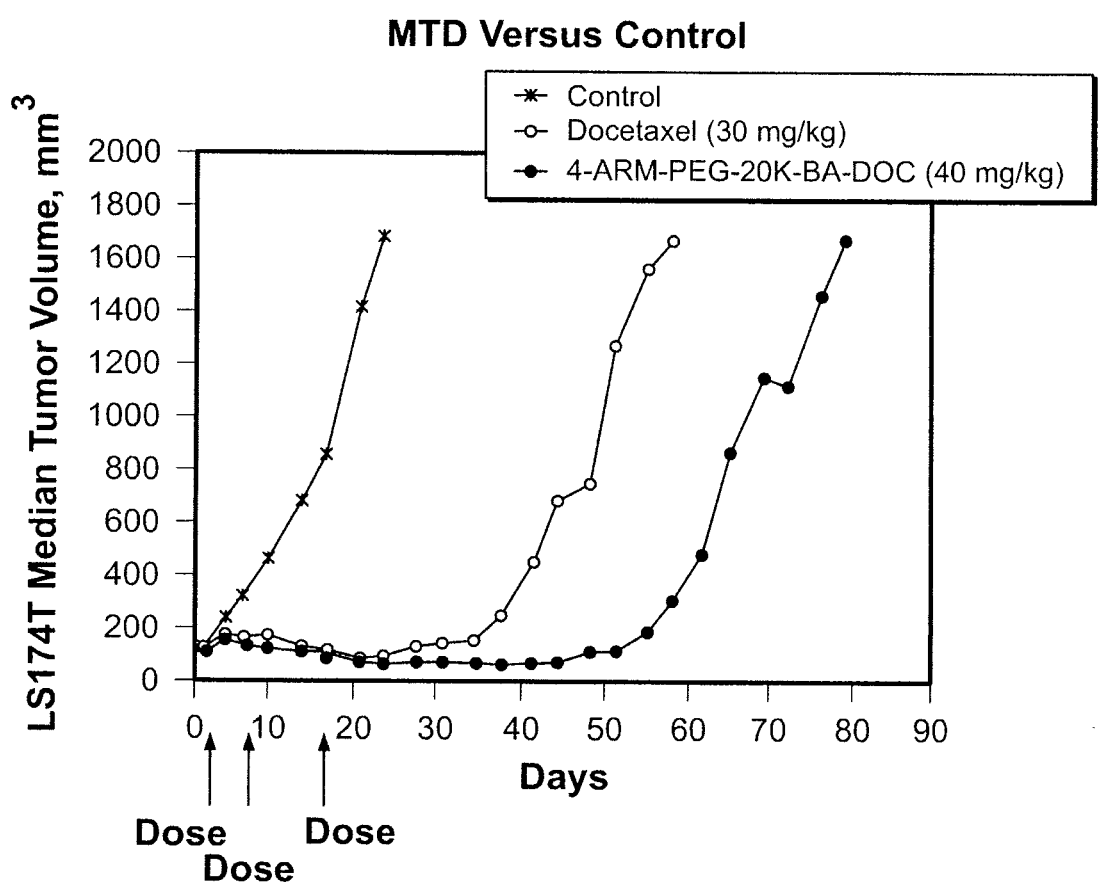

See FIGS. 2A and 2B and Table 3 below.

TABLE 3

Response Summary Following Treatment with 4-ARM-PEG$_{20K}$-BA-DOC and Docetaxel in LS174T Colon Cancer Xenografts

| Treatment Group | Dose (mg/kg) | Dose (mg/m²) | TGD[1] (%) | BW Loss (%)/Day of BW Nadir | No. Surviving/ No. Treated Mice |
|---|---|---|---|---|---|
| No Treatment | 0 | 0 | — | 0/0[2] | 10/10 |
| Docetaxel | 12.7 | 38.1 | 69* | 8.8/23 | 10/10 |
| | 16.9 | 50.7 | 96* | 11.2/23 | 10/10 |
| | 22.5 | 67.5 | 135* | 6.7/23 | 10/10 |
| | 30 | 90 | 166* | 16.6/23 | 10/10 |
| 4-ARM-PEG$_{20K}$-BA-DOC | 16.9 | 50.7 | 126* | 12.4/23 | 9/10 |
| | 22.5 | 67.5 | 169* | 11.1/23 | 10/10 |
| | 30 | 90 | 250* | 17.9/23 | 9/10 |
| | 40 | 120 | 266* | 18.8/23 | 10/10 |

| PR |
|---|
| 0 |
| 0 |
| 0 |
| 0 |
| 0 |
| 0 |
| 0 |
| 1 |
| 3 |

*p < 0.001 as compared to no treatment group.
[1]TGD based on a study endpoint of either 1500 mm³ or 79-days.
[2]0/0 indicates no decrease in body weight was observed.

Figure 4A:
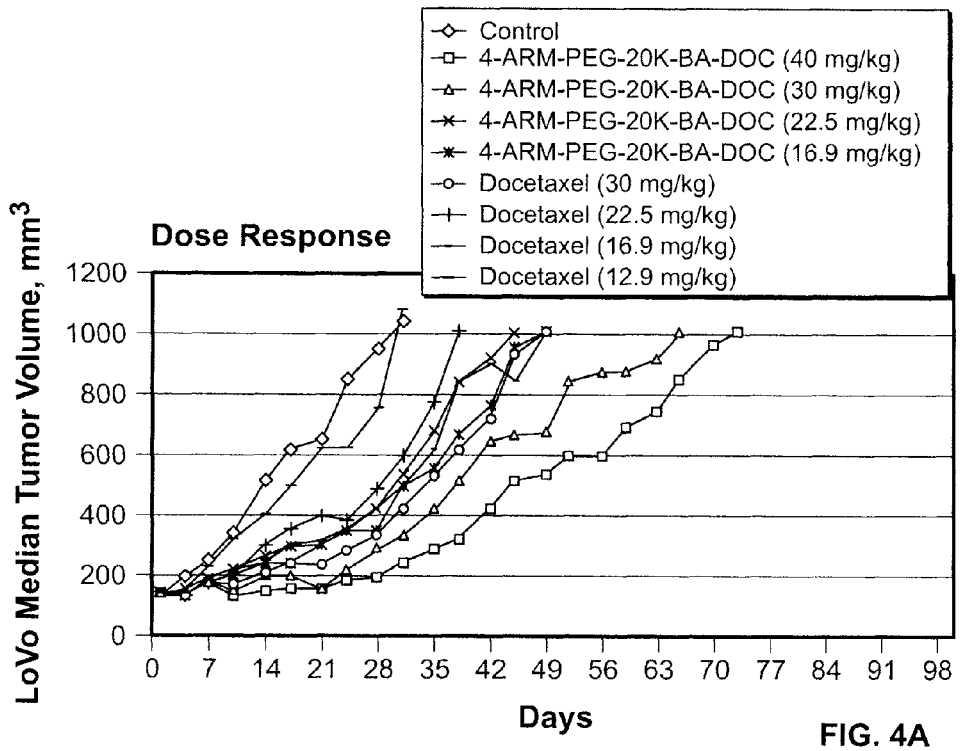
FIGS. 4A and 4B are graphs illustrating the median tumor volume over time for mice implanted with LoVo tumors and treated with either docetaxel (Taxotere®) or 4-ARM-$PEG_{20K}$-BA-DOC as described in detail in Example 13.
Figure 4B:
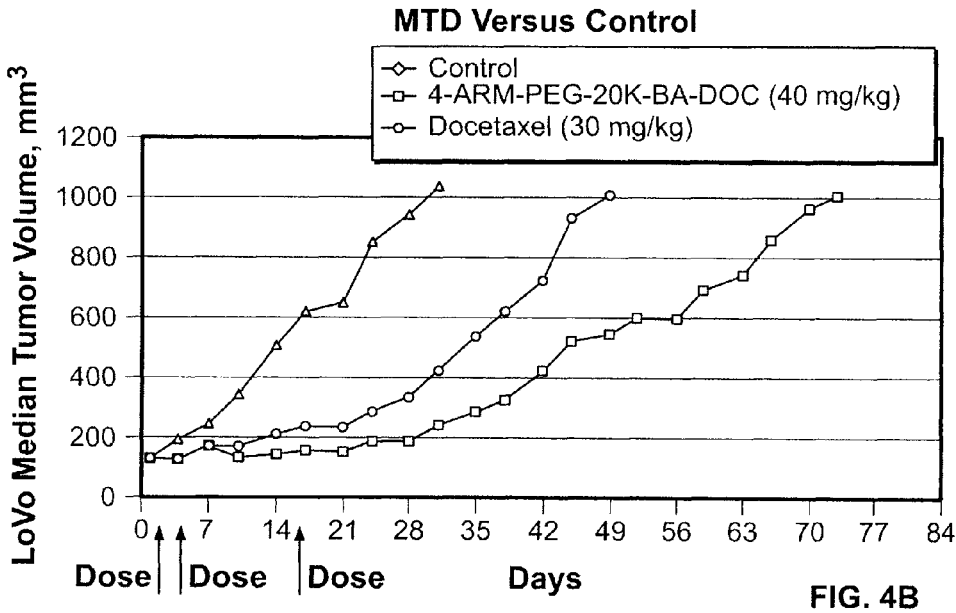

Colon (LoVo) cancer model: 4-ARM-PEG$_{20K}$-BA-DOC treatment in LoVo tumor bearing mice resulted in similar dose-related improvements in TGD. Body weight changes for 4-ARM-PEG$_{20K}$-BA-DOC treatment were generally less than or similar to those for docetaxel at the same equivalent dose. 40 mg/kg 4-ARM-PEG$_{20K}$-BA-DOC was in excess of the MTD due to a body weight decrease of 22.6% and resulted in a 148% TGD with two PRs. Although not significantly different, when administered at a docetaxel equivalent dose of 30 mg/kg, the MTD for both agents, 4-ARM-PEG$_{20K}$-BA-DOC resulted in twice the tumor growth delay compared to docetaxel (128% vs 64%). At the lower docetaxel equivalent doses (22.5 and 16.9 mg/kg), activity of 4-ARM-PEG$_{20K}$-BA-DOC and docetaxel was comparable. See FIGS. 4A and 4B.

TABLE 4

Response Summary Following Treatment with 4-ARM-PEG$_{20K}$-BA-DOC and Docetaxel in LoVo Xenografts

| Treatment Group | Dose (mg/kg) | Dose (mg/m²) | TGD[2] (%) | BW Loss (%)/Day of BW Nadir | PR | No. Surviving/ No. Treated Mice |
|---|---|---|---|---|---|---|
| No Treatment | 0 | 0 | — | 0/0[3] | 0 | 10/10 |
| Docetaxel | 12.7 | 38.1 | 7 | 5.0/24 | 0 | 10/10 |
|  | 16.9 | 50.7 | 70** | 12.8/21 | 0 | 10/10 |
|  | 22.5 | 67.5 | 32* | 14.6/24 | 0 | 10/10 |
|  | 30 | 90 | 64** | 13.3/21 | 0 | 10/10 |
| 4-ARM-PEG$_{20K}$-BA- | 16.9 | 50.7 | 64** | 7.0/21 | 0 | 10/10 |
|  | 22.5 | 67.5 | 50* | 11.0/24 | 0 | 10/10 | trates that the exemplary conjugate, 4-ARM-PEG$_{20K}$-BA-DOC, is effective at significantly improving the time-concentration profile and anti-tumor activity of docetaxel.

Example 14

Pharmacokinetics of Docetaxel and 4-ARM-PEG$_{20K}$-BA-docetaxel in Sprague-Dawley Rats The objective of this study was to assess the pharmacokinetics and excretion of docetaxel and 4-ARM-PEG$_{20K}$-BA-docetaxel after intravenous infusion to rats.

Pharmacokinetics of 4-ARM-PEG$_{20K}$-BA-docetaxel and docetaxel were evaluated in male rats (15 rats/dose level) dosed with 5, 10, and 15 mg/kg (30, 60, 90 mg/m²) 4-ARM-PEG$_{20K}$-BA-docetaxel or 5 mg/kg (30 mg/m²) docetaxel. 4-ARM-PEG$_{20K}$-BA-docetaxel and docetaxel were administered via a femoral vein catheter as 30-min intravenous infusions at 4 mL/kg. Blood samples (n=15 timepoints with n=5 samples/dose level/timepoint) were obtained by jugular venipuncture between pre-dose and 144 hours post-dose. Pharmacokinetic parameters are summarized in Table 5.

TABLE 5

Docetaxel and 4-ARM-PEG$_{20K}$-BA-docetaxel Pharmacokinetic Parameters in Male Rats after Single IV Doses of 5 mg/kg Docetaxel, or 5, 10, 15 mg/kg 4-ARM-PEG$_{20K}$-BA-docetaxel

| Treatment | Dose (mg/kg) | Analyte | $T_{1/2}$ (hr) | Tmax (hr) | Cmax (ng/mL) | AUClast (hr * ng/mL) | AUCinf (hr * ng/mL) | CL (mL/min/kg) | Vss (L/kg) |
|---|---|---|---|---|---|---|---|---|---|
| Docetaxel | 5 | Docetaxel | ND[1] | 0.5 | 682 | 1417 | ND | ND[2] | ND |
| Conjugate* | 5 | Docetaxel | ND | 0.5 | 122 | 1711 | ND | NA | NA |
|  |  | Conjugate | 73 | 0.5 | 40079 | 226203 | 250374 | 0.33 | 0.8 |
| Conjugate* | 10 | Docetaxel | ND | 2.0 | 176 | 3003 | ND | NA | NA |
|  |  | Conjugate | 59 | 0.5 | 70795 | 419132 | 437912 | 0.38 | 0.55 |
| Conjugate* | 15 | Docetaxel | ND. | 1.0 | 273 | 3743 | ND | NA | NA |
|  |  | Conjugate | 63 | 0.5 | 138296 | 847993 | 895159 | 0.28 | 0.47 |
| Average Conjugate (±SD) |  |  | 65 ± 7 |  |  |  |  | 0.33 ± 0.05 | 0.61 ± 0.17 |

[1]ND = not determined; terminal phase not well defined
[2]NA = not applicable for the docetaxel metabolite
*Conjugate = 4-ARM-PEG$_{20K}$-BA-docetaxel TABLE 4-continued Response Summary Following Treatment with 4-ARM-PEG$_{20K}$-BA-DOC and Docetaxel in LoVo Xenografts

| Treatment Group | Dose (mg/kg) | Dose (mg/m²) | TGD[2] (%) | BW Loss (%)/Day of BW Nadir | PR | No. Surviving/ No. Treated Mice |
|---|---|---|---|---|---|---|
| DOC | 30 | 90 | 128** | 16.2/24 | 0 | 10/10 |
|  | 40 | 120 | 1481 | 22.6/24 | 2 | 10/10 |

*p < 0.01
***p < 0.001 as compared to no treatment group.
[1]Statistical significance was not evaluated, since treatment exceeded MTD.
[2]TGD based on a study endpoint of 1000 mm³ or 77-days.
[3]0/0 indicates no decrease in body weight was observed.

The foregoing illustrates that 4-ARM-PEG$_{20K}$-BA-DOC possesses significantly greater anti-tumor activity than docetaxel in H460 and LS174T mouse xenograft models. Partial regressions were observed in two of the three cell lines for 4-ARM-PEG$_{20K}$-BA-DOC while no regressions were observed for docetaxel. At MTD, the % TGDs for 4-ARM-PEG$_{20K}$-BA-DOC were 2.5- and 1.6-fold greater than docetaxel in H460 and LS174 xenograft models, respectively. Further, 4-ARM-PEG$_{20K}$-BA-DOC was well tolerated, with weight loss at MTD comparable to docetaxel and no significant clinical observations. In summary, the foregoing illus- Plasma 4-ARM-PEG$_{20K}$-BA-docetaxel concentrations declined in a multiphasic fashion with an average terminal half-life of 65 hr. 4-ARM-PEG$_{20K}$-BA-docetaxel clearance was low at 0.33 mL/min/kg. The Vss was similar to the total body water, indicating distribution outside the vascular space. $T_{1/2}$, CL, and $V_{ss}$ were independent of dose. $C_{max}$ and AUC values increased in a dose-related and generally dose-proportional manner.

Plasma docetaxel concentrations declined in a multiphasic fashion and remained sustained after administration of 4-ARM-PEG$_{20K}$-BA-docetaxel. Docetaxel $C_{max}$ values were reached between 0.5-2 hr after the 4-ARM-PEG$_{20K}$-BA-docetaxel dose, indicating that a portion of docetaxel is released quickly. At equivalent doses (5 mg/kg or 30 mg/mm²) 4-ARM-PEG$_{20K}$-BA-docetaxel, 4-ARM-PEG$_{20K}$-BA-docetaxel treatment resulted in about a 6-fold lower $C_{max}$ but similar AUC. Docetaxel $C_{max}$ and AUC after 4-ARM-PEG$_{20K}$-BA-docetaxel increased in a dose-related and generally dose-proportional manner.

Standard non-compartmental analysis did not allow accurate estimation of the long docetaxel terminal half-life after administration of 4-ARM-PEG$_{20K}$-BA-docetaxel, due in part to the sustained presence of docetaxel and the variability associated with concentrations in the slowest disposition phase occurring near the lower limit of quantification (1 ng/mL). To further evaluate the sustained plasma docetaxel terminal half-life, a population pharmacokinetic approach was employed. The population pharmacokinetic analysis estimated a terminal half life for docetaxel of 168 hr after administration of 4-ARM-PEG$_{20K}$-BA-docetaxel and 40 hr after administration of docetaxel.

Based upon the foregoing, 4-ARM-PEG$_{20K}$-BA-docetaxel when administered to rats has a low clearance and low volume of distribution, resulting in a long 4-ARM-PEG$_{20K}$-BA-docetaxel terminal half life of 65 hr. Plasma docetaxel $C_{max}$ is approximately 6-fold lower after administration of equivalent 4-ARM-PEG$_{20K}$-BA-docetaxel and docetaxel doses, while AUC is similar. Plasma docetaxel half-life is estimated to be about 4-fold longer following 4-ARM-PEG$_{20K}$-BA-docetaxel administration than that observed following docetaxel administration (168 vs. 40 hr) resulting in sustained systemic docetaxel exposure.

Example 15

Pharmacokinetics of Docetaxel and 4-ARM-PEG$_{20K}$-BA-docetaxel in Beagle Dogs The objective of the study was to assess the pharmacokinetics and excretion of docetaxel and 4-ARM-PEG$_{20K}$-BA-docetaxel after intravenous infusion to dogs.

Pharmacokinetics were evaluated in male dogs (4 dogs/dose level) dosed with 0, 0.75, 2, or 4 mg/kg (0, 15, 40, and 80 mg/m$^2$/dose) of 4-ARM-PEG$_{20K}$-BA-docetaxel or 0.75 mg/kg (15 mg/m$^2$) docetaxel. 4-ARM-PEG$_{20K}$-BA-docetaxel and docetaxel were administered via a cephalic or saphenous vein disposable catheter as 60-min intravenous infusions at 4 mL/kg/hr. Seventeen blood samples were obtained by jugular venipuncture or Abbacoth IV catheter between 0 and 168 hr post-dose. Plasma concentrations of 4-ARM-PEG$_{20K}$-BA-docetaxel and docetaxel were determined.

Pharmacokinetic parameters are summarized in Table 6.

Plasma docetaxel concentrations declined in a multiphasic fashion and remained sustained after administration of 4-ARM-PEG$_{20K}$-BA-docetaxel. Docetaxel $C_{max}$ values are reached between 0.88-12 hr after the 4-ARM-PEG$_{20K}$-BA-docetaxel dose, indicating that a portion of docetaxel is released quickly. At docetaxel and 4-ARM-PEG$_{20K}$-BA-docetaxel equivalent dose levels of 0.75 mg/kg, 4-ARM-PEG$_{20K}$-BA-docetaxel treatment resulted in a 110-fold lower $C_{max}$ and 7-fold lower AUC. Docetaxel Cmax and AUC increase in a dose-related and generally dose-proportional manner.

Standard noncompartmental analysis did not allow accurate estimation of the long docetaxel terminal half-life after administration of 4-ARM-PEG$_{20K}$-BA-docetaxel, due in part to the sustained presence of docetaxel and the variability associated with concentrations in the slowest disposition phase occurring near the lower limit of quantification (1 ng/mL). To further evaluate the sustained plasma docetaxel terminal half-life, a population pharmacokinetic approach was employed. The population pharmacokinetic analysis predicts a docetaxel terminal half life in dogs of 199 hours after administration of 4-ARM-PEG$_{20K}$-BA-docetaxel, and 25 hr after administration of docetaxel.

Lower docetaxel AUC after 4-ARM-PEG$_{20K}$-BA-docetaxel is likely due to incomplete capture of AUC because of a relatively short sampling period (168 hours) in the presence of a 199-hour apparent half-life. Based on this finding, it is likely that docetaxel release from 4-ARM-PEG$_{20K}$-BA-docetaxel continues for a significant time after dosing.

Based upon this study, 4-ARM-PEG$_{20K}$-BA-docetaxel has a low clearance and low volume of distribution, resulting in a long 4-ARM-PEG$_{20K}$-BA-docetaxel terminal half-life of 31 hr. Plasma docetaxel $C_{max}$ and AUC are about 110- and 7-fold lower, respectively, following administration of equivalent 4-ARM-PEG$_{20K}$-BA-docetaxel and docetaxel doses. Lower

TABLE 6

Docetaxel and 4-ARM-PEG20K-BA-Docetaxel Pharmacokinetic Parameters in Male Dogs after Single IV Doses of 0.75 mg/kg Docetaxel, and 0.75, 2, and 4 mg/kg 4-ARM-PEG$_{20K}$-BA-docetaxel

| Treatment | Dose (mg/kg) | Analyte | $T_{1/2}$ (hr) | Tmax (hr) | Cmax (ng/mL) | AUClast (hr * ng/mL) | AUCinf (hr * ng/mL) | CL (mL/min/kg) | Vss (L/kg) |
|---|---|---|---|---|---|---|---|---|---|
| Docetaxel | 0.75 | Docetaxel | ND[1] | 0.88 | 223 | 479 | ND | ND[2] | ND |
| Conjugate | 0.75 | Docetaxel | ND | 0.88 | 2.1 | 64 | ND | NA | NA |
|  |  | Conjugate | 28 | 1.1 | 7084 | 93084 | 104247 | 0.12 | 0.23 |
| Conjugate | 2 | Docetaxel | ND | 1.1 | 6.3 | 153 | ND | NA | NA |
|  |  | Conjugate | 35 | 1.4 | 17731 | 232378 | 245446 | 0.14 | 0.26 |
| Conjugate | 4 | Docetaxel | ND | 12 | 19 | 326 | ND | NA | NA |
|  |  | Conjugate | 32 | 6.8 | 33570 | 597336 | 611470 | 0.12 | 0.31 |
| Average Conjugate (±SD) |  |  | 32 ± 4 |  |  |  |  | 0.13 ± 0.01 | 0.26 ± 0.04 |

[1]ND = not determined; terminal phase not well defined
[2]NA = not applicable for the docetaxel metabolite
*Conjugate = 4-ARM-PEG$_{20K}$-BA-docetaxel Plasma 4-ARM-PEG$_{20K}$-BA-docetaxel concentrations declined in a multiphasic fashion with an average terminal half-life of 31 hr. 4-ARM-PEG$_{20K}$-BA-docetaxel clearance was low at 0.13 mL/min/kg. The Vss was less than total body water, indicating limited distribution outside the vascular space. $T_{1/2}$, CL, and $V_{ss}$ are independent of dose. $C_{max}$ and AUC values following 4-ARM-PEG$_{20K}$-BA-docetaxel administration increased in a dose-related and generally dose-proportional manner.

docetaxel AUC after 4-ARM-PEG$_{20K}$-BA-docetaxel is likely due to incomplete capture of AUC because of a relatively short sampling period (168 hours) in the presence of a 199-hour apparent half-life. Plasma docetaxel half-life following 4-ARM-PEG$_{20K}$-BA-docetaxel administration is estimated to be about 8-fold longer than that observed following docetaxel administration (199 vs. 25 hours) confirming the sustained systemic docetaxel exposure observed in rats.

Example 16

Nonlinear Mixed Effect Modeling of Terminal Disposition Rate Constants

While determining the pharmacokinetics of docetaxel after administration of docetaxel or 4-ARM-PEG$_{20K}$-BA-docetaxel, it was observed that reliable values for the terminal disposition rate constant $\lambda_z$ could not be obtained for the majority of animals secondary to fluctuation of plasma docetaxel concentrations between adjacent sampling times and/or the occurrence of incomplete concentration-time profiles due to concentrations being near or at the lower limit of quantification (1 ng/mL). In addition, in Example 14, rats were sampled in groups of 15 using alternating, overlapping sparse sampling schemes across groups to encompass the total duration of sampling. All of these factors contributed to the occurrence of sparse data within a given animal's terminal concentration-time profile.

To further investigate and compare docetaxel terminal disposition patterns between docetaxel and 4-ARM-PEG$_{20K}$-BA-docetaxel, population pharmacokinetic methods were applied to data from rats (Example 14) and dogs (Example 15 and in one additional study). This allowed estimation of population $\lambda_z$ values and corresponding half-life values for each treatment group in the presence of incomplete data within individual animals. Specifically, data from all animals within a treatment group and all treatment groups were fit with a nonlinear mixed effect pharmacokinetic model using the program Monolix. Plasma docetaxel concentrations following docetaxel or 4-ARM-PEG$_{20K}$-BA-docetaxel administration, and plasma 4-ARM-PEG$_{20K}$-BA-docetaxel concentrations following 4-ARM-PEG$_{20K}$-BA-docetaxel administration were fit with a model specifying zero-order input of the dose over a defined infusion period and biexponential disposition (Monolix PK Model 26). Docetaxel concentration-time data after 4-ARM-PEG$_{20K}$-BA-docetaxel were fit with a model having first order input, to reflect metabolism of 4-ARM-PEG$_{20K}$-BA-docetaxel to the active docetaxel metabolite, and biexponential disposition (Monolix PK Model 31). The parameter of interest for this investigation was the population terminal disposition rate constant, X, to supplement the results described above.

A. Population Modeling Results for Docetaxel in Sprague-Dawley Rats

Plasma docetaxel concentration-time profiles in rats after administration of docetaxel or 4-ARM-PEG$_{20K}$-BA-docetaxel were well fit with the respective models. It was possible to obtain a population estimate for $\lambda_z$ for all 4 treatment groups. The results show that docetaxel concentrations in the terminal disposition phase following administration of all doses of 4-ARM-PEG$_{20K}$-BA-docetaxel are more sustained than those following administration of docetaxel.

The population mean (SE) $\lambda_z$ estimates for docetaxel following administration of docetaxel and 4-ARM-PEG$_{20K}$-BA-docetaxel to rats are 0.0174 (0.0018) hr$^{-1}$ and 0.00412 (0.001) hr$^{-1}$, respectively, with corresponding t1/2$_{\lambda z}$ values of 40 and 168 h.

B. Population Modeling Results for Docetaxel in Beagle Dogs

Plasma docetaxel concentration-time profiles in dogs after administration of docetaxel or 4-ARM-PEG$_{20K}$-BA-docetaxel were well fit with the respective models. It was possible to obtain a population estimate for $\lambda_z$ for all 4 treatment groups. The modeling supports that docetaxel concentrations in the terminal disposition phase following administration of all doses of 4-ARM-PEG$_{20K}$-BA-docetaxel are more sustained than those following administration of docetaxel, consistent with the trend observed in rats.

The population mean (SE) $\lambda_z$ estimates for docetaxel following administration of docetaxel and 4-ARM-PEG$_{20K}$-BA-docetaxel to dogs are 0.0276 (0.0022) hr$^{-1}$ and 0.00349 (0.0021) hr$^{-1}$, respectively, with corresponding t1/2$_{\lambda z}$ values of 25 and 199 hr.

Dogs in the additional study received 7 mg/kg doses of 4-ARM-PEG$_{20K}$-BA-docetaxel on Days 1 and 22 with serial blood sampling after each dose for determination of plasma 4-ARM-PEG$_{20K}$-BA-docetaxel and docetaxel concentrations.

The population mean (SE) $\lambda_z$ estimates for 4-ARM-PEG$_{20K}$-BA-docetaxel and docetaxel following administration of 4-ARM-PEG$_{20K}$-BA-docetaxel to dogs are 0.0141 (0.00041) h$^{-1}$ and 0.00627 (0.00086) h$^{-1}$, respectively, with corresponding t1/2$_{\lambda z}$ values of 49 and 110 hr.

When compared within and across studies, population mean $\lambda_z$ estimates show that plasma docetaxel concentrations are sustained following administration of 4-ARM-PEG$_{20K}$-BA-docetaxel relative to administration of docetaxel, independent of species and dose.

TABLE 7

Summary of Docetaxel Population Mean $\lambda_z$ Estimates and Corresponding t½$\lambda$z Values Across Species and Studies.

| Species | Treatment | Dose (mg/kg) | Mean (SE) $\lambda_z$ (hr$^{-1}$) | t½$_{\lambda z}$ (hr) |
|---|---|---|---|---|
| Rat | Docetaxel | 5 | 0.0174 (0.0018) | 40 |
|  | Conjugate | 5, 10, 15 | 0.00412 (0.001) | 168 |
| Dog | Docetaxel | 0.75 | 0.0276 (0.0022) | 25 |
|  | Conjugate | 0.72, 2, 4 | 0.00349 (0.0021) | 199 |
| Dog | Conjugate | 7 | 0.00627 (0.00086) | 110 |

*Conjugate = 4-ARM-PEG$_{20K}$-BA-docetaxel

Values for docetaxel t½$_{\lambda z}$ after 4-ARM-PEG$_{20K}$-BA-docetaxel are 4- to 8-fold greater than those after docetaxel in rats and dogs, providing evidence of the desired characteristics of prolonged docetaxel half-life and extended exposure.

Example 17

Pharmacokinetic Study of 4-ARM-PEG$_{20K}$-BA-DOCETAXEL in Female Athymic Nude Mice Implanted Subcutaneously with H460 NSCLC Tumor Fragments The objective of this study was to compare docetaxel pharmacokinetics following 4-ARM-PEG$_{20K}$-BA-docetaxel with that following docetaxel administration, in plasma and tumor tissue of athymic female mice bearing H460 NSCLC tumors and to determine the effects on complete blood counts. This example summarizes the pharmacokinetic results.

H460 tumor cells were grown in vitro and implanted subcutaneously into female HRLN nude mice. When tumor sizes reached between 172 and 288 mg, animals were dosed by intravenous bolus injection with 25 mg/kg docetaxel or 33 mg/kg 4-ARM-PEG$_{20K}$-BA-docetaxel at a dosing volume of 10 mL/kg. These dose levels correspond to the maximum tolerated doses for docetaxel and 4-ARM-PEG$_{20K}$-BA-docetaxel administered on a q7dx3 schedule in this tumor model. Blood and tumor samples (n=7 timepoints with n=3/timepoint) were collected from 0 to 7 days after IV injection. Plasma and tumor samples were analyzed for docetaxel and 4-ARM-PEG$_{20K}$-BA-docetaxel.

Both 4-ARM-PEG$_{20K}$-BA-docetaxel lots resulted in comparable plasma and tumor drug concentration time profiles.

4-ARM-PEG$_{20K}$-BA-docetaxel distributes to and remains in the tumor tissue, resulting in a tumor to plasma ratio of about 7 by 168 hr post-dose.

Plasma docetaxel concentrations fell below the limit of quantitation (1 ng/mL) by 72 hr after administration of docetaxel, while they remained above 5 ng/mL for up to 168 hr after administration of 4-ARM-PEG$_{20K}$-BA-docetaxel. These results demonstrate sustained systemic exposure to docetaxel after 4-ARM-PEG$_{20K}$-BA-docetaxel administration in a third animal species. Both lots of 4-ARM-PEG$_{20K}$-BA-docetaxel resulted in comparable plasma and tumor docetaxel concentration-time profiles.

Plasma and tumor 4-ARM-PEG$_{20K}$-BA-docetaxel and docetaxel exposure data are summarized in Table 8.

TABLE 8

Plasma and Tumor Exposures after Administration of 25 mg/kg Docetaxel and 33 mg/kg 4-ARM-PEG$_{20K}$-BA-docetaxel to H460-Bearing Nude Mice

| Treatment | Dose (mg/kg) | Analyte | Compartment | Tmax (hr) | Cmax (ng/mL) | AUClast (hr * ng/mL) | Conjugate to Docetaxel ratio Cmax | Conjugate to Docetaxel ratio AUC |
|---|---|---|---|---|---|---|---|---|
| Docetaxel | 25 | Docetaxel | Plasma | 0.5 | 2571 | 6146 | | |
| | | | Tumor | 4 | 2336 | 138715 | | |
| Conjugate Lot 1 | 33 | Conjugate | Plasma | 0.5 | 128354 | 1097606 | | |
| | | | Tumor | 4 | 7062 | 652823 | | |
| | | Docetaxel | Plasma | 12 | 195 | 6013 | 0.08 | 1.0 |
| | | | Tumor | 12 | 2931 | 313558 | 1.3 | 2.3 |
| Conjugate Lot 2 | 33 | Conjugate | Plasma | 0.5 | 118209 | 1852510 | | |
| | | | Tumor | 4 | 7675 | 718068 | | |
| | | Docetaxel | Plasma | 12 | 162 | 5570 | 0.06 | 0.9 |
| | | | Tumor | 12 | 4623 | 380617 | 2.0 | 2.7 |

*Conjugate = 4-ARM-PEG$_{20K}$-BA-docetaxel

Plasma 4-ARM-PEG$_{20K}$-BA-docetaxel Cmax was reached in 0.5 hr post-dose (first timepoint measured). Tumor Cmax was reached by 4 hr post-dose. 4-ARM-PEG$_{20K}$-BA-docetaxel Cmax was 17-fold and AUC approximately 2-fold lower in tumor compared to plasma.

Plasma docetaxel Cmax was reached in 0.5 hr post-dose (first timepoint measured) independent of treatment. Tumor docetaxel Cmax was reached by 4 hr post docetaxel dose and 12 hr post 4-ARM-PEG$_{20K}$-BA-docetaxel dose. Plasma docetaxel Cmax was reduced about 14-fold after administration of 4-ARM-PEG$_{20K}$-BA-docetaxel, but the sustained plasma drug concentrations after 4-ARM-PEG$_{20K}$-BA-docetaxel resulted in similar mean docetaxel AUC values after 4-ARM-PEG$_{20K}$-BA-docetaxel for both treatments. The rate of decline in tumor docetaxel concentrations appeared similar after administration of docetaxel and 4-ARM-PEG$_{20K}$-BA-docetaxel, although tumor docetaxel concentrations after 4-ARM-PEG$_{20K}$-BA-docetaxel were approximately 5-fold higher in the period from 24 hr post dose through the end of sampling, demonstrating greater and sustained tumor docetaxel exposure.

The greater and sustained tumor docetaxel exposure after 4-ARM-PEG$_{20K}$-BA-docetaxel correlated with a significantly longer H460 tumor growth delay for 4-ARM-PEG$_{20K}$-BA-docetaxel vs. docetaxel (122 vs. 48%).

This study provides evidence that the superior antitumor activity of 4-ARM-PEG$_{20K}$-BA-docetaxel is mediated by increased and sustained tumor docetaxel exposure.

Example 18

Stability of 4-ARM-PEG$_{20K}$-BA-DOCETAXEL in Mouse, Rat, Dog and Human Plasma

The objective of the study was to assess the stability of 4-ARM-PEG$_{20K}$-BA-docetaxel in mouse, rat, dog, and human plasma.

4-ARM-PEG$_{20K}$-BA-docetaxel was spiked (50 µg/mL; 60 µM) into heparinized, pooled male mouse, rat, and dog plasma; mixed sex pooled human plasma; and phosphate buffered saline. Triplicate samples were incubated at 37° C. for 0, 15, 30, 60, 120, and 240 min. Aliquots were removed at each timepoint and analyzed for disappearance of 4-ARM-PEG$_{20K}$-BA-docetaxel and appearance of docetaxel using the validated dog plasma analytical method.

Table 9 summarizes the disappearance of 4-ARM-PEG$_{20K}$-BA-docetaxel and appearance of docetaxel at the end of the 240-minute incubation period.

TABLE 9

Plasma Stability of 4-ARM-PEG$_{20K}$-BA-docetaxel after Incubation with Buffer, Mouse, Rat, Dog and Human Plasma

| | Mouse | Rat | Dog | Human | Buffer |
|---|---|---|---|---|---|
| Conjugate* remaining at 4 hr (%) | 72 | 64 | 93 | 88 | 85 |
| Docetaxel released at 4 hr (%)[1] | 20 | 20 | 3 | 4 | 0.6 |
| Mass balance (%) | 92 | 84 | 95 | 92 | 86 |

[1]Mean (n = 3), expressed as a percentage of starting conjugate concentrations.
2 Mean (n = 3), expressed as a percentage of total docetaxel content.
*Conjugate = 4-ARM-PEG$_{20K}$-BA-docetaxel Docetaxel release from 4-ARM-PEG$_{20K}$-BA-docetaxel was detected in plasma from all 4 species after 4 hr of incubation. Docetaxel percent released was 20% in mouse and rat plasma but notably less and similar in dog (3%) and human plasma (4%). This finding is consistent with reports that rodents have more esterases with greater esterase activity than non-rodent species (Williams F. M., *Clin. Pharmacokinet.* 1985:10:392-403, Kaliste-Korhonen E, et al., *Human & Experimental Toxicology* 1996:15:972-978, Li, B., et al., *Biochem. Pharmacol* 2005:70:1673-1684), and that rodents typically metabolize ester containing drugs and prodrugs at greater rates and to a greater extent (Li, B., et al., *Biochem.*

Pharmacol 2005;70:1673-1684; Cook C. S., et al., *Pharm. Res.* 1995;12:1158-1164; Quon C. Y., et al., *Drug Metabolism and Disposition* 1988;16:425-428; Minagawa T, et al., *Biochem. Pharmacol.* 1995;49:1361-1365; Ericsson H., et al., *Eur. J. Pharm. Sci.* 1999;8:29-37). The results of this study are consistent with reports that metabolism of ester containing drugs and prodrugs by rodents is not necessarily representative or predictable of that in humans.

Docetaxel is released from 4-ARM-PEG$_{20K}$-BA-docetaxel after incubation in mouse, rat, dog, and human plasma. The release of docetaxel is notably faster in rodent plasma than in non-rodent plasma, suggesting that rodents are less reliable than the dog as predictors of human metabolism of 4-ARM-PEG$_{20K}$-BA-docetaxel.

Example 19

Dose Escalation Study of Exemplary Multi-Armed Polymer Alkanoate Linked Docetaxel Conjugates This study was undertaken to investigate the effect of polymer size and linker identity on the toxicity of the conjugate. Docetaxel conjugates as described in Example 12 were investigated to determine their maximum tolerated dose (MTD) when administered to Sprague-Dawley rats as a single dose.

Healthy rats were randomized into eighteen groups of five male and 5 females per group. Weight variation of the animals did not exceed ±10% of mean body weight. Prior to dosing, each of the test articles was dissolved in 5% dextrose solution in sterile water for injection. The articles were each dosed as a single intravenous bolus injection in conscious rats. Dose volume was maintained at 2 mL/kg body weight.

A dose of 12.5 mg/kg (docetaxel equivalents) for all agents was administered first to groups of 5 male and 5 female rats. If the mortality was 10% or less at 48 hours after dosing, a dose of 20 mg/kg of the test agent was administered to the next groups of 5 male and 5 female rats. If mortality from the 12.5 mg/kg dose was greater than 10%, the second dose was subsequently modified. The third dose was administered based on the results from the first two doses and was adjusted accordingly on the basis of the mortality results obtained.

Clinical observations were performed 15 minutes, 30 minutes, 1, 2, 3, and 4 hours after dosing and once post-noon observation on the day of test article administration. The observations were continued twice daily, once in the morning and in the afternoon on the remaining 14 day observation period.

Overall mortality was determined after 14 days observation at each dose level. See the results in Table 10 below. As noted above, mortality within first 48 hours of dosing was used to escalate to the next higher dose. Clinical signs before death included reduced locomotor activity, ataxic gait, polyurea, diarrhoea and emaciation.

TABLE 10

| Dose DE (mg/kg) | 10K BA M | 10K BA F | 30K BA M | 30K BA F | 40K BA M | 40K BA F | 20K β MPA M | 20K β MPA F | 20K OA M | 20K OA F |
|---|---|---|---|---|---|---|---|---|---|---|
| 12.5 | 0/5 | 0/5 | 2/5 | 1/5 | 4/5 | 4/5 | 0/5 | 0/5 | 0/5 | 0/5 |
| 20 | 0/5 | 0/5 | 4/5 | 5/5 | 5/5 | 5/5 | 0/5 | 0/5 | 0/5 | 0/5 |
| 25 | 0/5 | 0/5 | 5/5 | 5/5 | 5/5 | 5/5 | 0/5 | 0/5 | 0/5 | 0/5 |

In looking at the results, it can be seen that for the butanoate-linked conjugates, preliminary toxicity data indicate that the relative order of toxicity in rats, based upon polymer molecular weight, is: 10K<20K<30K<40K. In comparing data over one polymer molecular weight (i.e., constant polymer size of 20K) versus linker structure, based solely on the rat data, it appears that the relative order of toxicity is MPA is about the same as OA<BA<HA.

The invention(s) set forth herein has been described with respect to particular exemplified embodiments. However, the foregoing description is not intended to limit the invention to the exemplified embodiments, and the skilled artisan should recognize that variations can be made within the spirit and scope of the invention as described in the foregoing specification.

What is claimed is:

1. A pharmaceutical composition comprising a multi-armed polymer conjugate having the structure,

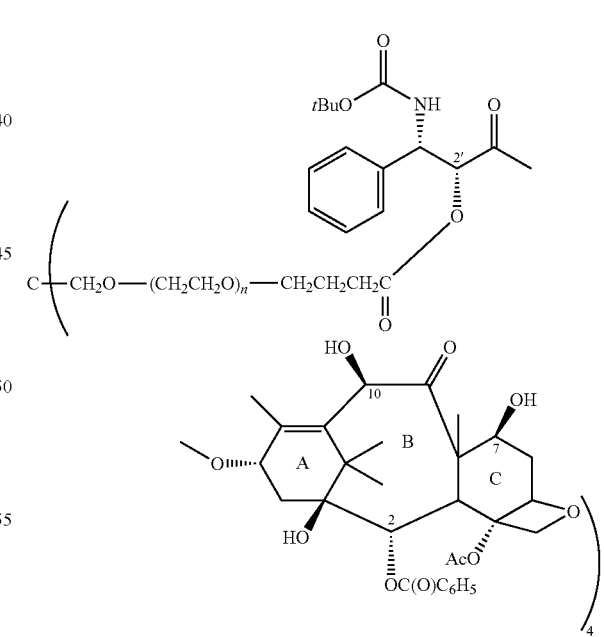

where n ranges from about 40 to about 500, or a pharmaceutically acceptable salt thereof; and
a pharmaceutically acceptable excipient.

2. The composition of claim 1, wherein the weight average molecular weight of the conjugate is about 20,000 daltons.

* * * * *